US009550795B2

(12) United States Patent
Brodney et al.

(10) Patent No.: US 9,550,795 B2
(45) Date of Patent: Jan. 24, 2017

(54) HEXAHYDROPYRANO[3,4-D][1,3]THIAZIN-2-AMINE COMPOUNDS

(71) Applicants: Michael Aaron Brodney, Newton, MA (US); Christopher Ryan Butler, Canton, MA (US); Christopher John Helal, Mystic, CT (US); Brian Thomas O'Neill, Haddam, CT (US)

(72) Inventors: Michael Aaron Brodney, Newton, MA (US); Christopher Ryan Butler, Canton, MA (US); Christopher John Helal, Mystic, CT (US); Brian Thomas O'Neill, Haddam, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 14/560,190

(22) Filed: Dec. 4, 2014

(65) Prior Publication Data

US 2015/0087637 A1    Mar. 26, 2015

Related U.S. Application Data

(63) Continuation of application No. 13/596,208, filed on Aug. 28, 2012, now Pat. No. 8,933,221.

(60) Provisional application No. 61/529,367, filed on Aug. 31, 2011.

(51) Int. Cl.
*C07D 513/04*     (2006.01)
(52) U.S. Cl.
CPC .................... *C07D 513/04* (2013.01)
(58) Field of Classification Search
CPC ................................................... C07D 513/04
See application file for complete search history.

(56) References Cited

U.S. PATENT DOCUMENTS

| | | | |
|---|---|---|---|
| 5,750,349 A | 5/1998 | Suzuki et al. |
| 7,115,600 B2 | 10/2006 | Wager et al. |
| 7,285,293 B2 | 10/2007 | Castillo et al. |
| 7,975,664 B2 | 7/2011 | Himsel et al. |
| 8,158,620 B2 | 4/2012 | Suzuki et al. |
| 8,198,269 B2 | 6/2012 | Motoki et al. |
| 8,278,441 B2 | 10/2012 | Mergott et al. |
| 8,822,456 B2 | 9/2014 | Brodney et al. |
| 8,865,706 B2 | 10/2014 | Brodney et al. |
| 8,962,616 B2 | 2/2015 | Brodney et al. |
| 9,045,498 B2 | 6/2015 | Brodney et al. |
| 9,045,499 B2 | 6/2015 | Brodney et al. |
| 9,192,612 B2 | 11/2015 | Brodney et al. |
| 9,198,917 B2 | 12/2015 | Brodney et al. |
| 9,233,981 B1 | 1/2016 | Brodney et al. |
| 9,315,520 B2 | 4/2016 | Brodney et al. |
| 2003/0073655 A1 | 4/2003 | Chain |
| 2003/0195205 A1 | 10/2003 | DeNinno et al. |
| 2004/0192898 A1 | 9/2004 | Jia et al. |
| 2004/0220186 A1 | 11/2004 | Bell et al. |
| 2005/0019328 A1 | 1/2005 | Schenk |
| 2005/0043354 A1 | 2/2005 | Wager et al. |
| 2005/0048049 A1 | 3/2005 | Schenk |
| 2005/0256135 A1 | 11/2005 | Lunn et al. |
| 2005/0267095 A1 | 12/2005 | Bernardelli et al. |
| 2005/0267100 A1 | 12/2005 | Elliott et al. |
| 2006/0057701 A1 | 3/2006 | Rosenthal et al. |
| 2006/0106035 A1 | 5/2006 | Hendrix et al. |
| 2006/0111372 A1 | 5/2006 | Hendrix et al. |
| 2006/0178501 A1 | 8/2006 | Summers et al. |
| 2007/0031416 A1 | 2/2007 | Shoji et al. |
| 2007/0160616 A1 | 7/2007 | Rosenthal et al. |
| 2007/0179175 A1 | 8/2007 | Lunn |
| 2008/0096955 A1 | 4/2008 | Wager et al. |
| 2008/0176925 A1 | 7/2008 | Butler et al. |

(Continued)

FOREIGN PATENT DOCUMENTS

| | | |
|---|---|---|
| EP | 0994728 | 10/1998 |
| EP | 1257584 | 10/2004 |

(Continued)

OTHER PUBLICATIONS

Alberti, K.G. et al., "The Metabolic Syndrome—A New Worldwide Definition," Lancet, Sep. 24-30, 2005, pp. 1059-1062, 366(9491).
Carpino, P.A., et al., "Diabetes Area Participation Analysis: A Review of Companies and Targets Described in the 2008-2010 Patent Literature", Expert Opinion on Therapeutic Patents, Dec. 2010, pp. 1627-1651, 20(12).
Chao, Edward, et al., "SGLT2 Inhibition—A Novel Strategy for Diabetes Treatment", Nature Reviews Drug Discovery, Jul. 2010, pp. 551-559, 9(7).
Demong, D.E. et al., "Chapter 8, Glucagon Receptor Antagonists for Type II Diabetes", Annual Reports in Medicinal Chemistry 2008, pp. 119-137, vol. 43.
England, et al., "An Improved Synthesis of a Novel α1A Partial Agonist Including a New Two-Step Synthesis of 4-Fluoropyrazole", Tetrahedron Letters, May 26, 2010, pp. 2849-2851, 51(21).

(Continued)

*Primary Examiner* — Sarah Pihonak
*Assistant Examiner* — Jason A Deck
(74) *Attorney, Agent, or Firm* — John A. Wichtowski

(57) ABSTRACT

Compounds and pharmaceutically acceptable salts of the compounds are disclosed, wherein the compounds have the structure of Formula I,

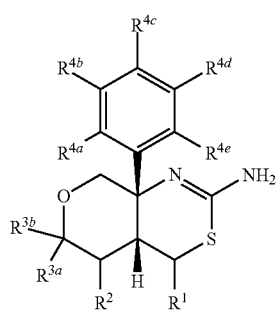

as defined in the specification. Corresponding pharmaceutical compositions, methods of treatment, methods of synthesis, and intermediates are also disclosed.

5 Claims, No Drawings

(56) References Cited

U.S. PATENT DOCUMENTS

| | | | |
|---|---|---|---|
| 2009/0054482 A1 | 2/2009 | Chan et al. | |
| 2010/0056618 A1 | 3/2010 | Mascitti et al. | |
| 2010/0093999 A1* | 4/2010 | Motoki | C07D 513/04 |
| | | | 544/48 |
| 2010/0285145 A1 | 11/2010 | Darout et al. | |
| 2011/0027279 A1 | 2/2011 | Chain | |
| 2011/0038861 A1 | 2/2011 | Rosenthal et al. | |
| 2011/0046122 A1 | 2/2011 | Andreini et al. | |
| 2011/0207723 A1 | 8/2011 | Motoki et al. | |
| 2012/0245155 A1 | 9/2012 | Yoshida et al. | |
| 2013/0296308 A1 | 11/2013 | Brodney et al. | |
| 2015/0133438 A1 | 5/2015 | Brodney et al. | |
| 2015/0224110 A1 | 8/2015 | Brodney et al. | |
| 2015/0231144 A1 | 8/2015 | Brodney et al. | |
| 2015/0239908 A1 | 8/2015 | Brodney et al. | |

FOREIGN PATENT DOCUMENTS

| | | |
|---|---|---|
| EP | 2332943 | 6/2011 |
| WO | 9844955 | 10/1998 |
| WO | 0220521 | 3/2002 |
| WO | 03072197 | 9/2003 |
| WO | 2004032868 | 4/2004 |
| WO | 2005025616 | 3/2005 |
| WO | 2005049616 | 6/2005 |
| WO | 2005116014 | 12/2005 |
| WO | 2006036291 | 4/2006 |
| WO | 2006069081 | 6/2006 |
| WO | 2006118959 | 11/2006 |
| WO | 2006120552 | 11/2006 |
| WO | 2006126081 | 11/2006 |
| WO | 2006126082 | 11/2006 |
| WO | 2006126083 | 11/2006 |
| WO | 2006136924 | 12/2006 |
| WO | 2007063385 | 6/2007 |
| WO | 2007069053 | 6/2007 |
| WO | 2007088450 | 8/2007 |
| WO | 2007088462 | 8/2007 |
| WO | 2007099423 | 9/2007 |
| WO | 2007105053 | 9/2007 |
| WO | 2007122466 | 11/2007 |
| WO | 2007122482 | 11/2007 |
| WO | 2007138431 | 12/2007 |
| WO | 2008065508 | 6/2008 |
| WO | 2009016462 | 2/2009 |
| WO | 2009091016 | 7/2009 |
| WO | 2009144554 | 12/2009 |
| WO | 2009144555 | 12/2009 |
| WO | 2010013161 | 2/2010 |
| WO | 2010038686 | 4/2010 |
| WO | 2010086820 | 8/2010 |
| WO | 2010103437 | 9/2010 |
| WO | 2010103438 | 9/2010 |
| WO | 2010106457 | 9/2010 |
| WO | 2010140092 | 12/2010 |
| WO | 2011005611 | 1/2011 |
| WO | 2011071109 | 6/2011 |
| WO | 2012098461 | 7/2012 |
| WO | 2012162334 | 11/2012 |
| WO | 2013030713 | 3/2013 |
| WO | 2013164730 | 11/2013 |

OTHER PUBLICATIONS

Esterhazy, Daria, et al., "BACE2 is a β Cell-Enriched Protease that Regulates Pancreatic β Cell Function and Mass", Cell Metabolism, Sep. 2011, pp. 365-377, 14(3).
Farah, M., et al., "Reduced BACE1 Activity Enhances Clearance of Myelin Debris and Regeneration of Axons in the Injured Peripheral Nervous System", Journal of Neuroscience, Apr. 13, 2011, pp. 5744-5754, 31(15).
Jones, R.M. et al., "Chapter 7, The Emergence of GPR119 Agonists as Anti-Diabetic Agents", Annual Reports in Medicinal Chemistry 2009, pp. 149-170, vol. 44.
Kharitonenkov, A. et al., "FGF21: A Novel Prospect for the Treatment of Metabolic Diseases", Current Opinion in Investigational Drugs, Apr. 2009, pp. 359-364, 10(4).
Meakin, Paul, et al., "Reduction in BACE1 decreases body weight, protects against diet-induced obesity and enhances insulin sensitivity in mice", Biochemical Journal, Jan. 1, 2012, pp. 285-296, 441(1).
Medina, J.C., et al., "Chapter 5, GPR40 (FFAR1) Modulators", Annual Reports in Medicinal Chemistry 2008, pp. 75-85, vol. 43.
Zhang, S. et al., "PTP1B as a Drug Target: Recent Developments in PTP1B Inhibitor Discovery", Drug Discovery Today, May 2007, pp. 373-381, 12(9/10).
Zhong, M., "TGR5 as a Therapeutic Target for Treating Obesity", Current Topics in Medicinal Chemistry, 2010, pp. 386-396, 10(4).
Zimmet, P.Z. et al., "The Metabolic Syndrome: Perhaps an Etiologic Mystery but Far From a Myth—Where Does the International Diabetes Federation Stand?," Medscape Diabetes & Endocrinology, Oct. 11, 2005, 8 pages, www.medscape.com, 7(2).
International Application No. PCT/IB2013/053178, filed Apr. 22, 2013, International Written Opinion and Search Report, mailed Jul. 3, 2013, 10 pages.
International Application No. PCT/IB2013/060633 application filed Dec. 4, 2013.
International Application No. PCT/IB2013/058402 application filed Sep. 9, 2013.
International Application No. PCT/IB2013/060456 application filed Nov. 27, 2013.
International Application No. PCT/IB2014/058760 application filed Feb. 3, 2014.
International Application No. PCT/IB2014/058777 application filed Feb. 4, 2014.
International Application No. PCT/IB2013/058402, filed Sep. 9, 2013, International Search Report, mailed Dec. 16, 2013, 11 pages.
International Application No. PCT/IB2013/060456, filed Nov. 27, 2013, International Search Report, mailed Feb. 21, 2014, 8 pages.
Guidance for Industry, Q3C-Tables and List, U.S. Department of Health and Human Services, Food and Drug Administration, Center for Drug Evaluation and Research (CDER), Center for Biologics Evaluation and Research (CBER), Nov. 2003, ICH, Revision.
International Application No. PCT/IB2012/054198 International Search Report and Written Opinion, date of mailing Jan. 23, 2013, 14, pages.
Haan, J., et al., "Amyloid in Central Nervous system Disease", Clinical Neurology and Neurosurgery, 1990, pp. 305-310, 92(4).
Glenner, G., et al., "Amyloidosis of the Nervous System", Journal of Neurological Sciences, 1989, pp. 1-28, vol. 94.
Olsen, R., et al., "Secretase Inhibitors and Modulators for the Treatment of Alzheimer's Disease", Annual Reports in Medicinal Chemistry, 2007, pp. 27-47, vol. 42.
Haleblain, John, "Characterization of Habits and Crystalline Modification of Solids and Their Pharmaceutical Applications", Journal of Pharmaceutical Science, Aug. 1975, pp. 1269-1288, 64(8).
Finnin, Barrie, et al., "Transdermal Penetration Enhancers: Applications, Limitations, and Potential", Journal of Pharmaceutical Science, Oct. 1999, pp. 955-958, 88(10).
Denmark, S.E., et al., "Allylation of Carbonyls: Methodology and Stereochemistry", Modern Carbonyl Chemistry, 2000, Chapter 10, pp. 299-401.
Suzuki, Akira, "Recent advances in the cross-coupling reactions of organoboron derivatives with organic electrophiles 1995-1998", Journal Organometallic Chemistry, 1999, pp. 147-168, vol. 576.
Miyaura, N., et al., "Palladium-Catalyzed Cross-Coupling Reactions of Organoborn Compounds", Chemical Review, Nov. 1995, pp. 2457-2483, 95(7).
Spek, A.L., "Single-crystal structure validation with the program PLATON", Journal Applied Crystallography, Feb. 2003, pp. 7-13, 36(1).
MacRae, C.F., et al., "Mercury: visualization and analysis of crystal structures", Journal Applied Crystallography, Jun. 2006, pp. 453-457, 39(3).
Hooft, R.W.W., et al., "Determination of absolute structure using Bayesian statistics on Bijvoet differences", Journal Applied Crystallography, 2008, pp. 96-103, 41(1).

(56) References Cited

OTHER PUBLICATIONS

Flack, H.D., "On Enantiomorph-Polarity Estimation", Acta Crystallographica Section C: Crystal Structure Communications, 1983, pp. 867-881, vol. A39.
Sheppeck, J.E. II, et al., "A Convenient and Scaleable Procedure for Removing the Fmoc Group in Solution", Tetrahedron Letters, 2000, pp. 5329-5333, vol. 41(28).
English equivalent U.S. Pat. No. 8,158,620; Suzuki, et al., filed Jan. 16, 2009 for WO 2009091016, published Jun. 23, 2007.
International Application No. PCT/IB2013/060456, filed Nov. 27, 2013, International Preliminary Report on Patentability, mailed Jun. 16, 2015, 5 pages.
International Application No. PCT/IB2013/060633, filed Dec. 4, 2013, International Preliminary Report on Patentability, mailed Jun. 23, 2015.
International Application No. PCT/IB2013/060633, filed Dec. 4, 2013, International Search Report and Written Opinion, mailed Mar. 24, 2014.
International Application No. PCT/IB2015/052279, filed Mar. 27, 2015, International Search Report and Written Opinion, mailed Jun. 24, 2015, 10 pages.
International Patent Application No. PCT/IB2014/058777, filed Feb. 4, 2014, International Search Report and Written Opinion, mailed Mar. 25, 2014, 11 pages.
International Application No. PCT/IB2014/0558777 filed Feb. 4, 2014, International Preliminary Report on Patentability, mailed Aug. 18, 2015, 7 pages.
International Application No. PCT/IB2014/0558760 filed Feb. 3, 2014, International Preliminary Report on Patentability, mailed Aug. 18, 2015, 7 pages.
International Application No. PCT/IB2014/0558760 filed Feb. 3, 2014, International Search Report and Written Opinion, mailed Mar. 13, 2014, 10 pages.

\* cited by examiner

HEXAHYDROPYRANO[3,4-D][1,3]THIAZIN-2-AMINE COMPOUNDS

This application is a Continuation Patent Application of U.S. patent application Ser. No. 13/596,208, filed on Aug. 28, 2012, which claims benefit of U.S. Provisional Patent Application No. 61/529,367, filed on Aug. 31, 2011, the disclosure of which is hereby incorporated by reference in its entirety.

FIELD OF THE INVENTION

The present inventions relate to small molecule inhibitors of β-site amyloid precursor protein (APP) Cleaving Enzyme 1 (BACE 1) and its pharmaceutically acceptable salts. This invention relates to inhibiting, in mammals, including humans, the production of A-beta peptides that can contribute to the formation of neurological deposits of amyloid protein. The present invention also relates to the treatment of Alzheimer's Disease (AD) and other neurodegenerative and/or neurological disorders in mammals, including humans. More particularly, this invention relates to thioamidine compounds useful for the treatment of neurodegenerative and/or neurological disorders, such as AD and Down's Syndrome, related to A-beta peptide production.

BACKGROUND OF THE INVENTION

Dementia results from a wide variety of distinctive pathological processes. The most common pathological processes causing dementia are AD, cerebral amyloid angiopathy (CM) and prion-mediated diseases (see, e.g., Haan et al., Clin. Neurol. Neurosurg. 1990, 92(4):305-310; Glenner et al., J. Neurol. Sci. 1989, 94:1-28). AD is a progressive, neurodegenerative disorder characterized by memory impairment and cognitive dysfunction. AD affects nearly half of all people past the age of 85, the most rapidly growing portion of the United States population. As such, the number of AD patients in the United States is expected to increase from about 4 million to about 14 million by 2050.

Aminodihydrothiazine or thioamidine compounds are described in WO 2010/038686 as useful inhibitors of the β-secretase enzyme. Described therein are also certain compounds that are intermediates to the aminodihydrothiazine compounds. Surprisingly, Applicants determined that at least some of these intermediates are brain-penetrable BACE inhibitors and as such would be expected to be BACE inhibitors and modulators for the treatment of AD and other neurodegenerative diseases (see Olsen et al., Ann. Rep. Med. Chem. 2007, 42:27-47). Accordingly, the present invention is directed to the use of these compounds in the treatment of neurodegenerative diseases, including AD. The invention is also directed to novel thioamidine compounds and their use in the treatment of neurodegenerative diseases, including AD.

SUMMARY OF THE INVENTION

The invention is directed to compounds, including pharmaceutically acceptable salts thereof, having the structure of formula I:

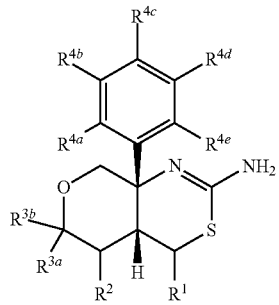

wherein $R^1$ is hydrogen, $C_{1-6}$alkyl, $C_{2-6}$alkenyl or —$(C(R^{5a}R^{5b}))_m$ $(C_{3-6}$cycloalkyl); wherein said alkyl, alkenyl or cycloalkyl moieties may independently be optionally substituted with one to three $R^6$;

$R^2$ is halogen, hydrogen, $C_{1-6}$alkyl, $C_{2-6}$alkenyl or —$(C(R^{5a}R^{5b}))_m$—$(C_{3-6}$cycloalkyl); wherein said alkyl, alkenyl or cycloalkyl moieties may independently be optionally substituted with one to three $R^6$;

$R^{3a}$ is hydrogen, $C_{1-6}$alkyl, $C_{2-6}$alkenyl, —$(C(R^{5a}R^{5b}))_m$ $(C_{3-6}$cycloalkyl), —$(C(R^{5a}R^{5b}))_m$-(4- to 10-membered heterocycloalkyl), —$(C(R^{5a}R^{5b}))_m$—$(C_{6-10}$aryl), —$(C(R^{5a}R^{5b}))_m$-(5- to 10-membered heteroaryl), —$(C(R^{5a}R^{5b}))_m$—$OR^7$, —$C(O)N(R^8)_2$, —$(C(R^{5a}R^{5b}))_n$—NHC(O)$R^8$ or —$(C(R^{5a}R^{5b}))_n$—$N(R^8)_2$; wherein said alkyl, alkenyl, cycloalkyl or heterocycloalkyl moieties may independently be optionally substituted with one to three $R^{10}$; and wherein the aryl or heteroaryl moieties may independently be optionally substituted with one to five $R^{10}$;

$R^{3b}$ is hydrogen, $C_{1-3}$alkyl, —$(C(R^{5a}R^{5b}))_m$—$(C_{3-6}$cycloalkyl), —$(C(R^{5a}R^{5b}))_m$-(4- to 5-membered heterocycloalkyl) or —$(C(R^{5a}R^{5b}))_m$—$OR^7$; wherein said alkyl, cycloalkyl or heterocycloalkyl moieties may independently be optionally substituted with one to three $R^{10}$;

$R^{4a}$ and $R^{4e}$ are independently halogen, hydrogen, $C_{1-6}$alkyl, —CN or —$OR^9$; wherein said alkyl is optionally substituted by one to three fluoro;

$R^{4b}$ and $R^{4d}$ are independently fluoro, chloro, hydrogen, $C_{1-6}$alkyl, —CN or —$OR^{12}$; wherein said alkyl is optionally substituted by one to three fluoro; or $R^{4c}$ and $R^{4d}$, together with the carbons to which they are bonded, form a 5- to 6-membered cycloalkyl or a 6-membered aryl, wherein said cycloalkyl or aryl is optionally substituted with one to three —$CF_3$, fluoro, $C_{1-6}$alkyl, —$OC_{1-6}$alkyl, —OH, —$NH_2$ or —NH—$C_{1-6}$alkyl;

$R^{4c}$ is halogen, hydrogen, $C_{1-6}$alkyl, —CN or —$OR^{12}$; wherein said alkyl is optionally substituted by one to three fluoro; or $R^{4b}$ and $R^{4c}$, together with the carbons to which they are bonded, form a 5- to 6-membered cycloalkyl or a 6-membered aryl, wherein said cycloalkyl or aryl is optionally substituted with one to three —$CF_3$, fluoro, $C_{1-6}$alkyl, —$OC_{1-6}$alkyl, —OH, —$NH_2$ or —NH—$C_{1-6}$alkyl;

$R^{5a}$ and $R^{5b}$ are each independently fluoro, hydrogen or $C_{1-6}$alkyl;

$R^6$ is independently fluoro, —CN, $C_{1-6}$alkyl or $OR^9$;

$R^7$ is independently hydrogen, $C_{1-6}$alkyl, —$(C(R^{5a}R^{5b}))_t$ —$(C_{3-6}$cycloalkyl), —$(C(R^{5a}R^{5b}))_t$-(4- to 10-membered heterocycloalkyl), —$(C(R^{5a}R^{5b}))_t$—$(C_{6-10}$aryl), —$(C(R^{5a}R^{5b}))_t$-(5- to 10-membered heteroaryl) or —$C(O)R^{11}$; wherein said alkyl, cycloalkyl, heterocycloalkyl, aryl and heteroaryl are optionally substituted with one to three $R^{10}$;

R[8] is independently hydrogen, $C_{1-6}$alkyl, —(C($R^{5a}R^{5b}$))$_t$—($C_{3-6}$cycloalkyl), —(C($R^{5a}R^{5b}$))$_t$-(4- to 10-membered heterocycloalkyl), —(C($R^{5a}R^{5b}$))$_t$—($C_{6-10}$aryl) or —(C($R^{5a}R^{5b}$))$_t$-(5- to 10-membered heteroaryl), wherein said alkyl, cycloalkyl, heterocycloalkyl, aryl and heteroaryl are optionally substituted with one to three fluoro;

$R^9$ is independently hydrogen, $C_{1-6}$alkyl or $C_{3-6}$alkenyl, optionally substituted with one to three fluoro;

$R^{10}$ is independently halogen, —OH, —CN, $C_{1-6}$alkyl or —O$C_{1-6}$alkyl; wherein said alkyl groups are optionally substituted with one to three fluoro;

$R^{11}$ is independently $C_{6-10}$aryl, $C_{1-6}$alkyl or —NR$^{13a}$R$^{13b}$;

$R^{12}$ is hydrogen or $C_{1-6}$alkyl optionally substituted with one to three fluoro;

$R^{13a}$ and $R^{13b}$ are each independently hydrogen, $C_{1-6}$alkyl, wherein said alkyl is optionally substituted with one to three fluoro; or $R^{13a}$ and $R^{13b}$ taken together with the nitrogen to which they are bonded form a 4- to 6-membered heterocycloalkyl ring, which may optionally include one oxygen to form a morpholine moiety;

m is 0, 1 or 2;
n is 1 or 2; and
t is 0 or 1;

with the provisos that:
(i) if one of $R^{4a}$ or $R^{4e}$ is fluoro, while the other is hydrogen, and $R^1$, $R^2$, $R^{4b}$, $R^{4c}$ and $R^{4d}$ are hydrogen, and one of $R^{3a}$ or $R^{3b}$ is hydrogen, methyl, —CH$_2$OCH$_3$, —CH$_2$OCH$_2$-phenyl or —CH$_2$OH, then the other ($R^{3a}$ or $R^{3b}$) cannot be hydrogen;

(ii) if one of $R^{4a}$ or $R^{4e}$ is fluoro, while the other is hydrogen, and $R^{3a}$, $R^{3b}$, $R^{4b}$, $R^{4c}$ and $R^{4d}$ are hydrogen, and $R^2$ is fluoro, —CH$_3$ or —OCH$_3$, $R^1$ cannot be hydrogen; and (iii) if one of $R^{4a}$ or $R^{4e}$ is fluoro, while the other is hydrogen, and if $R^2$, $R^{3a}$, $R^{3b}$, $R^{4b}$, $R^{4c}$ and $R^{4d}$ are hydrogen, $R^1$ cannot be methyl; and (iv) if one of $R^{4a}$ or $R^{4e}$ is —OR$^9$, wherein $R^9$ is —CF$_3$, while the other is hydrogen, and if $R^{4b}$, $R^{4c}$ and $R^{4d}$ are hydrogen, then at least one of $R^1$, $R^2$ or $R^{3a}$, $R^{3b}$, cannot be hydrogen.

or a pharmaceutically acceptable salt or solvate thereof.

In another aspect, the invention is represented by compounds of formula I-a

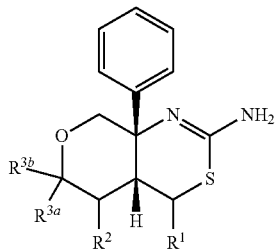

I-a wherein
$R^1$ is hydrogen, $C_{1-6}$alkyl, $C_{2-6}$alkenyl or —(C($R^{5a}R^{5b}$))$_m$—($C_{3-6}$cycloalkyl); wherein said alkyl, alkenyl or cycloalkyl moieties may independently be optionally substituted with one to three $R^6$;

$R^2$ is halogen, hydrogen, $C_{1-6}$alkyl, $C_{2-6}$alkenyl or —(C($R^{5a}R^{5b}$))$_m$—($C_{3-6}$cycloalkyl); wherein said alkyl, alkenyl or cycloalkyl moieties may independently be optionally substituted with one to three $R^6$;

$R^{3a}$ is hydrogen, $C_{1-6}$alkyl, $C_{2-6}$alkenyl, —(C($R^{5a}R^{5b}$))$_m$—($C_{3-6}$cycloalkyl), —(C($R^{5a}R^{5b}$))$_m$-(4- to 10-membered heterocycloalkyl), —(C($R^{5a}R^{5b}$))$_m$—($C_{6-10}$aryl), —(C($R^{5a}R^{5b}$))$_m$-(5- to 10-membered heteroaryl), —(C($R^{5a}R^{5b}$))$_m$—OR$^7$, —C(O)N($R^8$)$_2$, —(C($R^{5a}R^{5b}$))$_n$—NHC(O)R$^8$ or —(C($R^{5a}R^{5b}$))$_n$—N($R^8$)$_2$; wherein said alkyl, alkenyl, cycloalkyl or heterocycloalkyl moieties may independently be optionally substituted with one to three $R^{10}$; and wherein the aryl or heteroaryl moieties may independently be optionally substituted with one to five $R^{10}$;

$R^{3b}$ is hydrogen, $C_{1-3}$alkyl, —(C($R^{5a}R^{5b}$))$_m$—($C_{3-5}$cycloalkyl), —(C($R^{5a}R^{5b}$))$_m$-(4- to 5-membered heterocycloalkyl) or —(C($R^{5a}R^{5b}$))$_m$—OR$^7$; wherein said alkyl, cycloalkyl or heterocycloalkyl moieties may independently be optionally substituted with one to three $R^{10}$;

$R^{5a}$ and $R^{5b}$ are each independently fluoro, hydrogen, $C_{1-6}$alkyl;

$R^6$ is independently fluoro, —CN, $C_{1-6}$alkyl or OR$^9$;

$R^7$ is independently hydrogen, $C_{1-6}$alkyl, —(C($R^{5a}R^{5b}$))$_t$—($C_{3-6}$cycloalkyl), —(C($R^{5a}R^{5b}$))$_t$-(4- to 10-membered heterocycloalkyl), —(C($R^{5a}R^{5b}$))$_t$—($C_{6-10}$aryl), —(C($R^{5a}R^{5b}$))$_t$-(5- to 10-membered heteroaryl) or —C(O)R$^{11}$; wherein said alkyl, cycloalkyl, heterocycloalkyl, aryl and heteroaryl are optionally substituted with one to three $R^{10}$;

$R^8$ is independently hydrogen, $C_{1-6}$alkyl, —(C($R^{5a}R^{5b}$))$_t$—($C_{3-6}$cycloalkyl), —(C($R^{5a}R^{5b}$))$_t$-(4- to 10-membered heterocycloalkyl), —(C($R^{5a}R^{5b}$))$_t$—($C_{6-10}$aryl) or —(C($R^{5a}R^{5b}$))$_t$-(5- to 10-membered heteroaryl), wherein said alkyl, cycloalkyl, heterocycloalkyl, aryl and heteroaryl are optionally substituted with one to three fluoro;

$R^9$ is independently hydrogen, $C_{1-6}$alkyl or $C_{3-6}$alkenyl, optionally substituted with one to three fluoro;

$R^{10}$ is independently halogen, —OH, —CN, $C_{1-6}$alkyl or —O$C_{1-6}$alkyl; wherein said alkyl groups are optionally substituted with one to three fluoro;

$R^{11}$ is independently $C_{6-10}$aryl, $C_{1-6}$alkyl or —NR$^{13a}$R$^{13b}$;

$R^{12}$ is hydrogen or $C_{1-6}$alkyl optionally substituted with one to three fluoro;

$R^{13a}$ and $R^{13b}$ are each independently hydrogen, $C_{1-6}$alkyl, wherein said alkyl is optionally substituted with one to three fluoro; or $R^{13a}$ and $R^{13b}$ taken together with the nitrogen to which they are bonded form a 4- to 6-membered heterocycloalkyl ring, which may optionally include one oxygen to form a morpholine moiety;

m is 0, 1 or 2;
n is 1 or 2; and
t is 0 or 1;

or a pharmaceutically acceptable salt or solvate thereof.

In another aspect, the invention is represented by compounds of formula (I-b)

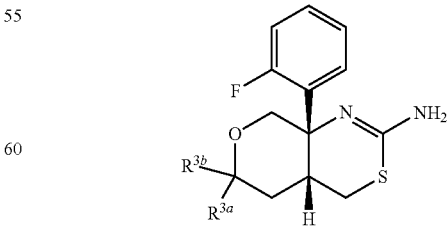

I-b wherein
$R^{3a}$ is methyl (substituted with at least one halogen), $C_{2-6}$alkyl, $C_{2-6}$alkenyl, —(C($R^{5a}R^{5b}$))$_m$—($C_{3-6}$cycloalkyl), —C(R$^{5a}$R$^{5b}$))$_m$-(4- to 10-membered heterocycloalkyl), —(C(R$^{5a}$R$^{5b}$))$_m$—(C$_{6-10}$aryl), —(C(R$^{5a}$R$^{5b}$))$_m$-(5- to 10-membered heteroaryl), —OR$^{7a}$, —CH$_2$—OR$^{7b}$, —(C(R$^{5a}$R$^{5b}$))$_q$—OR$^{7c}$, —C(O)N(R$^8$)$_2$, —(C(R$^{5a}$R$^{5b}$))$_n$—NHC(O)R$^8$ or —(C(R$^{5a}$R$^{5b}$))$_n$—N(R$^8$)$_2$; wherein said alkyl, alkenyl, cycloalkyl or heterocycloalkyl moieties may independently be optionally substituted with one to three R$^{10}$; and wherein the aryl or heteroaryl moieties may independently be optionally substituted with one to five R$^{10}$;

R$^{3b}$ is hydrogen, C$_{1-3}$alkyl, —(C(R$^{5a}$R$^{5b}$))$_m$—(C$_{3-6}$cycloalkyl), —(C(R$^{5a}$R$^{5b}$))$_m$-(4- to 5-membered heterocycloalkyl) or —(C(R$^{5a}$R$^{5b}$))$_m$—OR$^7$; wherein said alkyl, cycloalkyl or heterocycloalkyl moieties may independently be optionally substituted with one to three R$^{10}$;

R$^{5a}$ and R$^{5b}$ are each independently fluoro, hydrogen or C$_{1-6}$alkyl;

R$^6$ is independently fluoro, —CN, C$_{1-6}$alkyl or OR$^9$;

R$^{7a}$ is hydrogen, C$_{1-6}$alkyl, —(C(R$^{5a}$R$^{5b}$))$_t$—(C$_{3-6}$cycloalkyl), —(C(R$^{5a}$R$^{5b}$))$_t$-(4- to 10-membered heterocycloalkyl), —(C(R$^{5a}$R$^{5b}$))$_t$—(C$_{6-10}$aryl), —(C(R$^{5a}$R$^{5b}$))$_t$-(5- to 10-membered heteroaryl) or —C(O); wherein said alkyl, cycloalkyl, heterocycloalkyl, aryl and heteroaryl moieties are optionally substituted with one to three R$^{10}$;

R$^{7b}$ is C$_{2-6}$alkyl, —(C(R$^{5a}$R$^{5b}$))$_t$—(C$_{3-6}$cycloalkyl), —(C(R$^{5a}$R$^{5b}$))$_t$-(4- to 10-membered heterocycloalkyl), —C$_{6-10}$aryl, —(C(R$^{5a}$R$^{5b}$))$_q$—(C$_{6-10}$aryl), —(C(R$^{5a}$R$^{5b}$))$_t$-(5- to 10-membered heteroaryl) or —C(O)R$^{11}$; wherein said alkyl, cycloalkyl, heterocycloalkyl, aryl and heteroaryl moieties are optionally substituted with one to three R$^{10}$;

R$^{7c}$ is hydrogen, C$_{1-6}$alkyl, —(C(R$^{5a}$R$^{5b}$))$_t$—(C$_{3-6}$cycloalkyl), —(C(R$^{5a}$R$^{5b}$))$_t$-(4- to 10-membered heterocycloalkyl), —(C(R$^{5a}$R$^{5b}$))$_t$—(C$_{6-10}$aryl), —(C(R$^{5a}$R$^{5b}$))$_t$-(5- to 10-membered heteroaryl) or —C(O)R$^{11}$; wherein said alkyl, cycloalkyl, heterocycloalkyl, aryl and heteroaryl moieties are optionally substituted with one to three R$^{10}$;

R$^8$ is independently hydrogen, C$_{1-6}$alkyl, —(C(R$^{5a}$R$^{5b}$))$_t$—(C$_{3-6}$cycloalkyl), —(C(R$^{5a}$R$^{5b}$))$_t$-(4- to 10-membered heterocycloalkyl), —(C(R$^{5a}$R$^{5b}$))$_t$—(C$_{6-10}$aryl) or —(C(R$^{5a}$R$^{5b}$))$_t$-(5- to 10-membered heteroaryl), wherein said alkyl, cycloalkyl, heterocycloalkyl, aryl and heteroaryl moieties are optionally substituted with one to three fluoro;

R$^9$ is independently hydrogen or C$_{1-6}$alkyl, wherein said alkyl is optionally substituted with one to three fluoro;

R$^{10}$ is independently halogen, —OH, —CN, C$_{1-6}$alkyl or —OC$_{1-6}$alkyl; wherein said alkyl groups are optionally substituted with one to three fluoro;

R$^{11}$ is independently C$_{6-10}$aryl, C$_{1-6}$alkyl or —NR$^{13a}$R$^{13b}$;

R$^{12}$ is hydrogen or C$_{1-6}$alkyl optionally substituted with one to three fluoro;

R$^{13a}$ and R$^{13b}$ are each independently hydrogen, C$_{1-6}$alkyl, wherein said alkyl is optionally substituted with one to three fluoro; or R$^{13a}$ and R$^{13b}$ taken together with the nitrogen to which they are bonded form a 4- to 6-membered heterocycloalkyl ring, which may optionally include one oxygen to form a morpholine moiety;

m is 0, 1 or 2;

n is 1, 2 or 3;

q is 2 or 3; and t is 0 or 1;

or a pharmaceutically acceptable salt or solvate thereof.

In preferred embodiments, R$^{3a}$ is methyl (substituted with one to three fluoro) or —CH$_2$—OR$^{7b}$, wherein R$^{7b}$ is C$_{2-6}$alkyl, —C$_{6-10}$aryl, —(C(R$^{5a}$R$^{5b}$))$_t$-(5- to 10-membered heteroaryl) or —C(O)R$^{11}$; wherein said alkyl, aryl and heteroaryl moieties are optionally substituted with one to three R$^{10}$; and R$^{3b}$ is hydrogen; or a pharmaceutically acceptable salt or solvate thereof.

In another aspect, the invention is represented by compounds of formula (I-c)

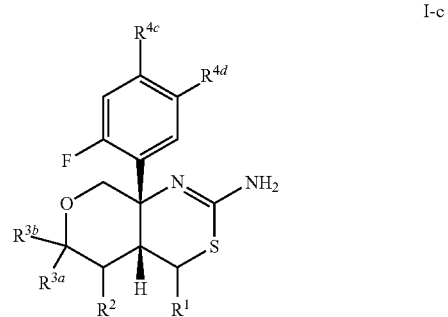

I-c wherein

R$^1$ is hydrogen, C$_{1-6}$alkyl, C$_{2-6}$alkenyl or —(C(R$^{5a}$R$^{5b}$))$_m$—(C$_{3-6}$cycloalkyl); wherein said alkyl, alkenyl or cycloalkyl moieties may independently be optionally substituted with one to three R$^6$;

R$^2$ is halogen, hydrogen, C$_{1-6}$alkyl, C$_{2-6}$alkenyl or —(C(R$^{5a}$R$^{5b}$))$_m$—(C$_{3-6}$cycloalkyl); wherein said alkyl, alkenyl or cycloalkyl moieties may independently be optionally substituted with one to three R$^6$;

R$^{3a}$ is hydrogen, C$_{1-6}$alkyl, C$_{2-6}$alkenyl, —(C(R$^{5a}$R$^{5b}$))$_m$—(C$_{3-6}$cycloalkyl), —(C(R$^{5a}$R$^{5b}$))$_m$-(4- to 10-membered heterocycloalkyl), —(C(R$^{5a}$R$^{5b}$))$_m$—(C$_{6-10}$aryl), —(C(R$^{5a}$R$^{5b}$))$_m$-(5- to 10-membered heteroaryl), —(C(R$^{5a}$R$^{5b}$))$_m$—OR$^7$, —C(O)N(R$^8$)$_2$, —(C(R$^{5a}$R$^{5b}$))$_n$—NHC(O)R$^8$ or —(C(R$^{5a}$R$^{5b}$))$_n$—N(R$^8$)$_2$; wherein said alkyl, alkenyl, cycloalkyl or heterocycloalkyl moieties may independently be optionally substituted with one to three R$^{10}$; and wherein the aryl or heteroaryl moieties may independently be optionally substituted with one to five R$^{10}$;

R$^{3b}$ is hydrogen, C$_{1-3}$alkyl, —(C(R$^{5a}$R$^{5b}$))$_m$—(C$_{3-5}$cycloalkyl), —(C(R$^{5a}$R$^{5b}$))$_m$-(4- to 5-membered heterocycloalkyl) or —(C(R$^{5a}$R$^{5b}$))$_m$—OR$^7$; wherein said alkyl, cycloalkyl or heterocycloalkyl moieties may independently be optionally substituted with one to three R$^{10}$;

R$^{4c}$ is halogen, C$_{1-6}$alkyl, —CN or —OR$^9$; wherein said alkyl is optionally substituted by one to three fluoro;

R$^{4d}$ is halogen, hydrogen, C$_{1-6}$alkyl, —CN or —OR$^{12}$; wherein said alkyl is optionally substituted by one to three fluoro; or R$^{4c}$ and R$^{4d}$, together with the carbons to which they are bonded, form a 5- to 6-membered cycloalkyl or a 6-membered aryl, wherein said cycloalkyl or aryl is optionally substituted with one to three —CF$_3$, fluoro, C$_{1-6}$alkyl, —OC$_{1-6}$alkyl, —OH, —NH$_2$ or —NH—C$_{1-6}$alkyl;

R$^{5a}$ and R$^{5b}$ are each independently fluoro, hydrogen or C$_{1-6}$alkyl;

R$^6$ is independently fluoro, —CN, C$_{1-6}$alkyl or OR$^9$;

R$^7$ is independently hydrogen, C$_{1-6}$alkyl, —(C(R$^{5a}$R$^{5b}$))$_t$—(C$_{3-6}$cycloalkyl), —(C(R$^{5a}$R$^{5b}$))$_t$-(4- to 10-membered heterocycloalkyl), —(C(R$^{5a}$R$^{5b}$))$_t$—(C$_{6-10}$aryl), —(C(R$^{5a}$R$^{5b}$))$_t$-(5- to 10-membered heteroaryl) or —C(O)R$^{11}$; wherein said alkyl, cycloalkyl, heterocycloalkyl, aryl and heteroaryl moieties are optionally substituted with one to three R$^{10}$;

R$^8$ is independently hydrogen, C$_{1-6}$alkyl, —(C(R$^{5a}$R$^{5b}$))$_t$—(C$_{3-6}$cycloalkyl), —(C(R$^{5a}$R$^{5b}$))$_t$-(4- to 10-membered heterocycloalkyl), —(C(R$^{5a}$R$^{5b}$))$_t$—(C$_{6-10}$aryl) or —(C(R$^{5a}$R$^{5b}$))$_t$-(5- to 10-membered heteroaryl), wherein said alkyl, cycloalkyl, heterocycloalkyl, aryl and heteroaryl moieties are optionally substituted with one to three fluoro;

$R^9$ is independently hydrogen, $C_{1-6}$alkyl or $C_{3-6}$alkenyl, optionally substituted with one to three fluoro;

$R^{10}$ is independently halogen, —OH, —CN, $C_{1-6}$alkyl, —O$C_{1-6}$alkyl; wherein said alkyl is optionally substituted with one to three fluoro;

$R^{11}$ is independently $C_{6-10}$aryl, $C_{1-6}$alkyl or —N$R^{13a}R^{13b}$;

$R^{12}$ is hydrogen or $C_{1-6}$alkyl optionally substituted with one to three fluoro;

$R^{13a}$ and $R^{13b}$ are each independently hydrogen, $C_{1-6}$alkyl, wherein said alkyl is optionally substituted with one to three fluoro; or $R^{13a}$ and $R^{13b}$ taken together with the nitrogen to which they are bonded form a 4- to 6-membered heterocycloalkyl ring, which may optionally include one oxygen to form a morpholine moiety;

m is 0, 1 or 2;
n is 1 or 2; and
t is 0 or 1;

or a pharmaceutically acceptable salt or solvate thereof.

In another embodiment, $R^{4c}$ is fluoro, chloro, methyl or —O$R^9$, wherein $R^9$ is hydrogen or $C_{1-6}$alkyl. In another embodiment, $R^{4d}$ is hydrogen; or a pharmaceutically acceptable salt or solvate thereof. In another embodiment, $R^1$ and $R^2$ are independently hydrogen or methyl; $R^{3a}$ is hydrogen, $C_{1-6}$alkyl; —(C($R^{5a}R^{5b}$))$_m$—($C_{6-10}$aryl) or —(C($R^{5a}R^{5b}$))$_m$—O$R^7$; wherein said alkyl moiety may independently be optionally substituted with one to three $R^{10}$; and wherein the aryl moiety may independently be optionally substituted with one to five $R^{10}$; $R^{3b}$ is hydrogen; and $R^{4c}$ is chloro, fluoro, hydroxyl or methyl.

In another aspect, the invention is directed to compounds of formula (I-d)

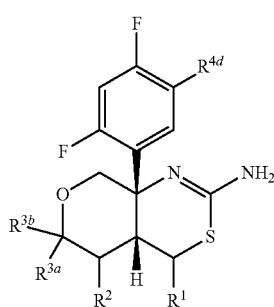

I-d wherein $R^1$ is hydrogen, $C_{1-6}$alkyl, $C_{2-6}$alkenyl or —(C($R^{5a}R^{5b}$))$_m$—($C_{3-6}$cycloalkyl); wherein said alkyl, alkenyl or cycloalkyl moieties may independently be optionally substituted with one to three $R^6$;

$R^2$ is halogen, hydrogen, $C_{1-6}$alkyl, $C_{2-6}$alkenyl or —(C($R^{5a}R^{5b}$))$_m$—($C_{3-6}$cycloalkyl); wherein said alkyl, alkenyl or cycloalkyl moieties may independently be optionally substituted with one to three $R^6$;

$R^{3a}$ is hydrogen, $C_{1-6}$alkyl, $C_{2-6}$alkenyl, —(C($R^{5a}R^{5b}$))$_m$—($C_{3-6}$cycloalkyl), —(C($R^{5a}R^{5b}$))$_m$-(4- to 10-membered heterocycloalkyl), —(C($R^{5a}R^{5b}$))$_m$—($C_{6-10}$aryl), —(C($R^{5a}R^{5b}$))$_m$-(5- to 10-membered heteroaryl), —(C($R^{5a}R^{5b}$))$_m$—O$R^7$, —C(O)N($R^8$)$_2$, —(C($R^{5a}R^{5b}$))$_n$—NHC(O)$R^8$ or —(C($R^{5a}R^{5b}$))$_n$—N($R^8$)$_2$; wherein said alkyl, alkenyl, cycloalkyl or heterocycloalkyl moieties may independently be optionally substituted with one to three $R^{10}$;

and wherein the aryl or heteroaryl moieties may independently be optionally substituted with one to five $R^{10}$;

$R^{3b}$ is hydrogen, $C_{1-3}$alkyl, —(C($R^{5a}R^{5b}$))$_m$—($C_{3-5}$cycloalkyl), —(C($R^{5a}R^{5b}$))$_m$-(4- to 5-membered heterocycloalkyl) or —(C($R^{5a}R^{5b}$))$_m$—O$R^7$; wherein said alkyl, cycloalkyl or heterocycloalkyl moieties may independently be optionally substituted with one to three $R^{10}$;

$R^{4d}$ is halogen, hydrogen, $C_{1-6}$alkyl, —CN or —O$R^{12}$; wherein said alkyl is optionally substituted by one to three fluoro; or $R^{4c}$ and $R^{4d}$, together with the carbons to which they are bonded, form a 5- to 6-membered cycloalkyl or a 6-membered aryl, wherein said cycloalkyl or aryl is optionally substituted with one to three —CF$_3$, fluoro, $C_{1-6}$alkyl, —O$C_{1-6}$alkyl, —OH, —NH$_2$ or —NH—$C_{1-6}$alkyl;

$R^{5a}$ and $R^{5b}$ are each independently fluoro, hydrogen or $C_{1-6}$alkyl;

$R^6$ is independently fluoro, —CN, $C_{1-6}$alkyl or O$R^9$;

$R^7$ is independently hydrogen, $C_{1-6}$alkyl, —(C($R^{5a}R^{5b}$))$_t$—($C_{3-6}$cycloalkyl), —(C($R^{5a}R^{5b}$))$_t$-(4- to 10-membered heterocycloalkyl), —(C($R^{5a}R^{5b}$))$_t$—($C_{6-10}$aryl), —(C($R^{5a}R^{5b}$))$_t$-(5- to 10-membered heteroaryl) or —C(O)$R^{11}$; wherein said alkyl, cycloalkyl, heterocycloalkyl, aryl and heteroaryl moieties are optionally substituted with one to three $R^{10}$;

$R^8$ is independently hydrogen, $C_{1-6}$alkyl, —(C($R^{5a}R^{5b}$))$_t$—($C_{3-6}$cycloalkyl), —(C($R^{5a}R^{5b}$))$_t$-(4- to 10-membered heterocycloalkyl), —(C($R^{5a}R^{5b}$))$_t$—($C_{6-10}$aryl) or —(C($R^{5a}R^{5b}$))$_t$-(5- to 10-membered heteroaryl), wherein said alkyl, cycloalkyl, heterocycloalkyl, aryl and heteroaryl moieties are optionally substituted with one to three fluoro;

$R^9$ is independently hydrogen, $C_{1-6}$alkyl or $C_{3-6}$alkenyl, optionally substituted with one to three fluoro;

$R^{10}$ is independently halogen, —OH, —CN, $C_{1-6}$alkyl, —O$C_{1-6}$alkyl; wherein said alkyl is optionally substituted with one to three fluoro;

$R^{11}$ is independently $C_{6-10}$aryl, $C_{1-6}$alkyl or —N$R^{13a}R^{13b}$;

$R^{12}$ is hydrogen or $C_{1-6}$alkyl optionally substituted with one to three fluoro;

$R^{13a}$ and $R^{13b}$ are each independently hydrogen, $C_{1-6}$alkyl, wherein said alkyl is optionally substituted with one to three fluoro; or $R^{13a}$ and $R^{13b}$ taken together with the nitrogen to which they are bonded form a 4- to 6-membered heterocycloalkyl ring, which may optionally include one oxygen to form a morpholine moiety;

m is 0, 1 or 2;
n is 1 or 2; and
t is 0 or 1;

or a pharmaceutically acceptable salt or solvate thereof.

In another embodiment, $R^1$ is hydrogen or $C_{1-6}$alkyl and in another embodiment, $R^{3a}$ is hydrogen, $C_{1-6}$alkyl or —(C($R^{5a}R^{5b}$))$_m$—O$R^7$.

In another aspect, the invention is directed to compounds of formula (I-e)

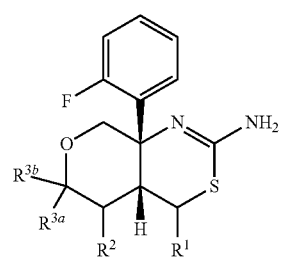

I-e wherein

R¹ is hydrogen, $C_{1-6}$alkyl, $C_{2-6}$alkenyl or —$(C(R^{5a}R^{5b}))_m$—$(C_{3-6}$cycloalkyl); wherein said alkyl, alkenyl or cycloalkyl moieties may independently be optionally substituted with one to three $R^6$;

R² is halogen, hydrogen, $C_{1-6}$alkyl, $C_{2-6}$alkenyl or —$(C(R^{5a}R^{5b}))_m$—$(C_{3-6}$cycloalkyl); wherein said alkyl, alkenyl or cycloalkyl moieties may independently be optionally substituted with one to three $R^6$; provided that both $R^1$ and $R^2$ are not hydrogen;

$R^{3a}$ is $C_{1-6}$alkyl, $C_{2-6}$alkenyl, —$(C(R^{5a}R^{5b}))_m$—$(C_{3-6}$cycloalkyl), —$(C(R^{5a}R^{5b}))_m$-(4- to 10-membered heterocycloalkyl), —$(C(R^{5a}R^{5b}))_m$—$(C_{6-10}$aryl), —$(C(R^{5a}R^{5b}))_m$-(5- to 10-membered heteroaryl), —$(C(R^{5a}R^{5b}))_m$—$OR^7$, —$C(O)N(R^8)_2$, —$(C(R^{5a}R^{5b}))_n$—$NHC(O)R^8$ or —$(C(R^{5a}R^{5b}))_n$—$N(R^8)_2$; wherein said alkyl, alkenyl, cycloalkyl or heterocycloalkyl moieties may independently be optionally substituted with one to three $R^{10}$; and wherein the aryl or heteroaryl moieties may independently be optionally substituted with one to five $R^{10}$;

$R^{3b}$ is hydrogen, $C_{1-3}$alkyl, —$(C(R^{5a}R^{5b}))_m$—$(C_{3-5}$cycloalkyl), —$(C(R^{5a}R^{5b}))_m$-(4- to 5-membered heterocycloalkyl) or —$(C(R^{5a}R^{5b}))_m$—$OR^7$; wherein said alkyl, cycloalkyl or heterocycloalkyl moieties may independently be optionally substituted with one to three $R^{10}$;

$R^{5a}$ and $R^{5b}$ are each independently fluoro, hydrogen or $C_{1-6}$alkyl;

$R^6$ is fluoro, —CN, $C_{1-6}$alkyl or $OR^9$;

$R^7$ is independently hydrogen, $C_{1-6}$alkyl, —$(C(R^{5a}R^{5b}))_t$—$(C_{3-6}$cycloalkyl), —$(C(R^{5a}R^{5b}))_t$-(4- to 10-membered heterocycloalkyl), —$(C(R^{5a}R^{5b}))_t$—$(C_{6-10}$aryl), —$(C(R^{5a}R^{5b}))_t$-(5- to 10-membered heteroaryl) or —$C(O)R^{11}$; wherein said alkyl, cycloalkyl, heterocycloalkyl, aryl and heteroaryl are optionally substituted with one to three $R^{10}$;

$R^8$ is independently hydrogen, $C_{1-6}$alkyl, —$(C(R^{5a}R^{5b}))_t$—$(C_{3-6}$cycloalkyl), —$(C(R^{5a}R^{5b}))_t$-(4- to 10-membered heterocycloalkyl), —$(C(R^{5a}R^{5b}))_t$—$(C_{6-10}$aryl) or —$(C(R^{5a}R^{5b}))_t$-(5- to 10-membered heteroaryl), wherein said alkyl, cycloalkyl, heterocycloalkyl, aryl and heteroaryl are optionally substituted with one to three fluoro;

$R^9$ is independently hydrogen, $C_{1-6}$alkyl or $C_{3-6}$alkenyl, optionally substituted with one to three fluoro;

$R^{10}$ is independently halogen, —OH, —CN, $C_{1-6}$alkyl, —$OC_{1-6}$alkyl; wherein said alkyl is optionally substituted with one to three fluoro;

$R^{11}$ is independently $C_{6-10}$aryl, $C_{1-6}$alkyl or —$NR^{13a}R^{13b}$;

$R^{12}$ is hydrogen or $C_{1-6}$alkyl optionally substituted with one to three fluoro;

$R^{13a}$ and $R^{13b}$ are each independently hydrogen, $C_{1-6}$alkyl, wherein said alkyl is optionally substituted with one to three fluoro; or $R^{13a}$ and $R^{13b}$ taken together with the nitrogen to which they are bonded form a 4- to 6-membered heterocycloalkyl ring, which may optionally include one oxygen to form a morpholine moiety;

m is 0, 1 or 2;

n is 1 or 2; and t is 0 or 1;

or a pharmaceutically acceptable salt or solvate thereof.

In another embodiment of the compound of formula 1-e, $R^1$ and $R^2$ are independently hydrogen or $C_{1-6}$alkyl.

In preferred embodiments, the invention is directed to:

(4aR,6R,8aS)-6-[(benzyloxy)methyl]-8a-(2,4-difluorophenyl)-4,4-a,5,6,8,8a-hexahydropyrano[3,4-d][1,3]thiazin-2-amine;

(4aR,8aS)-8a-(2,4-difluorophenyl)-4,4-a,5,6,8,8a-hexahydropyrano[3,4-d][1,3]thiazin-2-amine;

(4aR,8aS)-8a-(2-fluoro-4-methylphenyl)-4,4-a,5,6,8,8a-hexahydropyrano[3,4-d][1,3]thiazin-2-amine;

(4aR,8aS)-8a-(4-chloro-2-fluorophenyl)-4,4-a,5,6,8,8a-hexahydropyrano[3,4-d][1,3]thiazin-2-amine;

4-[(4aR,8aS)-2-amino-4,4-a,5,6-tetrahydropyrano[3,4-d][1,3]thiazin-8a(8H)-yl]-3-fluorophenol;

(4aR,6R,8aS)-8a-(2,4-difluorophenyl)-6-(fluoromethyl)-4,4-a,5,6,8,8a-hexahydropyrano[3,4-d][1,3]thiazin-2-amine;

[(4aR,6R,8aS)-2-amino-8a-(2,4-difluorophenyl)-4,4-a,5,6,8,8a-hexahydropyrano[3,4-d][1,3]thiazin-6-yl]methanol;

(4aR,8aS)-8a-(4-fluorophenyl)-4,4-a,5,6,8,8a-hexahydropyrano[3,4-d][1,3]thiazin-2-amine;

(4aR,8aS)-8a-(2,6-difluorophenyl)-4,4-a,5,6,8,8a-hexahydropyrano[3,4-d][1,3]thiazin-2-amine;

(4aR,8aS)-8a-(2-methoxyphenyl)-4,4-a,5,6,8,8a-hexahydropyrano[3,4-d][1,3]thiazin-2-amine;

(4aR,6R,8aS)-8a-(2-fluorophenyl)-6-(phenoxymethyl)-4,4-a,5,6,8,8a-hexahydropyrano[3,4-d][1,3]thiazin-2-amine;

(4aR,6R,8aS)-8a-(2-fluorophenyl)-6-[(pyridin-2-yloxy)methyl]-4,4-a,5,6,8,8a-hexahydropyrano[3,4-d][1,3]thiazin-2-amine;

(4aR,6R,8aS)-6-(ethoxymethyl)-8a-(2-fluorophenyl)-4,4-a,5,6,8,8a-hexahydropyrano[3,4-d][1,3]thiazin-2-amine;

[(4aR,6R,8aS)-2-amino-8a-(2-fluorophenyl)-4,4-a,5,6,8,8a-hexahydropyrano[3,4-d][1,3]thiazin-6-yl]methyl benzoate;

(4aR,6R,8aS)-6-(fluoromethyl)-8a-(2-fluorophenyl)-4,4-a,5,6,8,8a-hexahydropyrano[3,4-d][1,3]thiazin-2-amine;

(4aR,6R,8aS)-8a-(2-fluorophenyl)-6-[(propan-2-yloxy)methyl]-4,4-a,5,6,8,8a-hexahydropyrano[3,4-d][1,3]thiazin-2-amine; and (4aR,8aS)-8a-phenyl-4,4-a,5,6,8,8a-hexahydropyrano[3,4-d][1,3]thiazin-2-amine;

or a pharmaceutically acceptable salt or solvate thereof.

In another aspect, the invention is directed to pharmaceutical compositions of a compound of formula (I)

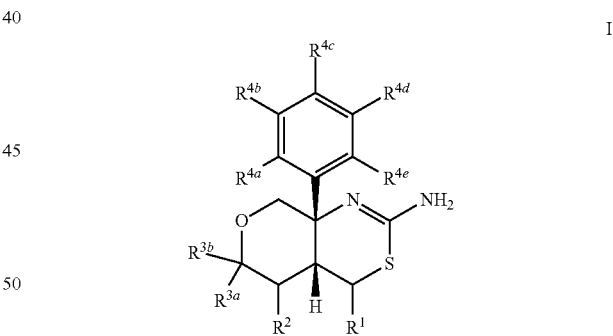

wherein $R^1$ and $R^2$ are independently halogen, hydrogen, $C_{1-6}$alkyl, $C_{2-6}$alkenyl or —$(C(R^{5a}R^{5b}))_m$—$(C_{3-6}$cycloalkyl); wherein said alkyl, alkenyl or cycloalkyl moieties may independently be optionally substituted with one to three $R^6$;

$R^{3a}$ is hydrogen, $C_{1-6}$alkyl, $C_{2-6}$alkenyl, —$(C(R^{5a}R^{5b}))_m$—$(C_{3-6}$cycloalkyl), —$(C(R^{5a}R^{5b}))_m$-(4- to 10-membered heterocycloalkyl), —$(C(R^{5a}R^{5b}))_m$—$(C_{6-10}$aryl), —$(C(R^{5a}R^{5b}))_m$-(5- to 10-membered heteroaryl), —$(C(R^{5a}R^{5b}))_m$—$OR^7$, —$C(O)N(R^8)_2$, —$(C(R^{5a}R^{5b}))_n$—$NHC(O)R^8$ or —$(C(R^{5a}R^{5b}))_n$—$N(R^8)_2$; wherein said alkyl, alkenyl, cycloalkyl or heterocycloalkyl moieties may independently be optionally substituted with one to three $R^{10}$; and wherein the aryl or heteroaryl moieties may independently be optionally substituted with one to five $R^{10}$;

$R^{3b}$ is hydrogen, $C_{1-3}$alkyl, $-(C(R^{5a}R^{5b}))_m-(C_{3-6}$cycloalkyl), $-(C(R^{5a}R^{5b}))_m$-(4- to 5-membered heterocycloalkyl) or $-(C(R^{5a}R^{5b}))_m-OR^7$; wherein said alkyl, cycloalkyl or heterocycloalkyl moieties may independently be optionally substituted with one to three $R^{10}$;

$R^{4a}$ is halogen, hydrogen, $C_{1-6}$alkyl, —CN or —OR$^9$; wherein said alkyl is optionally substituted by one to three fluoro;

$R^{4b}$ and $R^{4c}$ are independently halogen, hydrogen, $C_{1-6}$alkyl, —CN or —OR$^{12}$; wherein said alkyl is optionally substituted by one to three fluoro; or $R^{4b}$ and $R^{4c}$, together with the carbons to which they are bonded, form a 5- to 6-membered cycloalkyl or a 6-membered aryl, wherein said cycloalkyl or aryl is optionally substituted with one to three —CF$_3$, fluoro, $C_{1-6}$alkyl, —OC$_{1-6}$alkyl, —OH, —NH$_2$ or —NH—C$_{1-6}$alkyl;

$R^{4d}$ is halogen, hydrogen, $C_{1-6}$alkyl, —CN, —NO$_2$ or —OR$^{12}$; wherein said alkyl is optionally substituted by one to three fluoro; or $R^{4b}$ and $R^{4c}$, or $R^{4c}$ and $R^{4d}$, together with the carbons to which they are bonded, form a 5- to 6-membered cycloalkyl or a 6-membered aryl, wherein said cycloalkyl or aryl is optionally substituted with one to three —CF$_3$, fluoro, $C_{1-6}$alkyl, —OC$_{1-6}$alkyl, —OH, —NH$_2$ or —NH—C$_{1-6}$alkyl;

$R^{4e}$ is halogen, hydrogen, $C_{1-6}$alkyl, —CN or —OR$^9$; wherein said alkyl is optionally substituted by one to three fluoro;

$R^{5a}$ and $R^{4b}$ are independently fluoro, hydrogen or $C_{1-6}$alkyl;

$R^6$ is fluoro, —CN, $C_{1-6}$alkyl or —OR$^9$;

$R^7$ is independently hydrogen, $C_{1-6}$alkyl, $-(C(R^{5a}R^{5b}))_t$—($C_{3-6}$cycloalkyl), $-(C(R^{5a}R^{5b}))_t$-(4- to 10-membered heterocycloalkyl), $-(C(R^{5a}R^{5b}))_t$—($C_{6-10}$aryl), $-(C(R^{5a}R^{5b}))_t$-(5- to 10-membered heteroaryl) or —C(O)R$^{11}$; wherein said alkyl, cycloalkyl, heterocycloalkyl, aryl and heteroaryl are optionally substituted with one to three fluoro;

$R^8$ is independently hydrogen, $C_{1-6}$alkyl, $-(C(R^{5a}R^{5b}))_t$—($C_{3-6}$cycloalkyl), $-(C(R^{5a}R^{5b}))_t$-(4- to 10-membered heterocycloalkyl), $-(C(R^{5a}R^{5b}))_t$—($C_{6-10}$aryl) or $-(C(R^{5a}R^{5b}))_t$-(5- to 10-membered heteroaryl), wherein said alkyl, cycloalkyl, heterocycloalkyl, aryl and heteroaryl are optionally substituted with one to three fluoro;

$R^9$ is independently hydrogen, $C_{1-6}$alkyl or $C_{3-6}$alkenyl, optionally substituted with one to two fluoro;

$R^{10}$ is independently halogen, —OH, —CN, $C_{1-6}$alkyl, —OC$_{1-6}$alkyl; wherein said alkyl is optionally substituted with one to three fluoro;

$R^{11}$ is independently $C_{6-10}$aryl, $C_{1-6}$alkyl or —NR$^{13a}$R$^{13b}$;

$R^{12}$ is hydrogen or $C_{1-6}$alkyl optionally substituted with one to three fluoro;

$R^{13a}$ and $R^{13b}$ are each independently hydrogen, $C_{1-6}$alkyl, wherein said alkyl is optionally substituted with one to three fluoro; or $R^{13a}$ and $R^{13b}$ taken together with the nitrogen to which they are bonded form a 4- to 6-membered heterocycloalkyl ring, which may optionally include one oxygen to form a morpholine moiety;

m is 0, 1 or 2;

n is 1 or 2; and t is 0 or 1;

or a pharmaceutical salt or solvate thereof, and a pharmaceutically acceptable vehicle, diluents or carrier.

In a preferred aspect, the pharmaceutical composition contains the compound selected from:

rel-(4aR,8aS)-8a-(2-fluorophenyl)-4,4-a,5,6,8,8a-hexahydropyrano[3,4-d][1,3]thiazin-2-amine;

(4aR,6S,8aS)-8a-(2-fluorophenyl)-6-methyl-4,4-a,5,6,8,8a-hexahydropyrano[3,4-d][1,3]thiazin-2-amine;

(4aR,6R,8aS)-8a-(2-fluoro-5-nitrophenyl)-6-(methoxymethyl)-4,4-a,5,6,8,8a-hexahydropyrano[3,4-d][1,3]thiazin-2-amine;

(4aR,8aS)-8a-[2-(trifluoromethoxy)phenyl]-4,4-a,5,6,8,8a-hexahydropyrano[3,4-d][1,3]thiazin-2-amine;

(4aR,6S,8aS)-8a-(2-fluoro-5-nitrophenyl)-6-methyl-4,4-a,5,6,8,8a-hexahydropyrano[3,4-d][1,3]thiazin-2-amine;

(4aS,5S,8aS)-5-fluoro-8a-(2-fluorophenyl)-4,4-a,5,6,8,8a-hexahydropyrano[3,4-d][1,3]thiazin-2-amine;

(4aR,8aS)-8a-[5-nitro-2-(trifluoromethoxy)phenyl]-4,4-a,5,6,8,8a-hexahydropyrano[3,4-d][1,3]thiazin-2-amine;

(4aR,6R,8aS)-8a-(2-fluorophenyl)-6-(methoxymethyl)-4,4-a,5,6,8,8a-hexahydropyrano[3,4-d][1,3]thiazin-2-amine;

(4aR,8aS)-8a-(2-fluorophenyl)-5-methyl-4,4-a,5,6,8,8a-hexahydropyrano[3,4-d][1,3]thiazin-2-amine;

(4aR,6R,8aS)-6-[(benzyloxy)methyl]-8a-(2-fluorophenyl)-4,4-a,5,6,8,8a-hexahydropyrano[3,4-d][1,3]thiazin-2-amine;

(4aR,6R,8aS)-6-[(benzyloxy)methyl]-8a-(5-bromo-2-fluorophenyl)-4,4-a,5,6,8,8a-hexahydropyrano[3,4-d][1,3]thiazin-2-amine;

(4aS,5R,8aS)-8a-(2-fluorophenyl)-5-methoxy-4,4-a,5,6,8,8a-hexahydropyrano[3,4-d][1,3]thiazin-2-amine;

[(4aR,6R,8aS)-2-amino-8a-(2-fluorophenyl)-4,4-a,5,6,8,8a-hexahydropyrano[3,4-d][1,3]thiazin-6-yl]methanol;

(4R,4aR,8aS)-8a-(2-fluorophenyl)-4-methyl-4,4-a,5,6,8,8a-hexahydropyrano[3,4-d][1,3]thiazin-2-amine; and

[(4aR,6R,8aS)-2-amino-8a-(2-fluoro-5-nitrophenyl)-4,4-a,5,6,8,8a-hexahydropyrano[3,4-d][1,3]thiazin-6-yl]methanol;

or pharmaceutically acceptable salts or solvates thereof.

In another aspect any of the preceding compounds of formula I and their compositions are useful for inhibiting production of amyloid-β protein. In another embodiment, the compounds or compositions are useful for inhibiting beta-site amyloid-β precursor protein cleaving enzyme 1 (BACE). In a preferred embodiment, the compounds or compositions are useful for treating a neurodegenerative disease. In a preferred embodiment, the neurodegenerative disease is Alzheimer's Disease.

Accordingly, the invention is also directed to methods of treating a patient (preferably a human) for diseases in which the β-secretase enzyme is involved, such as Alzheimer's Disease, by administering a therapeutically effective amount of a thioamidine compound of any of the embodiments of formula I and I-a through 1-e, or a pharmaceutically acceptable salt thereof, and a pharmaceutically acceptable carrier.

The invention is also directed to methods of inhibiting BACE1 enzyme activity, by administering a therapeutically effective amount of a thioamidine compound of any of the embodiments of formula I and I-a through 1-e or a pharmaceutically acceptable salt thereof, and a pharmaceutically acceptable carrier, to a mammal or a patient in need thereof. In another embodiment, the invention is directed to methods of inhibiting BACE2 enzyme activity, by administering a therapeutically effective amount of a thioamidine compound of any of the embodiments of formula I and I-a through 1-e, or a pharmaceutically acceptable salt thereof, and a pharmaceutically acceptable carrier, to a mammal or a patient in need thereof.

The invention is also directed to methods for treating conditions or diseases of the central nervous system and neurological disorders in which the β-secretase enzyme is involved (such as migraine; epilepsy; Alzheimer's disease; Parkinson's disease; brain injury; stroke; cerebrovascular diseases (including cerebral arteriosclerosis, cerebral amyloid angiopathy, hereditary cerebral hemorrhage, and brain hypoxia-ischemia); cognitive disorders (including amnesia, senile dementia, HIV-associated dementia, Alzheimer's disease, Huntington's disease, Lewy body dementia, vascular dementia, drug-related dementia, tardive dyskinesia, myoclonus, dystonia, delirium, Pick's disease, Creutzfeldt-Jacob disease, HIV disease, Gilles de la Tourette's syndrome, epilepsy, muscular spasms and disorders associated with muscular spasticity or weakness including tremors, and mild cognitive impairment); mental deficiency (including spasticity, Down syndrome and fragile X syndrome); sleep disorders (including hypersomnia, circadian rhythm sleep disorder, insomnia, parasomnia, and sleep deprivation) and psychiatric disorders such as anxiety (including acute stress disorder, generalized anxiety disorder, social anxiety disorder, panic disorder, post-traumatic stress disorder, agoraphobia, and obsessive-compulsive disorder); factitious disorder (including acute hallucinatory mania); impulse control disorders (including compulsive gambling and intermittent explosive disorder); mood disorders (including bipolar I disorder, bipolar II disorder, mania, mixed affective state, major depression, chronic depression, seasonal depression, psychotic depression, seasonal depression, premenstrual syndrome (PMS) premenstrual dysphoric disorder (PDD), and postpartum depression); psychomotor disorder; psychotic disorders (including schizophrenia, schizoaffective disorder, schizophreniform, and delusional disorder); drug dependence (including narcotic dependence, alcoholism, amphetamine dependence, cocaine addiction, nicotine dependence, and drug withdrawal syndrome); eating disorders (including anorexia, bulimia, binge eating disorder, hyperphagia, obesity, compulsive eating disorders and pagophagia); sexual dysfunction disorders; urinary incontinence; neuronal damage disorders (including ocular damage, retinopathy or macular degeneration of the eye, tinnitus, hearing impairment and loss, and brain edema) and pediatric psychiatric disorders (including attention deficit disorder, attention deficit/hyperactive disorder, conduct disorder, and autism) in a mammal, preferably a human, comprising administering to said mammal a therapeutically effective amount of a compound of formula I and the compound of formula I-a through 1-e or pharmaceutically acceptable salt thereof. The compounds of formula I and the compound of formula I-a through 1-e may also be useful for improving memory (both short-term and long-term) and learning ability.

The text revision of the fourth edition of the Diagnostic and Statistical Manual of Mental Disorders (DSM-IV-TR) (2000, American Psychiatric Association, Washington D.C.) provides a diagnostic tool for identifying many of the disorders described herein. The skilled artisan will recognize that there are alternative nomenclatures, nosologies, and classification systems for disorders described herein, including those as described in the DMS-IV-TR, and that terminology and classification systems evolve with medical scientific progress.

Preferred methods are for treating a neurological disorder (such as migraine; epilepsy; Alzheimer's Disease; Parkinson's disease; Niemann-Pick type C; brain injury; stroke; cerebrovascular disease; cognitive disorder; sleep disorder) or a psychiatric disorder (such as anxiety; factitious disorder; impulse control disorder; mood disorder; psychomotor disorder; psychotic disorder; drug dependence; eating disorder; and pediatric psychiatric disorder) in a mammal, preferably a human, comprising administering to said mammal a therapeutically effective amount of a compound of Formula I and I-a through 1-e or pharmaceutically acceptable salt thereof.

Also provided herein are compositions comprising a pharmaceutically effective amount of one or more of the compounds described herein and a pharmaceutically acceptable vehicle, carrier or excipient.

The present invention is also directed to the use of a combination of a BACE inhibitor compound as provided in the compound formula I, and I-a through 1-e and one or more additional pharmaceutically active agent(s).

All patents, patent applications and references referred to herein are hereby incorporated by reference in their entirety.

Other features and advantages of this invention will be apparent from this specification and the appendent claims which describe the invention.

DEFINITIONS

The term "alkyl" refers to a linear or branched-chain saturated hydrocarbyl substituent (i.e., a substituent obtained from a hydrocarbon by removal of a hydrogen); in one embodiment from one to twelve carbon atoms; in another embodiment, from one to ten carbon atoms; in another embodiment, from one to six carbon atoms; and in another embodiment, from one to four carbon atoms. Examples of such substituents include methyl, ethyl, propyl (including n-propyl and isopropyl), butyl (including n-butyl, isobutyl, sec-butyl and tert-butyl), pentyl, isoamyl, hexyl and the like.

"Alkenyl" refers to an aliphatic hydrocarbon having at least one carbon-carbon double bond, including straight chain, branched chain or cyclic groups having at least one carbon-carbon double bond. Preferably, it is a medium-size alkenyl having 2 to 6 carbon atoms. For example, as used herein, the term "$C_{2-6}$alkenyl" means straight or branched chain unsaturated radicals of 2 to 6 carbon atoms, including, but not limited to ethenyl, 1-propenyl, 2-propenyl (allyl), isopropenyl, 2-methyl-1-propenyl, 1-butenyl, 2-butenyl, and the like; optionally substituted by 1 to 5 suitable substituents as defined above such as fluoro, chloro, trifluoromethyl, ($C_1$-$C_6$)alkoxy, ($C_6$-$C_{10}$)aryloxy, trifluoromethoxy, difluoromethoxy or ($C_1$-$C_6$)alkyl. When the compounds of the invention contain a $C_{2-6}$alkenyl group, the compound may exist as the pure E (entgegen) form, the pure Z (zusammen) form, or any mixture thereof.

"Alkylidene" refers to a divalent group formed from an alkane by removal of two hydrogen atoms from the same carbon atom, the free valencies of which are part of a double bond.

"Alkynyl" refers to an aliphatic hydrocarbon having at least one carbon-carbon triple bond, including straight chain, branched chain or cyclic groups having at least one carbon-carbon triple bond. Preferably, it is a lower alkynyl having 2 to 6 carbon atoms. For example, as used herein, the term "$C_{2-6}$alkynyl" is used herein to mean a straight or branched hydrocarbon chain alkynyl radical as defined above having 2 to 6 carbon atoms and one triple bond.

The term "aryl" refers to an aromatic substituent containing one ring or two or three fused rings. The aryl substituent may have six to eighteen carbon atoms. As an example, the aryl substituent may have six to fourteen carbon atoms. The term "aryl" may refer to substituents such as phenyl, naphthyl and anthracenyl. The term "aryl" also includes substituents such as phenyl, naphthyl and anthracenyl that are fused to a $C_4$-$C_{10}$ carbocyclic ring, such as a $C_5$ or a $C_6$ carbocyclic ring, or to a 4- to 10-membered heterocyclic ring, wherein a group having such a fused aryl group as a substituent is bound to an aromatic carbon of the aryl group. When such a fused aryl group is substituted with one more substituents, the one or more substituents, unless otherwise specified, are each bound to an aromatic carbon of the fused aryl group. The fused $C_4$-$C_{10}$ carbocyclic or 4- to 10-membered heterocyclic ring may be optionally substituted with halogen, $C_1$-$C_6$ alkyl, $C_3$-$C_{10}$ cycloalkyl, or =O. Examples of aryl groups include phenyl, naphthalenyl, tetrahydronaphthalenyl, indenyl, isoindenyl, indanyl, anthracenyl, phenanthrenyl, benzonaphthenyl, and fluorenyl.

The term "cycloalkyl" refers to a carbocyclic substituent obtained by removing a hydrogen from a saturated carbocyclic molecule and having three to fourteen carbon atoms. In one embodiment, a cycloalkyl substituent has three to ten carbon atoms. Examples of cycloalkyl include cyclopropyl, cyclobutyl, cyclopentyl and cyclohexyl.

The term "cycloalkyl" also includes substituents that are fused to a $C_6$-$C_{10}$ aromatic ring or to a 5- to 10-membered heteroaromatic ring, wherein a group having such a fused cycloalkyl group as a substituent is bound to a carbon atom of the cycloalkyl group. When such a fused cycloalkyl group is substituted with one or more substituents, the one or more substituents, unless otherwise specified, are each bound to a carbon atom of the cycloalkyl group. The fused $C_6$-$C_{10}$ aromatic ring or 5- to 10-membered heteroaromatic ring may be optionally substituted with halogen, $C_1$-$C_6$ alkyl, $C_3$-$C_{10}$ cycloalkyl, or =O.

The term "cycloalkyl" includes mono-, bi- and tricyclic saturated carbocycles, as well as bridged and fused ring carbocycles, as well as spiro-fused ring systems. Examples of fused ring systems include bicyclodecanyl and decalinyl.

In some instances, the number of carbon atoms in a hydrocarbyl substituent (i.e., alkyl, alkenyl, cycloalkyl, cycloalkenyl, aryl, etc.) is indicated by the prefix "$C_x$-$C_y$-" or "$C_{x\text{-}y}$", wherein x is the minimum and y is the maximum number of carbon atoms in the substituent. Thus, for example, "$C_1$-$C_6$-alkyl" or "$C_{1\text{-}6}$alkyl" refers to an alkyl substituent containing from 1 to 6 carbon atoms. Illustrating further, $C_3$-$C_6$-cycloalkyl refers to saturated cycloalkyl containing from 3 to 6 carbon ring atoms.

In some instances, the number of atoms in a cyclic substituent containing one or more heteroatoms (i.e., heteroaryl or heterocycloalkyl) is indicated by the prefix "x- to y-membered", wherein x is the minimum and y is the maximum number of atoms forming the cyclic moiety of the substituent. Thus, for example, "5- to 8-membered heterocycloalkyl" refers to a heterocycloalkyl containing from 5 to 8 atoms, including one or more heteroatoms, in the cyclic moiety of the heterocycloalkyl.

The term "hydrogen" refers to hydrogen substituent, and may be depicted as —H.

The term "hydroxy" or "hydroxyl" refers to —OH. When used in combination with another term(s), the prefix "hydroxy" indicates that the substituent to which the prefix is attached is substituted with one or more hydroxy substituents. Compounds bearing a carbon to which one or more hydroxy substituents include, for example, alcohols, enols and phenol.

The term "hydroxyalkyl" refers to an alkyl that is substituted with at least one hydroxy substituent. Examples of hydroxyalkyl include hydroxymethyl, hydroxyethyl, hydroxypropyl and hydroxybutyl.

The term "halo" or "halogen" refers to fluorine (which may be depicted as —F), chlorine (which may be depicted as —Cl), bromine (which may be depicted as —Br), or iodine (which may be depicted as —I).

The term "heterocycloalkyl" refers to a substituent obtained by removing a hydrogen from a saturated or partially saturated ring structure containing a total of 3 to 14 ring atoms, wherein at least one of the ring atoms is a heteroatom (i.e., oxygen, nitrogen, or sulfur), with the remaining ring atoms being independently selected from the group consisting of carbon, oxygen, nitrogen, and sulfur. A heterocycloalkyl alternatively may comprise 2 or 3 rings fused together, wherein at least one such ring contains a heteroatom as a ring atom (i.e., nitrogen, oxygen, or sulfur). In a group that has a heterocycloalkyl substituent, the ring atom of the heterocycloalkyl substituent that is bound to the group may be the at least one heteroatom, or it may be a ring carbon atom, where the ring carbon atom may be in the same ring as the at least one heteroatom or where the ring carbon atom may be in a different ring from the at least one heteroatom. Similarly, if the heterocycloalkyl substituent is in turn substituted with a group or substituent, the group or substituent may be bound to the at least one heteroatom, or it may be bound to a ring carbon atom, where the ring carbon atom may be in the same ring as the at least one heteroatom or where the ring carbon atom may be in a different ring from the at least one heteroatom.

The term "heterocycloalkyl" also includes substituents that are fused to a $C_6$-$C_{10}$ aromatic ring or to a 5- to 10-membered heteroaromatic ring, wherein a group having such a fused heterocycloalkyl group as a substituent is bound to a heteroatom of the heterocycloalkyl group or to a carbon atom of the heterocycloalkyl group. When such a fused heterocycloalkyl group is substituted with one more substituents, the one or more substituents, unless otherwise specified, are each bound to a heteroatom of the heterocycloalkyl group or to a carbon atom of the heterocycloalkyl group. The fused $C_6$-$C_{10}$ aromatic ring or 5- to 10-membered heteroaromatic ring may be optionally substituted with halogen, $C_1$-$C_6$ alkyl, $C_3$-$C_{10}$ cycloalkyl, $C_1$-$C_6$ alkoxy, or =O.

The term "heteroaryl" refers to an aromatic ring structure containing from 5 to 14 ring atoms in which at least one of the ring atoms is a heteroatom (i.e., oxygen, nitrogen, or sulfur), with the remaining ring atoms being independently selected from the group consisting of carbon, oxygen, nitrogen, and sulfur. A heteroaryl may be a single ring or 2 or 3 fused rings. Examples of heteroaryl substituents include 6-membered ring substituents such as pyridyl, pyrazyl, pyrimidinyl, and pyridazinyl; 5-membered ring substituents such as triazolyl, imidazolyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, isobenzothiofuranyl, benzisoxazolyl, benzoxazolyl, purinyl, and anthranilyl; and 6/6-membered fused rings such as quinolinyl, isoquinolinyl, cinnolinyl, quinazolinyl, and 1,4-benzoxazinyl. In a group that has a heteroaryl substituent, the ring atom of the heteroaryl substituent that is bound to the group may be the at least one heteroatom, or it may be a ring carbon atom, where the ring carbon atom may be in the same ring as the at least one heteroatom or where the ring carbon atom may be in a different ring from the at least one heteroatom. Similarly, if the heteroaryl substituent is in turn substituted with a group or substituent, the group or substituent may be bound to the at least one heteroatom, or it may be bound to a ring carbon atom, where the ring carbon atom may be in the same ring as the at least one heteroatom or where the ring carbon atom may be in a different ring from the at least one heteroatom. The term "heteroaryl" also includes pyridyl N-oxides and groups containing a pyridine N-oxide ring.

Examples of single-ring heteroaryls and heterocycloalkyls include furanyl, dihydrofuranyl, tetrahydrofuranyl, thiophenyl, dihydrothiophenyl, tetrahydrothiophenyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiaoxadiazolyl, oxathiazolyl, oxadiazolyl (including oxadiazolyl, 1,2,4-oxadiazolyl, 1,2,5-oxadiazolyl, or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl (including 1,2-pyranyl or 1,4-pyranyl), dihydropyranyl, pyridinyl, piperidinyl, diazinyl (including pyridazinyl, pyrimidinyl, piperazinyl, triazinyl (including s-triazinyl, as-triazinyl and v-triazinyl), oxazinyl (including 1,2,3-oxazinyl, 1,3,2-oxazinyl, 1,3,6-oxazinyl, 1,2,6-oxazinyl, or 1,4-oxazinyl), isoxazinyl (including o-isoxazinyl or p-isoxazinyl), oxazolidinyl, isoxazolidinyl, oxathiazinyl (including 1,2,5-oxathiazinyl or 1,2,6-oxathiazinyl), oxadiazinyl (including 1,4,2-oxadiazinyl or 1,3,5,2-oxadiazinyl), morpholinyl, azepinyl, oxepinyl, thiepinyl, and diazepinyl.

Examples of 2-fused-ring heteroaryls include, indolizinyl, pyridinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl, indolyl, isoindolyl, indoleninyl, isoindazolyl, benzazinyl, phthalazinyl, quinoxalinyl, quinazolinyl, benzodiazinyl, benzopyranyl, benzothiopyranyl, benzoxazolyl, indoxazinyl, anthranilyl, benzodioxolyl, benzodioxanyl, benzoxadiazolyl, benzofuranyl, isobenzofuranyl, benzothienyl, isobenzothienyl, benzothiazolyl, benzothiadiazolyl, benzimidazolyl, benzotriazolyl, benzoxazinyl, benzisoxazinyl, and tetrahydroisoquinolinyl.

Examples of 3-fused-ring heteroaryls or heterocycloalkyls include 5,6-dihydro-4H-imidazo[4,5,1-ij]quinolinyl, 4,5-dihydroimidazo[4,5,1-hi]indolyl, 4,5,6,7-tetrahydroimidazo[4,5,1-jk][1]benzazepinyl, and dibenzofuranyl.

Other examples of fused-ring heteroaryls include benzo-fused heteroaryls such as indolyl, isoindolyl, indoleninyl, isoindazolyl, benzazinyl (including quinolinyl or isoquinolinyl), phthalazinyl, quinoxalinyl, quinazolinyl, benzodiazinyl (including cinnolinyl or quinazolinyl).

The term "heteroaryl" also includes substituents that are fused to a $C_4$-$C_{10}$ carbocyclic ring, such as a $C_5$ or a $C_6$ carbocyclic ring, or to a 4- to 10-membered heterocyclic ring, wherein a group having such a fused heteroaryl group as a substituent is bound to an aromatic carbon of the heteroaryl group or to a heteroatom of the heteroaryl group. When such a fused heteroaryl group is substituted with one more substituents, the one or more substituents, unless otherwise specified, are each bound to an aromatic carbon of the heteroaryl group or to a heteroatom of the heteroaryl group. The fused $C_4$-$C_{10}$ carbocyclic or 4- to 10-membered heterocyclic ring may be optionally substituted with halogen, $C_1$-$C_6$ alkyl, $C_3$-$C_{10}$ cycloalkyl, or =O.

Additional examples of heteroaryls and heterocycloalkyls include: 3-1H-benzimidazol-2-one, (1-substituted)-2-oxo-benzimidazol-3-yl, 2-tetrahydrofuranyl, 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzo[1,3]dioxine, benzo[1,4]dioxine, benzopyrrolidinyl, benzopiperidinyl, benzoxolanyl, benzothiolanyl, 4,5,6,7-tetrahydropyrazol[1,5-a]pyridine, benzothianyl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, quinolizinyl, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-2-yl (C-attached).

If substituents are described as being "independently selected" from a group, each instance of a substituent is selected independent of the other. Each substituent therefore may be identical to or different from the other substituent(s).

As used herein the term "formula I", and the compound of formula I, I-a through 1-e may be hereinafter referred to as a "compound(s) of the invention." Such terms are also defined to include all forms of the compound of formula I, the compound of formula I-a through I-e including hydrates, solvates, isomers, crystalline and non-crystalline forms, isomorphs, polymorphs, and metabolites thereof. For example, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist as clathrates or other complexes. Included within the scope of the invention are complexes such as clathrates, drug-host inclusion complexes wherein, in contrast to the aforementioned solvates, the drug and host are present in stoichiometric or non-stoichiometric amounts. Also included are complexes of the compounds of the invention containing two or more organic and/or inorganic components which may be in stoichiometric or non-stoichiometric amounts. The resulting complexes may be ionized, partially ionized, or non-ionized. For a review of such complexes, see J. Pharm. Sci., 64 (8), 1269-1288 by Haleblian (August 1975).

The compounds of the invention have asymmetric carbon atoms. The carbon-carbon bonds of the compounds of the invention may be depicted herein using a solid line (-), a solid wedge (━━) or a dotted wedge (⋯⋯). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of Formula I may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula I can exist as enantiomers and diastereomers or as racemates and mixtures thereof. The use of a solid line to depict bonds to one or more asymmetric carbon atoms in a compound of Formula I and the use of a solid or dotted wedge to depict bonds to other asymmetric carbon atoms in the same compound is meant to indicate that a mixture of diastereomers is present.

Stereoisomers of Formula I include cis and trans isomers, optical isomers such as R and S enantiomers, diastereomers, geometric isomers, rotational isomers, conformational isomers, and tautomers of the compounds of the invention, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The present invention comprises the tautomeric forms of compounds of the invention Where structural isomers are interconvertible via a low energy barrier, tautomeric isomerism ('tautomerism') can occur. This can take the form of proton tautomerism in compounds of the invention containing, for example, an imino, keto, or oxime group, or so-called valence tautomerism in compounds which contain an aromatic moiety. It follows that a single compound may exhibit more than one type of isomerism. The various ratios of the tautomers in solid and liquid form is dependent on the various substituents on the molecule as well as the particular crystallization technique used to isolate a compound.

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of formula I with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts." Salts encompassed within the term "pharmaceutically acceptable salts" refer to non-toxic salts of the compounds of this invention which are generally prepared by reacting the free base with a suitable organic or inorganic acid.

Suitable pharmaceutically acceptable acid addition salts of the compounds of the present invention when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include, for example, aliphatic, cycloaliphatic, aromatic, araliphatic, heterocyclic, carboxylic, and sulfonic classes of organic acids.

Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include alkali metal salts, i.e., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (i.e., dimethyl, diethyl, dibuytl, and diamyl sulfates), long chain halides (e.g., decyl, lauryl, myristyl, and stearyl chlorides, bromides, and iodides), arylalkyl halides (e.g., benzyl and phenethyl bromides), and others.

In one embodiment, hemisalts of acids and bases may also be formed, for example, hemisulfate and hemicalcium salts.

Also within the scope of the present invention are so-called "prodrugs" of the compound of the invention. Thus, certain derivatives of the compound of the invention which may have little or no pharmacological activity themselves can, when administered into or onto the body, be converted into the compound of the invention having the desired activity, for example, by hydrolytic cleavage. Such derivatives are referred to as "prodrugs." Further information on the use of prodrugs may be found in "Pro-drugs as Novel Delivery Systems, Vol. 14, ACS Symposium Series (T. Higuchi and W. Stella) and "Bioreversible Carriers in Drug Design," Pergamon Press, 1987 (ed. E. B. Roche, American Pharmaceutical Association). Prodrugs in accordance with the invention can, for example, be produced by replacing appropriate functionalities present in the compounds of any of formula I with certain moieties known to those skilled in the art as "pro-moieties" as described, for example, in "Design of Prodrugs" by H Bundgaard (Elsevier, 1985).

The present invention also includes isotopically labeled compounds, which are identical to those recited in formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, sulfur, fluorine and chlorine, such as $^{2}H$, $^{3}H$, $^{13}C$, $^{11}C$, $^{14}C$, $^{15}N$, $^{18}O$, $^{17}O$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of formula I of this invention and prodrugs thereof can generally be prepared by carrying out the procedures disclosed in the Schemes and/or in the Examples and Preparations below, by substituting a readily available isotopically labeled reagent for a non-isotopically labeled reagent.

DETAILED DESCRIPTION OF THE INVENTION

Typically, a compound of the invention is administered in an amount effective to treat a condition as described herein. The compounds of the invention are administered by any suitable route in the form of a pharmaceutical composition adapted to such a route, and in a dose effective for the treatment intended. Therapeutically effective doses of the compounds required to treat the progress of the medical condition are readily ascertained by one of ordinary skill in the art using preclinical and clinical approaches familiar to the medicinal arts.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

The compounds of the invention may be administered orally. Oral administration may involve swallowing, so that the compound enters the gastrointestinal tract, or buccal or sublingual administration may be employed, by which the compound enters the blood stream directly from the mouth.

In another embodiment, the compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing from about 0.01 mg to about 500 mg of the active ingredient, or in another embodiment, from about 1 mg to about 100 mg of active ingredient. Intravenously, doses may range from about 0.1 to about 10 mg/kg/minute during a constant rate infusion.

Suitable subjects according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises the use of one or more compounds of the invention for the preparation of a medicament for the treatment of the conditions recited herein.

For the treatment of the conditions referred to above, the compound of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of formula I are ordinarily combined with one or more adjuvants. Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneal injections, intramuscular injections, intrasternal injections, and infusion. Injectable preparations (e.g., sterile injectable aqueous or oleaginous suspensions) may be formulated according to the known art using suitable dispersing, wetting agents, and/or suspending agents.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J. Pharm. Sci., 88 (10), 955-958, by Finnin and Morgan (October 1999).

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (e.g., absorbable gel sponges, collagen) and non-biodegradable (e.g., silicone) implants, wafers, lenses and particulate or vesicular systems, such as niosomes or liposomes. A polymer such as cross-linked polyacrylic acid, polyvinyl alcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3, 3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients ($3^{rd}$ Ed.), American Pharmaceutical Association, Washington, 1999.

The compounds of the present invention can be used, alone or in combination with other therapeutic agents, in the treatment of various conditions or disease states. The compound(s) of the present invention and other therapeutic agent(s) may be may be administered simultaneously (either in the same dosage form or in separate dosage forms) or sequentially.

Two or more compounds may be administered simultaneously, concurrently or sequentially. Additionally, simultaneous administration may be carried out by mixing the compounds prior to administration or by administering the compounds at the same point in time but at different anatomic sites or using different routes of administration.

The phrases "concurrent administration," "co-administration," "simultaneous administration," and "administered simultaneously" mean that the compounds are administered in combination.

The present invention includes the use of a combination of a BACE inhibitor compound as provided in formula I and the compound of formula I-a through 1-e and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of formula I or a pharmaceutically acceptable salt of the compound; (b) a second pharmaceutically active agent; and (c) a pharmaceutically acceptable carrier, vehicle or diluent.

Various pharmaceutically active agents may be selected for use in conjunction with the compounds of Formula I and the compound of formula I-a through 1-e, depending on the disease, disorder, or condition to be treated. Pharmaceutically active agents that may be used in combination with the compositions of the present invention include, without limitation:

(i) acetylcholinesterase inhibitors, such as donepezil hydrochloride (ARICEPT®, MEMAC), physostigmine salicylate (ANTILIRIUM®), physostigmine sulfate (ESERINE), metrifonate, neostigmine, ganstigmine, pyridostigmine (MESTINON), ambenonium (MYTELASE®), demecarium, DEBIO® (also known as ZT-1; DEBIOPHARM®), rivastigmine (EXELON®), ladostigil, NP-0361, galantamine hydrobromide (RAZADYNE®, REMINYL®, NIVALIN®), tacrine (COGNEX®), tolserine, velnacrine maleate, memoquin, huperzine A (HUP-A; Neuro-Hitech), phenserine, edrophonium (ENLON®, TENSILON®), and INM-176;

(ii) amyloid-β (or fragments thereof), such as Aβ$_{1-15}$ conjugated to pan HLA DR-binding epitope (PADRE®), ACC-001 (Elan/Wyeth), ACI-01, ACI-24, AN-1792, Affitope AD-01, CAD106, and V-950;

(iii) antibodies to amyloid-β (or fragments thereof), such as ponezumab, solanezumab, bapineuzumab (also known as AAB-001), AAB-002 (Wyeth/Elan), ACI-01-Ab7, BAN-2401, intravenous Ig (GAMMAGARD®), LY2062430 (humanized m266; Lilly), R1450 (Roche), ACU-5A5, huC091, and those disclosed in International Patent Publication Nos WO04/032868, WO05/025616, WO06/036291, WO06/069081, WO06/118959, in US Patent Publication Nos US2003/0073655, US2004/0192898, US2005/0048049, US2005/0019328, in European Patent Publication Nos EP0994728 and 1257584, and in U.S. Pat. No. 5,750,349;

(iv) amyloid-lowering or -inhibiting agents (including those that reduce amyloid production, accumulation and fibrillization) such as dimebon, davunetide, eprodisate, leuprolide, SK-PC-B70M, celecoxib, lovastatin, anapsos, oxiracetam, pramiracetam, varenicline, nicergoline, colostrinin, bisnorcymserine (also known as BNC), NIC5-15 (Humanetics), E-2012 (Eisai), pioglitazone, clioquinol (also known as PBT1), PBT2 (Prana Biotechnology), flurbiprofen (ANSAID®, FROBEN®) and its R-enantiomer tarenflurbil (FLURIZAN®), nitroflurbiprofen, fenoprofen (FENOPRON, NALFON®), ibuprofen (ADVIL®, MOTRIN®, NUROFEN®), ibuprofen lysinate, meclofenamic acid, meclofenamate sodium (MECLOMEN®), indomethacin (INDOCIN®), diclofenac sodium (VOLTAREN®), diclofenac potassium, sulindac (CLINORIL®), sulindac sulfide, diflunisal (DOLOBID®), naproxen (NAPROSYN®), naproxen sodium (ANAPROX®, ALEVE®), ARC031 (Archer Pharmaceuticals), CAD-106 (Cytos), LY450139 (Lilly), insulin-degrading enzyme (also known as insulysin), the gingko biloba extract EGb-761 (ROKAN®, TEBONIN®), tramiprosate (CEREBRIL®, ALZHEMED®), eprodisate (FIBRILLEX®, KIACTA®), compound W (3,5-bis(4-nitrophenoxy)benzoic acid), NGX-96992, neprilysin (also known as neutral endopeptidase (NEP)), scyllo-inositol (also known as scyllitol), atorvastatin (LIPITOR®), simvastatin (ZOCOR®), KLVFF-(EEX)3, SKF-74652, ibutamoren mesylate, BACE inhibitors such as ASP-1702, SCH-745966, JNJ-715754, AMG-0683, AZ-12304146, BMS-782450, GSK-188909, NB-533, E2609 and TTP-854; Gamma Secretase Modulators such as ELND-007; and RAGE (receptor for advanced glycation end-products) inhibitors, such as TTP488 (Transtech) and TTP4000 (Transtech), and those disclosed in U.S. Pat. No. 7,285,293, including PTI-777;

(v) alpha-adrenergic receptor agonists, such as guanfacine (INTUNIV, TENEX), clonidine (CATAPRES), metaraminol (ARAMINE), methyldopa (ALDOMET, DOPAMET, NOVOMEDOPA), tizanidine (ZANAFLEX), phenylephrine (also known as neosynephrine), methoxamine, cirazoline, guanfacine (INTUNIV), lofexidine, xylazine, modafinil (PROVIGIL), adrafinil, and armodafinil (NUVIGIL);

(vi) beta-adrenergic receptor blocking agents (beta blockers), such as carteolol, esmolol (BREVIBLOC), labetalol (NORMODYNE, TRANDATE), oxprenolol (LARACOR, TRASACOR), pindolol (VISKEN), propanolol (INDERAL), sotalol (BETAPACE, SOTALEX, SOTACOR), timolol (BLOCADREN, TIMOPTIC), acebutolol (SECTRAL, PRENT), nadolol (CORGARD), metoprolol tartrate (LOPRESSOR), metoprolol succinate (TOPROL-XL), atenolol (TENORMIN), butoxamine, and SR 59230A (Sanofi);

(vii) anticholinergics, such as amitriptyline (ELAVIL, ENDEP), butriptyline, benztropine mesylate (COGENTIN), trihexyphenidyl (ARTANE), diphenhydramine (BENADRYL), orphenadrine (NORFLEX), hyoscyamine, atropine (ATROPEN), scopolamine (TRANSDERM-SCOP), scopolamine methylbromide (PARMINE), dicycloverine (BENTYL, BYCLOMINE, DIBENT, DILOMINE), tolterodine (DETROL), oxybutynin (DITROPAN, LYRINEL XL, OXYTROL), penthienate bromide, propantheline (PRO-BANTHINE), cyclizine, imipramine hydrochloride (TOFRANIL), imipramine maleate (SURMONTIL), lofepramine, desipramine (NORPRAMIN), doxepin (SINEQUAN, ZONALON), trimipramine (SURMONTIL), and glycopyrrolate (ROBINUL);

(viii) anticonvulsants, such as carbamazepine (TEGRETOL, CARBATROL), oxcarbazepine (TRILEPTAL), phenyloin sodium (PHENYTEK), fosphenyloin (CEREBYX, PRODILANTIN), divalproex sodium (DEPAKOTE), gabapentin (NEURONTIN), pregabalin (LYRICA), topirimate (TOPAMAX), valproic acid (DEPAKENE), valproate sodium (DEPACON), 1-benzyl-5-bromouracil, progabide, beclamide, zonisamide (TRERIEF, EXCEGRAN), CP-465022, retigabine, talampanel, and primidone (MYSOLINE);

(ix) antipsychotics, such as lurasidone (LATUDA, also known as SM-13496; Dainippon Sumitomo), aripiprazole (ABILIFY), chlorpromazine (THORAZINE), haloperidol (HALDOL), iloperidone (FANAPTA), flupentixol decanoate (DEPIXOL, FLUANXOL), reserpine (SERPLAN), pimozide (ORAP), fluphenazine decanoate, fluphenazine hydrochloride, prochlorperazine (COMPRO), asenapine (SAPHRIS), loxapine (LOXITANE), molindone (MOBAN), perphenazine, thioridazine, thiothixine, trifluoperazine (STELAZINE), ramelteon, clozapine (CLOZARIL), norclozapine (ACP-104), risperidone (RISPERDAL), paliperidone (INVEGA), melperone, olanzapine (ZYPREXA), quetiapine (SEROQUEL), talnetant, amisulpride, ziprasidone (GEODON), blonanserin (LONASEN), and ACP-103 (Acadia Pharmaceuticals);

(x) calcium channel blockers such as lomerizine, ziconotide, nilvadipine (ESCOR, NIVADIL), diperdipine, amlodipine (NORVASC, ISTIN, AMLODIN), felodipine (PLENDIL), nicardipine (CARDENE), nifedipine (ADALAT, PROCARDIA), MEM 1003 and its parent compound nimodipine (NIMOTOP), nisoldipine (SULAR), nitrendipine, lacidipine (LACIPIL, MOTENS), lercanidipine (ZANIDIP), lifarizine, diltiazem (CARDIZEM), verapamil (CALAN, VERELAN), AR-R 18565 (AstraZeneca), and enecadin;

(xi) catechol O-methyltransferase (COMT) inhibitors, such as nitecapone, tolcapone (TASMAR), entacapone (COMTAN), and tropolone;

(xii) central nervous system stimulants, such as atomoxetine, reboxetine, yohimbine, caffeine, phenmetrazine, phendimetrazine, pemoline, fencamfamine (GLUCOENERGAN, REACTIVAN), fenethylline (CAPTAGON), pipradol (MERETRAN), deanol (also known as dimethylaminoethanol), methylphenidate (DAYTRANA), methylphenidate hydrochloride (RITALIN), dexmethylphenidate (FOCALIN), amphetamine (alone or in combination with other CNS stimulants, e.g., ADDERALL (amphetamine aspartate, amphetamine sulfate, dextroamphetamine saccharate, and dextroamphetamine sulfate)), dextroamphetamine sulfate (DEXEDRINE, DEXTROSTAT), methamphetamine (DESOXYN), lisdexamfetamine (VYVANSE), and benzphetamine (DIDREX);

(xiii) corticosteroids, such as prednisone (STERAPRED, DELTASONE), prednisolone (PRELONE), prednisolone acetate (OMNIPRED, PRED MILD, PRED FORTE), prednisolone sodium phosphate (ORAPRED ODT), methylprednisolone (MEDROL); methylprednisolone acetate (DEPO-MEDROL), and methylprednisolone sodium succinate (A-METHAPRED, SOLU-MEDROL);

(xiv) dopamine receptor agonists, such as apomorphine (APOKYN), bromocriptine (PARLODEL), cabergoline (DOSTINEX), dihydrexidine, dihydroergocryptine, fenoldopam (CORLOPAM), lisuride (DOPERGIN), terguride spergolide (PERMAX), piribedil (TRIVASTAL, TRASTAL), pramipexole (MIRAPEX), quinpirole, ropinirole (REQUIP), rotigotine (NEUPRO), SKF-82958 (GlaxoSmithKline), cariprazine, pardoprunox and sarizotan;

(xv) dopamine receptor antagonists, such as chlorpromazine, fluphenazine, haloperidol, loxapine, risperidone, thioridazine, thiothixene, trifluoperazine, tetrabenazine (NITOMAN, XENAZINE),7-hydroxyamoxapine, droperidol (INAPSINE, DRIDOL, DROPLETAN), domperidone (MOTILIUM), L-741742, L-745870, raclopride, SB-277011A, SCH-23390, ecopipam, SKF-83566, and metoclopramide (REGLAN);

(xvi) dopamine reuptake inhibitors such as bupropion, safinamide, nomifensine maleate (MERITAL), vanoxerine (also known as GBR-12909) and its decanoate ester DBL-583, and amineptine;

(xvii) gamma-aminobutyric acid (GABA) receptor agonists, such as baclofen (LIORESAL, KEMSTRO), siclofen, pentobarbital (NEMBUTAL), progabide (GABRENE), and clomethiazole;

(xviii) histamine 3 (H3) antagonists such as ciproxifan, tiprolisant, S-38093, irdabisant, pitolisant, GSK-239512, GSK-207040, JNJ-5207852, JNJ-17216498, HPP-404, SAR-110894, trans-N-ethyl-3-fluoro-3-[3-fluoro-4-(pyrrolidin-1-ylmethyl)phenyl]cyclobutanecarboxamide (PF-3654746) and those disclosed in US Patent Publication Nos US2005-0043354, US2005-0267095, US2005-0256135, US2008-0096955, US2007-1079175, and US2008-0176925; International Patent Publication Nos WO2006/136924, WO2007/063385, WO2007/069053, WO2007/088450, WO2007/099423, WO2007/105053, WO2007/138431, and WO2007/088462; and U.S. Pat. No. 7,115,600);

(xix) immunomodulators such as glatiramer acetate (also known as copolymer-1; COPAXONE), MBP-8298 (synthetic myelin basic protein peptide), dimethyl fumarate, fingolimod (also known as FTY720), roquinimex (LINOMIDE), laquinimod (also known as ABR-215062 and SAIK-MS), ABT-874 (human anti-IL-12 antibody; Abbott), rituximab (RITUXAN), alemtuzumab (CAMPATH), daclizumab (ZENAPAX), and natalizumab (TYSABRI);

(xx) immunosuppressants such as methotrexate (TREXALL, RHEUMATREX), mitoxantrone (NOVANTRONE), mycophenolate mofetil (CELLCEPT), mycophenolate sodium (MYFORTIC), azathioprine (AZASAN, IMURAN), mercaptopurine (PURI-NETHOL), cyclophosphamide (NEOSAR, CYTOXAN), chlorambucil (LEUKERAN), cladribine (LEUSTATIN, MYLINAX), alpha-fetoprotein, etanercept (ENBREL), and 4-(benzyloxy)-5-[(5-undecyl-2H-pyrrol-2-ylidene)methyl]-1H,1'H-2,2'-bipyrrole (also known as PNU-156804);

(xxi) interferons, including interferon beta-1a (AVONEX, REBIF) and interferon beta-1b (BETASERON, BETAFERON);

(xxii) levodopa (or its methyl or ethyl ester), alone or in combination with a DOPA decarboxylase inhibitor (e.g., carbidopa (SINEMET, CARBILEV, PARCOPA), benserazide (MADOPAR), α-methyldopa, monofluoromethyldopa, difluoromethyldopa, brocresine, or m-hydroxybenzylhydrazine);

(xxiii) N-methyl-D-aspartate (NMDA) receptor antagonists, such as memantine (NAMENDA, AXURA, EBIXA), amantadine (SYMMETREL), acamprosate (CAMPRAL), besonprodil, ketamine (KETALAR), delucemine, dexanabinol, dexefaroxan, dextromethorphan, dextrorphan, traxoprodil, CP-283097, himantane, idantadol, ipenoxazone, L-701252 (Merck), lancicemine, levorphanol (DROMORAN), LY-233536 and LY-235959 (both Lilly), methadone, (DOLOPHINE), neramexane, perzinfotel, phencyclidine, tianeptine (STABLON), dizocilpine (also known as MK-801), EAB-318 (Wyeth), ibogaine, voacangine, tiletamine, riluzole (RILUTEK), aptiganel (CERESTAT), gavestinel, and remacimide;

(xxiv) monoamine oxidase (MAO) inhibitors, such as selegiline (EMSAM), selegiline hydrochloride (I-deprenyl, ELDEPRYL, ZELAPAR), dimethylselegiline, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), CHF-3381 (Chiesi Farmaceutici), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL);

(xxv) muscarinic receptor (particularly M1 subtype) agonists, such as cevimeline, levetiracetam, bethanechol chloride (DUVOID, URECHOLINE), itameline, pilocarpine (SALAGEN), NGX267, arecoline, L-687306 (Merck), L-689660 (Merck), furtrethonium iodide (FURAMON, FURANOL), furtrethonium benzensulfonate, furtrethonium p-toluenesulfonate, McN-A-343, oxotremorine, sabcomeline, AC-90222 (Acadia Pharmaceuticals), and carbachol (CARBASTAT, MIOSTAT, CARBOPTIC);

(xxvi) neuroprotective drugs such as bosutinib, condoliase, airmoclomol, lamotrigine, perampanel, aniracetam, minaprime, riluzole 2,3,4,9-tetrahydro-1H-carbazol-3-one oxime, desmoteplase, anatibant, astaxanthin, neuropeptide NAP (e.g., AL-108 and AL-208; both Alton Therapeutics), neurostrol, perampenel, ispronicline, bis(4-β-D-glucopyranosyloxybenzyl)-2-β-D-glucopyranosyl-2-isobutyltartrate (also known as dactylorhin B or DHB), formobactin, xaliproden (XAPRILA), lactacystin, dimeboline hydrochloride (DIMEBON), disufenton (CEROVIVE), arundic acid (ONO-2506, PROGLIA, CEREACT), citicoline (also known as cytidine 5'-diphosphocholine), edaravone (RADICUT), AEOL-10113 and AEOL-10150 (both Aeolus Pharmaceuticals), AGY-94806 (also known as SA-450 and Msc-1), granulocyte-colony stimulating factor (also known as AX-200), BAY-38-7271 (also known as KN-387271; Bayer AG), ancrod (VIPRINEX, ARWIN), DP-b99 (D-Pharm Ltd), HF-0220 (17-β-hydroxyepiandrosterone; Newron Pharmaceuticals), HF-0420 (also known as oligotropin), pyridoxal 5'-phosphate (also known as MC-1), microplasmin, S-18986, piclozotan, NP031112, tacrolimus, L-seryl-L-methionyl-L-alanyl-L-lysyl-L-glutamyl-glycyl-L-valine, AC-184897 (Acadia Pharmaceuticals), ADNF-14 (National Institutes of Health), stilbazulenyl nitrone, SUN-N8075 (Daiichi Suntory Biomedical Research), and zonampanel;

(xxvii) nicotinic receptor agonists, such as epibatidine, bupropion, CP-601927, varenicline, ABT-089 (Abbott), ABT-594, AZD-0328 (AstraZeneca), EVP-6124, R3487 (also known as MEM3454; Roche/Memory Pharmaceuticals), R4996 (also known as MEM63908; Roche/Memory Pharmaceuticals), TC-4959 and TC-5619 (both Targacept), and RJR-2403;

(xxviii) norepinephrine (noradrenaline) reuptake inhibitors, such as atomoxetine (STRATTERA), doxepin (APONAL, ADAPIN, SINEQUAN), nortriptyline (AVENTYL, PAMELOR, NORTRILEN), amoxapine (ASENDIN, DEMOLOX, MOXIDIL), reboxetine (EDRONAX, VESTRA), viloxazine (VIVALAN), maprotiline (DEPRILEPT, LUDIOMIL, PSYMION), bupropion (WELLBUTRIN), and radafaxine;

(xxix) phosphodiesterase (PDE) inhibitors, including (a) PDE1 inhibitors (e.g., vinpocetine (CAVINTON, CERACTIN, INTELECTOL) and those disclosed in U.S. Pat. No. 6,235,742, (b) PDE2 inhibitors (e.g., erythro-9-(2-hydroxy-3-nonyl)adenine (EHNA), BAY 60-7550, and those described in U.S. Pat. No. 6,174,884), (c) PDE3 inhibitors (e.g., anagrelide, cilostazol, milrinone, olprinone, parogrelil, and pimobendan), (d) PDE4 inhibitors (e.g., apremilast, roflumilast, rolipram, Ro 20-1724, ibudilast (KETAS), piclamilast (also known as RP73401), CDP840, cilomilast (ARIFLO), tofimilast, oglemilast (also known as GRC 3886), tetomilast (also known as OPC-6535), lirimifast, theophylline (UNIPHYL, THEOLAIR), arofylline (also known as LAS-31025), doxofylline, RPR-122818, or mesembrine), and (e) PDE5 inhibitors (e.g., sildenafil (VIAGRA®, REVATIO®), tadalafil (CIALIS®), vardenafil (LEVITRA®, VIVANZA®), udenafil, avanafil, dipyridamole (PERSANTINE), E-4010, E-4021, E-8010, zaprinast, iodenafil, mirodenafil, DA-8159, and those disclosed in International Patent Applications WO2002/020521, WO2005/049616, WO2006/120552, WO2006/126081, WO2006/126082, WO2006/126083, and WO2007/122466), (f) PDE9 inhibitors (e.g., BAY 73-6691 (Bayer AG) and those disclosed in US Patent Publication Nos US2003/0195205, US2004/0220186, US2006/0111372, US2006/0106035, and U.S. Ser. No. 12/118,062 (filed May 9, 2008)), and (g) PDE10 inhibitors such as 2-({4-[1-methyl-4-(pyridin-4-yl)-1H-pyrazol-3-yl]phenoxy}methyl)quinoline (PF-2545920), and SCH-1518291;

(xxx) quinolines, such as quinine (including its hydrochloride, dihydrochloride, sulfate, bisulfate and gluconate salts), chloroquine, sontoquine, hydroxychloroquine (PLAQUENIL), mefloquine (LARIAM), and amodiaquine (CAMOQUIN, FLAVOQUINE);

(xxxi) β-secretase inhibitors, such as ASP-1702, SCH-745966, JNJ-715754, AMG-0683, AZ-12304146, BMS-782450, GSK-188909, NB-533, LY-2886721, E-2609, HPP-854, (+)-phenserine tartrate (POSIPHEN), LSN-2434074 (also known as LY-2434074), KMI-574, SCH-745966, AcrER ($N^2$-acetyl-D-arginyl-L-arginine), loxistatin (also known as E64d), and CA074Me;

(xxxii) γ-secretase inhibitors and modulators, such as BMS-708163 (Avagacestat), WO20060430064 (Merck), DSP8658 (Dainippon), ITI-009, L-685458 (Merck), ELAN-G, ELAN-Z, 4-chloro-N-[2-ethyl-1(S)-(hydroxymethyl)butyl]benzenesulfonamide;

(xxxiii) serotonin (5-hydroxytryptamine) 1A (5-HT$_{1A}$) receptor antagonists, such as spiperone, levo-pindolol, BMY 7378, NAD-299, S(−)-UH-301, NAN 190, lecozotan;

(xxxiv) serotonin (5-hydroxytryptamine) 2C (5-HT$_{2C}$) receptor agonists, such as vabicaserin, and zicronapine;

(xxxv) serotonin (5-hydroxytryptamine) 4 (5-HT$_4$) receptor agonists, such as PRX-03140 (Epix);

(xxxvi) serotonin (5-hydroxytryptamine) 6 (5-HT$_6$) receptor antagonists, such as A-964324, AVI-101, AVN-211, mianserin (TOLVON, BOLVIDON, NORVAL), methiothepin (also known as metitepine), ritanserin, ALX-1161, ALX-1175, MS-245, LY-483518 (also known as SGS518; Lilly), MS-245, Ro 04-6790, Ro 43-68544, Ro 63-0563, Ro 65-7199, Ro 65-7674, SB-399885, SB-214111, SB-258510, SB-271046, SB-357134, SB-699929, SB-271046, SB-742457 (GlaxoSmithKline), Lu AE58054 (Lundbeck A/S), and PRX-07034 (Epix);

(xxxvii) serotonin (5-HT) reuptake inhibitors such as alaproclate, citalopram (CELEXA, CIPRAMIL), escitalopram (LEXAPRO, CIPRALEX), clomipramine (ANAFRANIL), duloxetine (CYMBALTA), femoxetine (MALEXIL), fenfluramine (PONDIMIN), norfenfluramine, fluoxetine (PROZAC), fluvoxamine (LUVOX), indalpine, milnacipran (IXEL), paroxetine (PAXIL, SEROXAT), sertraline (ZOLOFT, LUSTRAL), trazodone (DESYREL, MOLIPAXIN), venlafaxine (EFFEXOR), zimelidine (NORMUD, ZELMID), bicifadine, desvenlafaxine (PRISTIQ), brasofensine, vilazodone, cariprazine and tesofensine;

(xxxviii) trophic factors, such as nerve growth factor (NGF), basic fibroblast growth factor (bFGF; ERSOFERMIN), neurotrophin-3 (NT-3), cardiotrophin-1, brain-derived neurotrophic factor (BDNF), neublastin, meteorin, and glial-derived neurotrophic factor (GDNF), and agents that stimulate production of trophic factors, such as propentofylline, idebenone, PYM50028 (COGANE; Phytopharm), and AIT-082 (NEOTROFIN);

(xxxix) Glycine transporter-1 inhibitors such as paliflutine, ORG-25935, JNJ-17305600, and ORG-26041;

(xl) AMPA-type glutamate receptor modulators such as perampanel, mibampator, selurampanel, GSK-729327, and N-{(3S,4S)-4-[4-(5-cyanothiophen-2-yl)phenoxy]tetrahydrofuran-3-yl}propane-2-sulfonamide;

(xli) P450 inhibitors, such as ritonavir;

and the like.

The present invention further comprises kits that are suitable for use in performing the methods of treatment described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of the invention.

General Synthetic Schemes

The compounds of formula I, I-a, 1-b, 1-c, 1-d and 1-e, all generically described as the compounds of Formula I, may be prepared by the methods described below, together with synthetic methods known in the art of organic chemistry, or modifications and transformations that are familiar to those of ordinary skill in the art. The starting materials used herein are commercially available or may be prepared by routine methods known in the art [such as those methods disclosed in standard reference books such as the *Compendium of Organic Synthetic Methods*, Vol. I-XII (published by Wiley-Interscience)]. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999, which are hereby incorporated by reference.

Compounds of Formula I, or their pharmaceutically acceptable salts, can be prepared according to the reaction Schemes discussed herein below. Unless otherwise indicated, the substituents in the Schemes are defined as above. Isolation and purification of the products is accomplished by standard procedures, which are known to a chemist of ordinary skill.

One skilled in the art will recognize that in many cases, the compounds in Schemes 1 through 8 will be generated as a mixture of diastereomers and/or enantiomers; these may be separated at various stages of the synthetic schemes using conventional techniques or a combination of such techniques, such as, but not limited to, crystallization, normal-phase chromatography, reversed phase chromatography and chiral chromatography, to afford the single enantiomers of the invention.

It will be understood by one skilled in the art that the various symbols, superscripts and subscripts used in the schemes, methods and examples are used for convenience of representation and/or to reflect the order in which they are introduced in the schemes, and are not intended to necessarily correspond to the symbols, superscripts or subscripts in the appended claims. The schemes are representative of methods useful in synthesizing the compounds of the present invention. They are not to constrain the scope of the invention in any way.

Scheme 1 refers to the preparation of compounds of Formula I. Referring to Scheme 1, the compound of Formula I can be prepared from the compound of Formula II through a cyclization and removal of protecting group $P^1$. $P^1$ in this case refers to groups well known to those skilled in the art for amine protection. For example, $P^1$ may be a benzoyl group (Bz), which can be cleaved via acidic conditions, or through treatment with 1,8-diazabicyclo[5.4.0]undec-7-ene (DBU) in methanol. Alternatively $P^1$ may be 9-fluorenylmethoxycarbonyl (Fmoc), which can be cleaved under basic conditions. The cyclization of compounds of Formula II can be effected either under acidic conditions, for instance by heating in methanolic hydrochloric acid, or through the activation of the alcohol with a suitable activating group, such as methanesulfonyl (Ms).

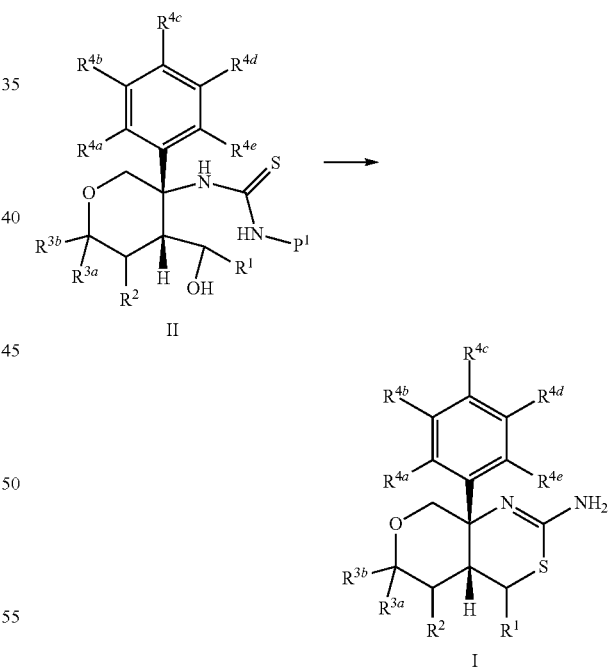

Scheme 2 refers to the preparation of compounds II wherein $P^1$ is Bz or Fmoc. Isoxazolidine III is converted to aminoalcohol IV via reductive cleavage of the N—O bond, for instance by the action of zinc powder in acetic acid. The disubstituted thiourea II is then generated by the thioacylation of IV using a reagent such as Bz-protected isothiocyanate or Fmoc-protected isothiocyanate. Compound II can be converted into a compound of Formula I according to the methods of Scheme 1.

Scheme 2

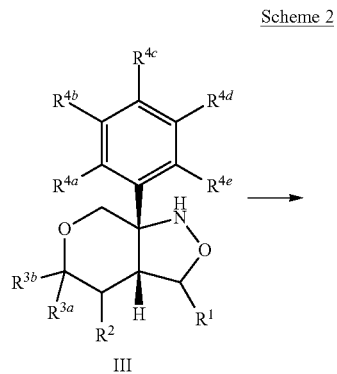
III

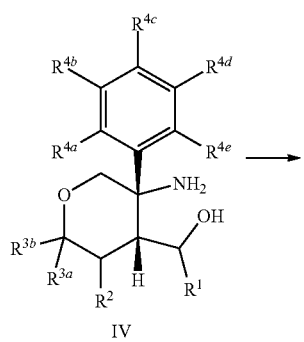
IV

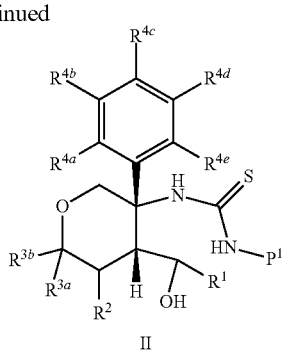
II

Scheme 3 refers to the preparation of compound III. Homoallylic alcohol V is alkylated with 2-bromo-1,1-dimethoxyethane under basic conditions, such as treatment with potassium hydride, to provide the corresponding ether VI. The acetal is cleaved under acidic conditions, aqueous HCl as an example, to give aldehyde VII. Condensation with a hydroxylamine salt, such as hydroxylammonium bisulfate, provides geometric mixtures of the corresponding oxime IX. Cycloaddition to form isoxazoline X may be carried out by treatment of oxime IX with an oxidizing agent, such as sodium hypochlorite. Reaction of isoxazoline X with an appropriate arylmetallic reagent (for instance, an aryllithium such as 2,4-difluorophenyllithium, or an aryl Grignard reagent) at low temperature, e.g., −78° C., yields compounds of Formula III. One of ordinary skilled in the art would recognize that the stereochemistry of addition of the arylmetallic reagent is determined by the stereochemistry of the adjacent methine center, yielding a racemic mixture of cis-fused diastereomers, which can be converted into compounds of Formula I according to the methods of Schemes 1 and 2

Scheme 3

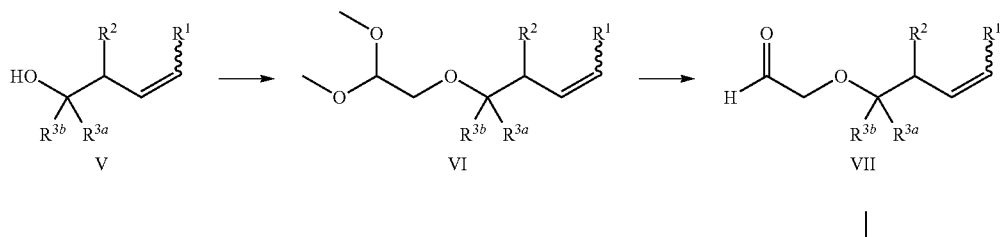

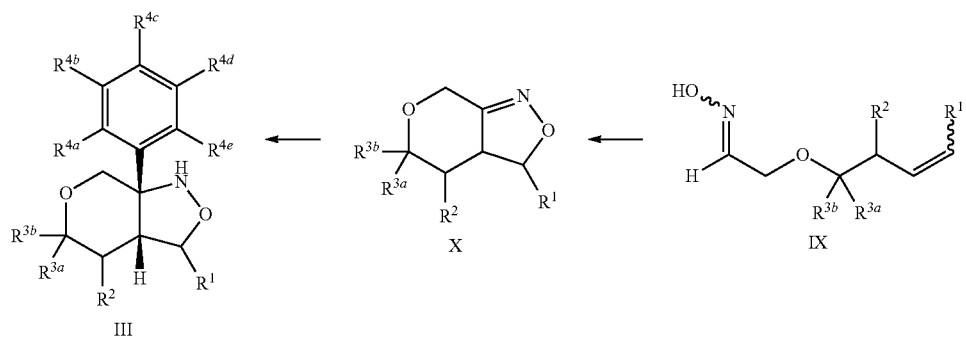

Alternatively, compounds of Formula III can be prepared as described in Scheme 4. Homoallylic alcohol V can be alkylated with tert-butyl bromoacetate under basic conditions, such as treatment with sodium hydride. The tert-butyl ester XI can be hydrolyzed under acidic conditions, such as treatment with hydrochloric acid, to the corresponding carboxylic acid XII. The carboxylic acid XII is then suitably activated, for instance via generation of the acid chloride through treatment with thionyl chloride, and subsequently treated with a preferred amine, such as N,O-dimethylhydroxylamine, to provide the corresponding amide XIII (morpholine is another preferred amine). Reaction of amide XIII with the appropriate arylmetallic reagent (for instance, an aryllithium such as 2,4-difluorophenyllithium, or an aryl Grignard reagent) at low temperature, e.g., −78° C., provides the corresponding ketone XIV. Condensation with a hydroxylamine salt, such as hydroxylammonium bisulfate, provides geometric mixtures of the corresponding oxime XV. Cycloaddition can then be directly effected by heating oxime XV in an appropriate solvent, such as xylenes, to yield isoxazolidine III. Isoxazolidine III can be converted to compounds of Formula I according to Schemes 1 and 2.

Compounds of Formula VII can also be prepared as depicted in Scheme 5. Activation of an appropriately substituted homoallylic alcohol V, for instance via conversion of the alcohol to a bromide or Ms group (indicated as LV), provides compound Va. Homoallylic alcohols such as compound V may generally be prepared by an asymmetric allylation reaction [S. E. Denmark and N. G. Almstead, *Modern Carbonyl Chemistry*, Otera, J., Ed.; Wiley-VCH: Weinheim, 2000, pp 299-401]. Treatment of glycol XVI, monosubstituted with a suitable protecting group, such as tert-butyldimethylsilyl (TBDMS), with an appropriate base, such as sodium hydride, followed by reaction with reagent Va, provides protected alcohol XVII, which can be deprotected using standard methods, such as treatment with tetrabutylammonium fluoride (TBAF), to afford alcohol XVIII. Subsequent oxidation, for example through reaction with Dess-Martin periodinane, provides the corresponding aldehyde VII. If appropriate, ethylene glycol can be used in place of monoprotected diol XVI; this would remove the need for a deprotection step. Aldehyde VII can then be further converted to compounds of Formula I according to Schemes 1, 2 and 3.

Scheme 4

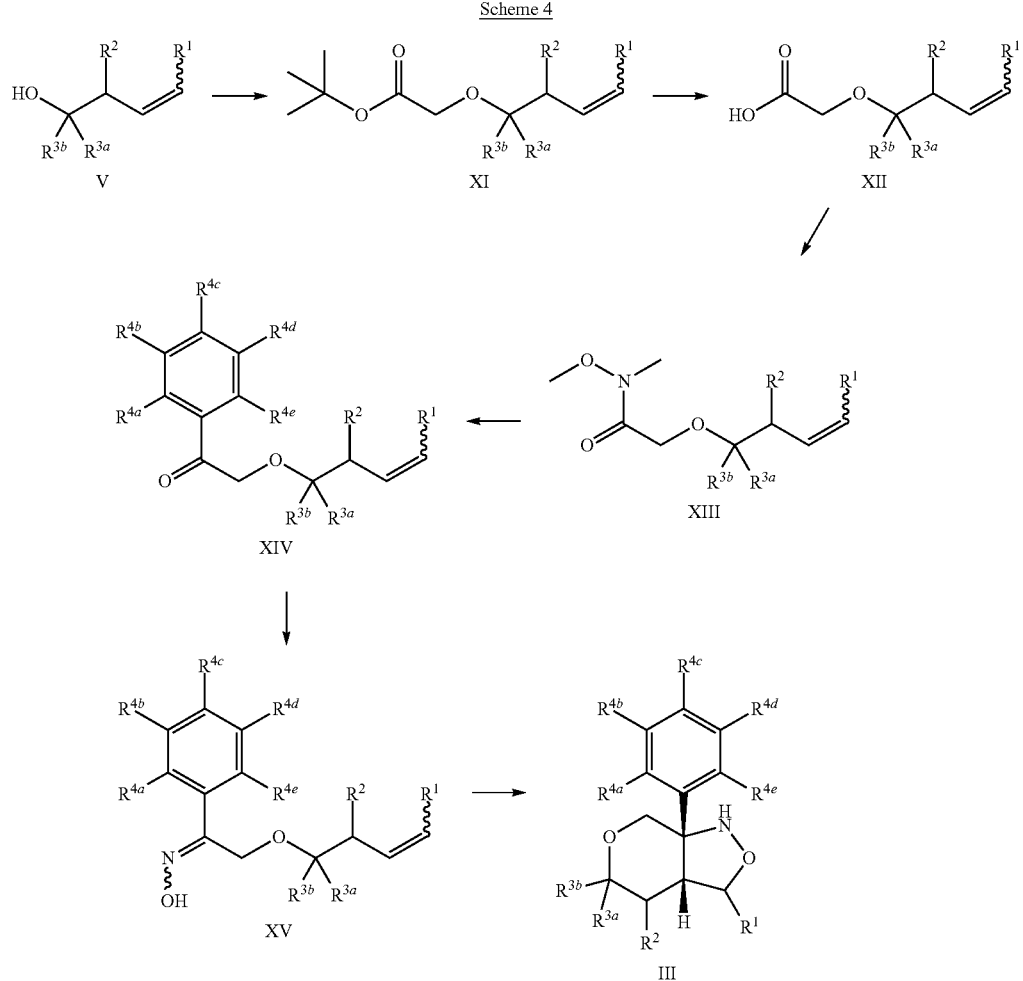

Scheme 5

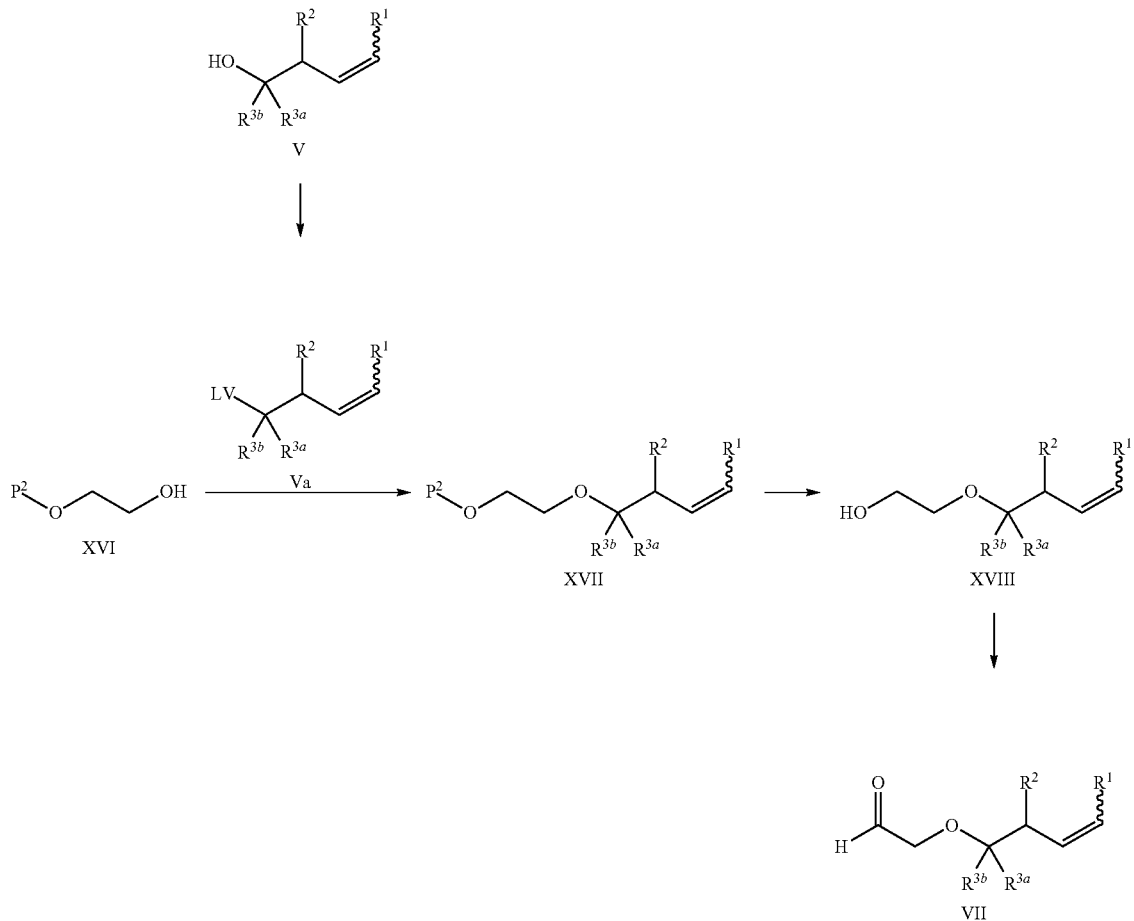

Scheme 6 refers to an alternative installation of an $R^1$ group. The amine of aminoalcohol IV, wherein $R^1$=H, can be protected with an appropriate protecting group $P^2$, such as tert-butoxycarbonyl (Boc), to afford compounds of Formula XIX. The primary alcohol of XIX can be oxidized to the corresponding aldehyde XX under Swern or Dess-Martin conditions; addition of a Grignard reagent $R^1$MgX then affords the secondary alcohol XXI. Deprotection of the Boc group using a strong acid, such as trifluoroacetic acid (TFA), provides amino alcohol IV wherein $R^1$≠H, which can be converted to compounds of Formula I via Schemes 1 and 2.

Scheme 6

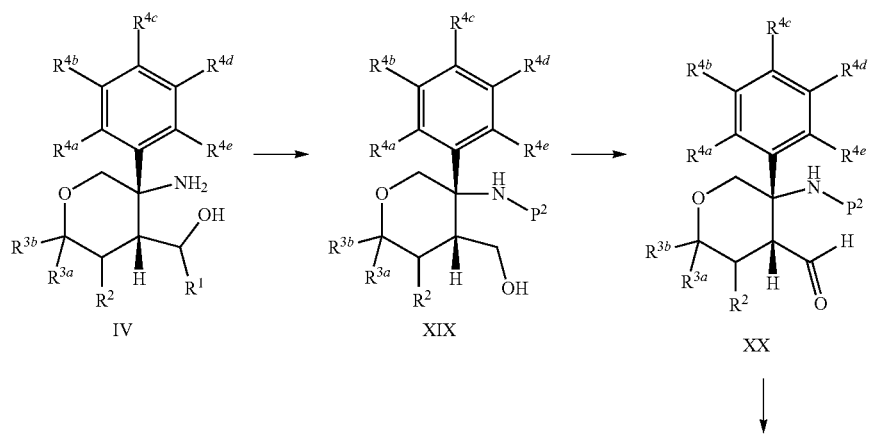

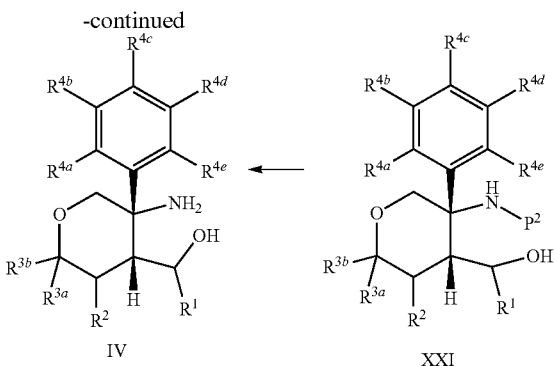

Scheme 7 refers to an alternate preparation of compounds of Formula I. Treatment of beta-ketoester XXII with an appropriate base, such as lithium diisopropylamide, followed by trifluoroacetic acid anhydride (TFAA), yields vinyl triflate XXIII. Reaction of vinyl triflate XXIII with the appropriate aryl boronic acid under standard Suzuki reaction conditions [A. Suzuki, *J. Organomet. Chem.* 1999, 576, 147-168; N. Miyaura and A. Suzuki, *Chem. Rev.* 1995, 95, 2457-2483] provides compounds of Formula XXIV. Reduction of the methyl ester using standard conditions, such as reduction with diisobutylaluminum hydride, provides the primary alcohol XXV. Activation to a suitable leaving group LV, for instance via treatment with trifluoroacetic anhydride, provides compounds of Formula XXVI. Subsequent displacement with thiourea provides the primary amidine XXVII, which can be closed upon treatment with a suitable acid, such as TFA, to afford thioamidine XXVIII. One skilled in the art will recognize that the product of this transformation will be a mixture of diastereomers and enantiomers that may be separated using conventional techniques, such as, but not limited to, crystallization, normal-phase chromatography, reversed phase chromatography and chiral chromatography, to afford compounds of Formula I wherein $R^1$ is H.

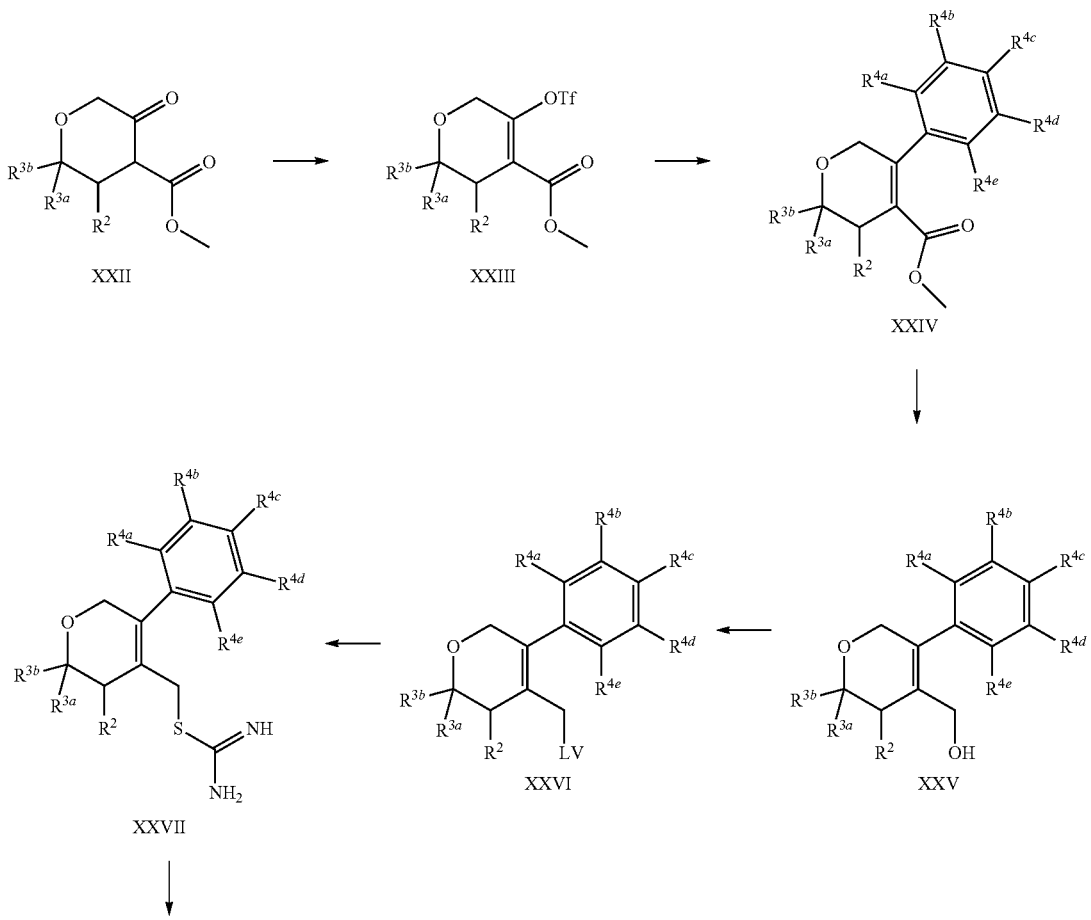

Scheme 7

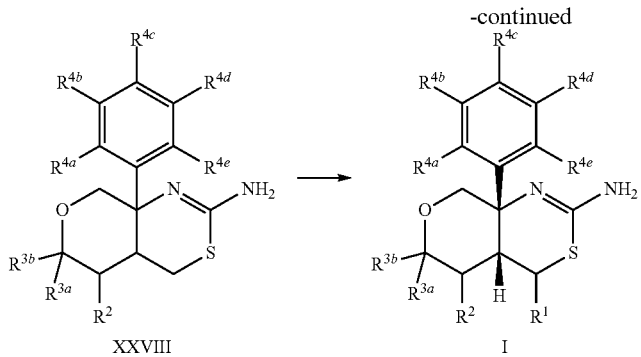

Scheme 8 shows an alternate preparation of compound XXVI. Subjecting vinyl triflate XXIX to standard Suzuki reaction conditions with the appropriate aryl boronic acid provides compounds of Formula XXVI, which can be converted to compounds of Formula I via Scheme 7.

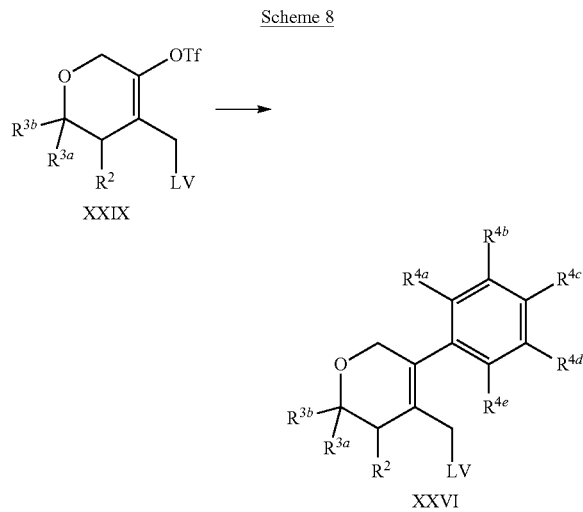

Experimental Procedures and Working Examples

The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification, including anhydrous solvents where appropriate (generally Sure-Seal™ products from the Aldrich Chemical Company, Milwaukee, Wis.). Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed.

For syntheses referencing procedures in other Examples or Methods, reaction conditions (length of reaction and temperature) may vary. In general, reactions were followed by thin layer chromatography or mass spectrometry, and subjected to work-up when appropriate. Purifications may vary between experiments: in general, solvents and the solvent ratios used for eluants/gradients were chosen to provide appropriate $R_f$s or retention times.

Preparation 1: (3aR,5R)-5-[(Benzyloxy)methyl]-3,3a,4,5-tetrahydro-7H-pyrano[3,4-c][1,2]oxazole (P1)

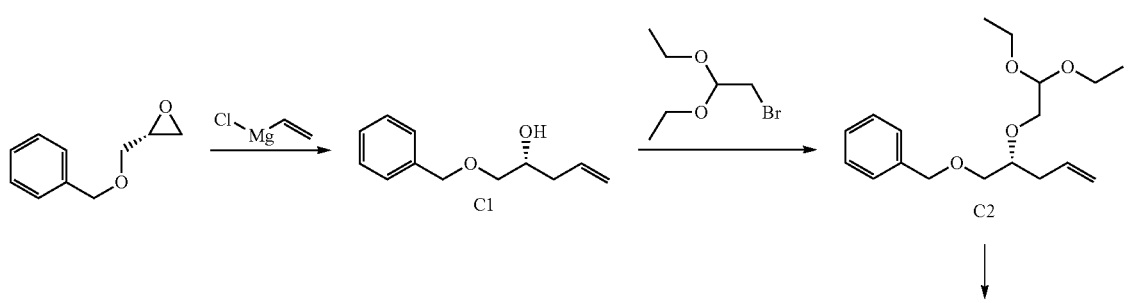

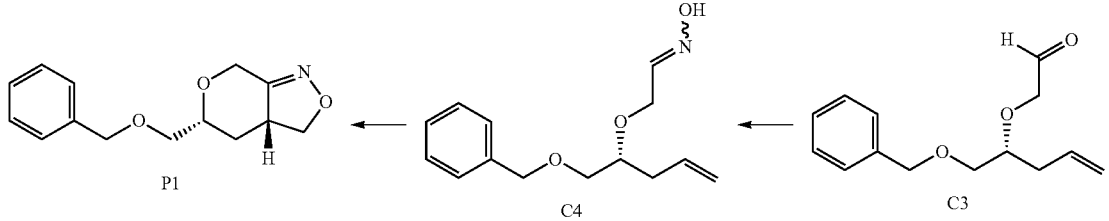

Step 1. Synthesis of (2R)-1-(benzyloxy)pent-4-en-2-ol (C1)

A mixture of (2R)-2-[(benzyloxy)methyl]oxirane (9.8 g, 60 mmol) and copper(I) iodide (648 mg, 3.40 mmol) in diethyl ether (150 mL) was cooled to −78° C. Vinylmagnesium chloride (1.6 M solution in tetrahydrofuran; 41.0 mL, 65.6 mmol) was added drop-wise, and the reaction mixture was allowed to warm slowly to room temperature and stir for 18 hours. Ice and saturated aqueous ammonium chloride solution were added, and the mixture was extracted with ethyl acetate. The combined organic layers were washed with aqueous ammonium chloride solution, dried over magnesium sulfate, filtered and concentrated in vacuo. This material was used in the following step without further purification. $^1$H NMR (400 MHz, CDCl$_3$), product peaks only: δ 2.25-2.31 (m, 2H), 3.39 (dd, J=9.4, 7.4 Hz, 1H), 3.53 (dd, J=9.5, 3.4 Hz, 1H), 3.87-3.93 (m, 1H), 4.57 (s, 2H), 5.09-5.16 (m, 2H), 5.78-5.89 (m, 1H), 7.3-7.4 (m, 5H).

Step 2. Synthesis of ({[(2R)-2-(2,2-diethoxyethoxy)pent-4-en-1-yl]oxy}methyl)benzene (C2)

A solution of (2R)-1-(benzyloxy)pent-4-en-2-ol (C1) (material from the previous step, ≤60 mmol) in tetrahydrofuran (50 mL) was added drop-wise to a suspension of sodium hydride (60% in mineral oil, 11.0 g, 275 mmol) in tetrahydrofuran (100 mL) at 0° C. After the reaction mixture had stirred for 30 minutes at this temperature, a solution of 2-bromo-1,1-diethoxyethane (97%, 13.3 mL, 85.8 mmol) in tetrahydrofuran (50 mL) was added at 0° C., and the reaction mixture was heated at reflux for 18 hours. Additional 2-bromo-1,1-diethoxyethane (11 mL, 71 mmol) was added, and heating was continued for a further 24 hours. The reaction mixture was cooled to 0° C., quenched with water, and extracted three times with ethyl acetate. The combined organic layers were washed with water, washed with saturated aqueous sodium chloride solution, dried over sodium sulfate, filtered, and concentrated in vacuo. Chromatography on silica gel (Gradient: 0% to 15% ethyl acetate in heptane) afforded the product as a colorless oil. Yield: 11.04 g, 35.80 mmol, 60% over 2 steps. $^1$H NMR (400 MHz, CDCl$_3$) δ 1.21 (t, J=7.1 Hz, 3H), 1.22 (t, J=7.0 Hz, 3H), 2.31-2.36 (m, 2H), 3.49-3.74 (m, 9H), 4.55 (s, 2H), 4.61 (t, J=5.3 Hz, 1H), 5.02-5.12 (m, 2H), 5.78-5.90 (m, 1H), 7.27-7.38 (m, 5H).

Step 3. Synthesis of {[(2R)-1-(benzyloxy)pent-4-en-2-yl]oxy}acetaldehyde (C3)

({[(2R)-2-(2,2-Diethoxyethoxy)pent-4-en-1-yl]oxy}methyl)benzene (C2) (10.14 g, 32.88 mmol) was dissolved in tetrahydrofuran (110 mL). Aqueous hydrochloric acid (2 M, 19.5 mL, 39.0 mmol) was added, and the reaction mixture was heated at 75° C. for 1 hour. The reaction was concentrated to approximately half the original volume and then partitioned between ethyl acetate and water. The aqueous layer was extracted with ethyl acetate, and the combined organic layers were washed with saturated aqueous sodium chloride solution, dried over sodium sulfate, filtered, and concentrated under reduced pressure. The product was obtained as a colorless oil, which was used directly in the following step. Yield: 7.76 g. $^1$H NMR (400 MHz, CDCl$_3$) δ 2.28-2.42 (m, 2H), 3.54-3.57 (m, 2H), 3.62-3.68 (m, 1H), 4.18-4.28 (m, 2H), 4.53 (br s, 2H), 5.06-5.15 (m, 2H), 5.78-5.89 (m, 1H), 7.27-7.39 (m, 5H), 9.72 (t, J=1.0 Hz, 1H).

Step 4. Synthesis of 2-{[(2R)-1-(benzyloxy)pent-4-en-2-yl]oxy}-N-hydroxyethanimine (C4)

{[(2R)-1-(Benzyloxy)pent-4-en-2-yl]oxy}acetaldehyde (C3) (7.76 g, ≤32.88 mmol) was dissolved in a 2:1 mixture of ethanol and water (127 mL). Sodium acetate (13.6 g, 166 mmol) was added, and the mixture was stirred for 15 minutes. Hydroxylamine hydrochloride (98%, 7.05 g, 99.4 mmol) was then added, and the reaction mixture was heated to 60° C. for 18 hours. The reaction mixture was partitioned between ethyl acetate and water; the aqueous layer was extracted with ethyl acetate, and the combined organic layers were washed with saturated aqueous sodium chloride solution, dried over sodium sulfate, filtered, and concentrated in vacuo. Silica gel chromatography (Gradient: 0% to 30% ethyl acetate in heptane) afforded the product as a colorless oil, presumed from the $^1$H NMR spectrum to be a mixture of E and Z oximes. Yield: 7.12 g, 28.6 mmol, 87% over two steps. $^1$H NMR (400 MHz, CDCl$_3$) δ 2.30-2.37 (m, 2H), 3.47-3.65 (m, 3H), {[4.20 (dd, half of ABX pattern, J=12.9, 5.8 Hz) and 4.25 (dd, half of ABX pattern, J=12.9, 5.6 Hz)] and 4.45-4.49 (br m), total 2H}, 4.55 and 4.56 (2 s, total 2H), 5.05-5.14 (m, 2H), 5.75-5.87 (m, 1H), 6.93-7.01 and 7.47-7.55 (2 br m, total 1H), 7.27-7.39 (m, 5H).

Step 5. Synthesis of (3aR,5R)-5-[(benzyloxy)methyl]-3,3a,4,5-tetrahydro-7H-pyrano[3,4-c][1,2]oxazole (P1)

A solution of 2-{[(2R)-1-(benzyloxy)pent-4-en-2-yl]oxy}-N-hydroxyethanimine (C4) (7.12 g, 28.6 mmol) in dichloromethane (168 mL) was placed in a room temperature water bath. Triethylamine (0.299 mL, 2.14 mmol) was added, followed by addition of bleach (aqueous sodium hypochlorite solution, 6.15%, 71 mL, 59 mmol) at a rate slow enough to maintain the internal reaction temperature between 22° C. and 25.5° C. Upon completion of the addition, the reaction mixture was diluted with water and extracted three times with dichloromethane. The combined organic extracts were washed with saturated aqueous sodium chloride solution, dried over sodium sulfate, filtered, and concentrated under reduced pressure. Purification via silica gel chromatography (Gradient: 0% to 35% ethyl acetate in heptane) provided the product as a yellow oil. The indicated relative stereochemistry of compound P1 was assigned based on nuclear Overhauser enhancement studies, which revealed an interaction between the methine protons on carbons 3a and 5. Yield: 5.65 g, 22.8 mmol, 80%. LCMS m/z 248.1 (M+1). ¹H NMR (400 MHz, CDCl₃) δ 1.51-1.63 (m, 1H), 2.17-2.24 (m, 1H), 3.40-3.52 (m, 1H), 3.49 (dd, half of ABX pattern, J=10.2, 4.2 Hz, 1H), 3.57 (dd, half of ABX pattern, J=10.2, 5.8 Hz, 1H), 3.68-3.77 (m, 1H), 3.79 (dd, J=11.8, 8.1 Hz, 1H), 4.23 (dd, J=13.5, 1.2 Hz, 1H), 4.54-4.65 (m, 3H), 4.77 (d, J=13.5 Hz, 1H), 7.27-7.39 (m, 5H).

Example 1

(4aR,8aS)-8a-(2,4-Difluorophenyl)-4,4-a,5,6,8,8a-hexahydropyrano[3,4-d][1,3]thiazin-2-amine (1)

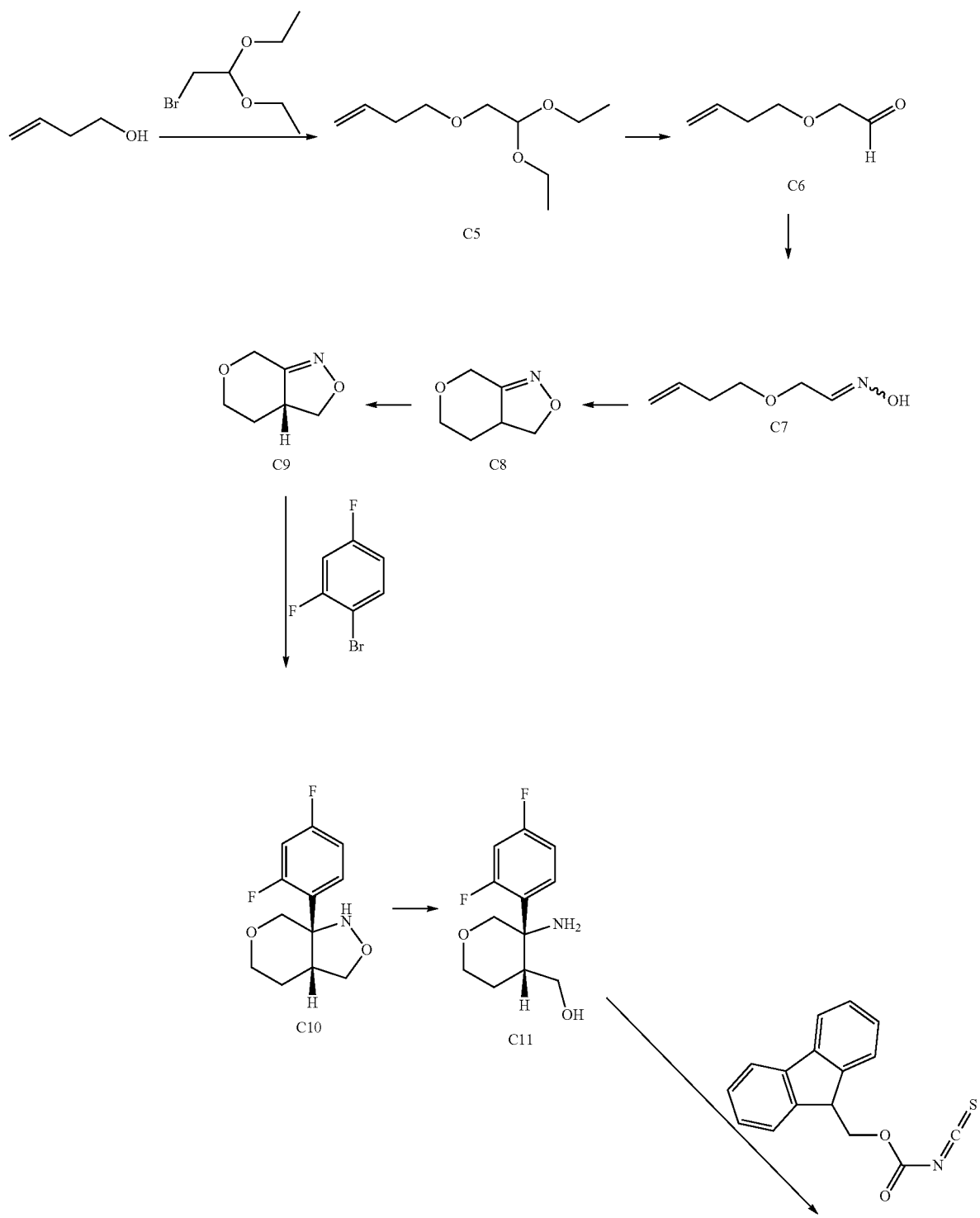

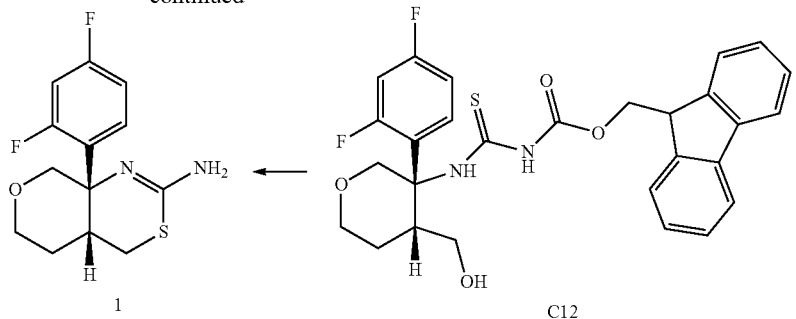

Step 1. Synthesis of 4-(2,2-diethoxyethoxy)but-1-ene (C5)

A solution of but-3-en-1-ol (96%, 28.0 mL, 312 mmol) in tetrahydrofuran (150 mL) was added to a suspension of sodium hydride (60% in mineral oil, 59.9 g, 1.50 mol) in tetrahydrofuran (700 mL) at 0° C. After the reaction mixture had stirred for 30 minutes at this temperature, a solution of 2-bromo-1,1-diethoxyethane (97%, 72.6 mL, 468 mmol) in tetrahydrofuran (150 mL) was added at 0° C., and the reaction mixture was heated to 68° C. for 66 hours. The reaction mixture was cooled to 0° C., slowly quenched with water (150 mL), and concentrated in vacuo to remove tetrahydrofuran. After three extractions with ethyl acetate, the combined organic layers were dried over magnesium sulfate, filtered, and concentrated in vacuo to afford the product as an oil, which was taken directly to the following step. Yield: 77 g. $^1$H NMR (400 MHz, CDCl$_3$), product peaks only: δ 1.23 (t, J=7.0 Hz, 6H), 2.32-2.38 (m, 2H), 3.50 (d, J=5.3 Hz, 2H), 3.53-3.62 (m, 4H), 3.67-3.75 (m, 2H), 4.63 (t, J=5.3 Hz, 1H), 5.02-5.06 (m, 1H), 5.07-5.13 (m, 1H), 5.77-5.88 (m, 1H).

Step 2. Synthesis of (but-3-en-1-yloxy)acetaldehyde (C6)

A solution of 4-(2,2-diethoxyethoxy)but-1-ene (C5) (77 g from the preceding step, ≤312 mmol) in tetrahydrofuran (515 mL) was treated with aqueous hydrochloric acid (2 M, 105 mL); the reaction mixture was then brought to 70° C. and maintained at that temperature for 30 minutes. After cooling to room temperature, removal of solvents in vacuo afforded the product as an amber oil, which was taken directly to the following step. Yield: 40 g.

Step 3. Synthesis of 2-(but-3-en-1-yloxy)-N-hydroxyethanimine (C7)

(But-3-en-1-yloxy)acetaldehyde (C6) (40 g from the preceding step, ≤312 mmol) was dissolved in a 2:1 mixture of ethanol and water (700 mL). Sodium acetate (128 g, 1560 mmol) was added, and the mixture was stirred for 20 minutes. Hydroxylamine hydrochloride (98%, 66.4 g, 936 mmol) was then added, and the reaction mixture was heated to 60° C. for 18 hours, at which point it was cooled to room temperature and concentrated under reduced pressure to remove ethanol. The aqueous residue was poured into water (500 mL) and extracted four times with ethyl acetate. The combined organic layers were dried over magnesium sulfate, filtered, and concentrated in vacuo. Silica gel chromatography (Gradient: 0% to 40% ethyl acetate in heptane) afforded the product as an oil, presumed from the $^1$H NMR spectrum to be a mixture of E and Z oximes. Yield: 24 g, 0.19 mmol, 60% over three steps. $^1$H NMR (400 MHz, CDCl$_3$) δ 2.33-2.41 (m, 2H), 3.51-3.57 (m, 2H), [4.11 (d, J=5.7 Hz) and 4.36 (d, J=3.7 Hz), total 2H], 5.04-5.16 (m, 2H), 5.76-5.89 (m, 1H), [6.92 (t, J=3.7 Hz) and 7.51 (t, J=5.6 Hz), total 1H].

Step 4. Synthesis of 3,3a,4,5-tetrahydro-7H-pyrano[3,4-c][1,2]oxazole (C8)

Compound C8 was prepared from 2-(but-3-en-1-yloxy)-N-hydroxyethanimine (C7) according to the general procedure for the synthesis of (3aR,5R)-5-[(benzyloxy)methyl]-3,3a,4,5-tetrahydro-7H-pyrano[3,4-c][1,2]oxazole (P1) in Preparation 1. The product was obtained as a yellow oil. Yield: 4.1 g, 32 mmol, 77%; 85% yield based on recovered starting material. $^1$H NMR (400 MHz, CDCl$_3$) δ 1.73-1.84 (m, 1H), 2.13-2.20 (m, 1H), 3.34-3.45 (m, 1H), 3.50 (ddd, J=12.3, 12.1, 2.0 Hz, 1H), 3.79 (dd, J=11.6, 8.1 Hz, 1H), 4.03-4.09 (m, 1H), 4.12 (dd, J=13.5, 1.2 Hz, 1H), 4.62 (dd, J=10.2, 8.0 Hz, 1H), 4.70 (br d, J=13 Hz, 1H).

Step 5. Isolation of (3aR)-3,3a,4,5-tetrahydro-7H-pyrano[3,4-c][1,2]oxazole (C9)

The enantiomers of 3,3a,4,5-tetrahydro-7H-pyrano[3,4-c][1,2]oxazole (C8) (4.1 g, 32 mmol) were separated using supercritical fluid chromatography (Column: Chiralpak AS-H, 5 μm; Eluent: 95:5 CO$_2$/2-propanol). The second-eluting enantiomer, obtained as an oil, was of the desired absolute stereochemistry (C9). Yield: 1.2 g, 9.4 mmol, 30%. LCMS m/z 128.0 (M+1). $^1$H NMR (400 MHz, CD$_3$OD) δ 1.63-1.75 (m, 1H), 2.15-2.22 (m, 1H), 3.44-3.53 (m, 1H), 3.54 (ddd, J=12.3, 12.3, 1.9 Hz, 1H), 3.73 (dd, J=11.5, 8.0 Hz, 1H), 3.96-4.02 (m, 1H), 4.16 (dd, J=13.3, 1.2 Hz, 1H), 4.52-4.61 (m, 2H). The indicated absolute stereochemistry of C9 was elucidated via conversion of C9 to Example 1, and the conversion of the enantiomer of C9 (the first-eluting enantiomer from the Chiralpak column) to Example 20; as shown in Table 7, Example 1 displays activity against the BACE1 enzyme while Example 20 does not. The absolute stereochemistry of C9 (and, by extension, that of Example 1 and other compounds derived from C9) was therefore assigned to correlate with that of compound C17 (precursor to biologically active Example 2), which was determined via single crystal X-ray analysis (vide infra). The enantiomer of C9 eluted first from the column, and was obtained as an oil. Yield: 1.1 g, 8.6 mmol, 27%. LCMS m/z 128.0 (M+1). $^1$H NMR (400 MHz, CD$_3$OD) δ 1.63-1.75 (m, 1H), 2.15-2.22 (m, 1H), 3.44-3.55 (m, 1H), 3.54 (ddd, J=12.3, 12.3, 1.8 Hz, 1H), 3.73 (dd, J=11.5, 8.0 Hz, 1H), 3.97-4.02 (m, 1H), 4.16 (dd, J=13.2, 1.3 Hz, 1H), 4.52-4.61 (m, 2H).

Step 6. Synthesis of (3aR,7aS)-7a-(2,4-difluorophenyl)hexahydro-1H-pyrano[3,4-c][1,2]oxazole (C10)

n-Butyllithium (2.5 M solution in hexanes, 3.95 mL, 9.88 mmol) was added to a solution of 1-bromo-2,4-difluorobenzene (0.558 mL, 4.94 mmol) in a 1:3 mixture of tetrahydrofuran and toluene (25 mL) at −78° C., and the reaction mixture was stirred at this temperature for 1 hour. In a separate flask, a solution of (3aR)-3,3a,4,5-tetrahydro-7H-pyrano[3,4-c][1,2]oxazole (C9) (628 mg, 4.94 mmol) in toluene (15 mL) was cooled to −78° C. and treated with boron trifluoride diethyl etherate (1.22 mL, 9.88 mmol); this mixture was also allowed to stir at −78° C. for 1 hour, and then added via cannula to the aryllithium solution. The reaction mixture was stirred for 1 hour and was then quenched with saturated aqueous ammonium chloride solution. After dilution with ethyl acetate, the layers were separated, and the organic layer was washed with saturated aqueous sodium chloride solution, dried over magnesium sulfate, filtered, and concentrated in vacuo. Chromatography on silica gel (Gradient: 0% to 40% ethyl acetate in heptane) provided the product. Yield: 610 mg, 2.53 mmol, 51%. The cis ring fusion was assigned on the basis of analogy with compound C17, whose stereochemistry was confirmed via single crystal X-ray analysis (vide infra). LCMS m/z 242.0 (M+1). $^1$H NMR (400 MHz, CD$_3$OD) δ 1.75-1.93 (m, 2H), 3.03-3.10 (m, 1H), 3.53-3.76 (m, 4H), 3.95-4.02 (br m, 1H), 4.03 (dd, J=12.5, 1.8 Hz, 1H), 6.93-7.00 (m, 2H), 7.84-7.92 (m, 1H).

Step 7. Synthesis of [(3S,4R)-3-amino-3-(2,4-difluorophenyl)tetrahydro-2H-pyran-4-yl]methanol (C11)

(3aR,7aS)-7a-(2,4-Difluorophenyl)hexahydro-1H-pyrano [3,4-c][1,2]oxazole (C10) (1.06 g, 4.39 mmol) was mixed with acetic acid (10 mL); after addition of zinc powder (3.74 g, 57.2 mmol), the reaction mixture was stirred for 18 hours. Insoluble material was removed via filtration, and the filtrate was concentrated under reduced pressure. The resulting paste was taken up in ethyl acetate, washed with saturated aqueous sodium bicarbonate solution, washed with saturated aqueous sodium chloride solution, and dried over magnesium sulfate. Filtration and removal of solvent under reduced pressure provided the product. Yield: 900 mg, 3.70 mmol, 84%. $^1$H NMR (400 MHz, CD$_3$OD) δ 1.71-1.78 (m, 1H), 2.00-2.12 (m, 1H), 2.40-2.48 (m, 1H), 3.37-3.40 (m, 2H), 3.50 (d, J=11.5 Hz, 1H), 3.62 (ddd, J=12.7, 11.5, 2.7 Hz, 1H), 4.01 (dd, J=11.3, 2.0 Hz, 1H), 4.09-4.15 (m, 1H), 6.96-7.05 (m, 2H), 7.64-7.71 (m, 1H).

Step 8. Synthesis of 9H-fluoren-9-ylmethyl {[(3S, 4R)-3-(2,4-difluorophenyl)-4-(hydroxymethyl)tetrahydro-2H-pyran-3-yl]carbamothioyl}carbamate (C12)

9H-Fluoren-9-ylmethyl carbonisothiocyanatidate (Fmoc-isothiocyanate) (827 mg, 2.94 mmol) was added to a solution of [(3S,4R)-3-amino-3-(2,4-difluorophenyl)tetrahydro-2H-pyran-4-yl]methanol (C11) (650 mg, 2.67 mmol) in dichloromethane (10 mL), and the reaction mixture was allowed to stir for 4 hours at room temperature. Removal of solvent in vacuo provided a paste, which was purified via silica gel chromatography (Gradient: 0% to 5% methanol in dichloromethane) to afford the product. Yield: 1.17 g, 2.23 mmol, 84%. LCMS m/z 525.2 (M+1).

Step 9. Synthesis of (4aR,8aS)-8a-(2,4-difluorophenyl)-4,4-a,5,6,8,8a-hexahydropyrano[3,4-c][1,3] thiazin-2-amine (1)

A suspension of 9H-fluoren-9-ylmethyl {[(3S,4R)-3-(2,4-difluorophenyl)-4-(hydroxymethyl)tetrahydro-2H-pyran-3-yl]carbamothioyl}carbamate (C12) (1.417 g, 2.701 mmol) in methanol (20 mL) was treated with concentrated hydrochloric acid (12 M, 0.675 mL, 8.10 mmol) and heated at 70° C. for 2 hours. The reaction mixture was concentrated in vacuo, dissolved in dichloromethane and washed with saturated aqueous sodium bicarbonate solution. The organic layer was dried over magnesium sulfate, filtered, and concentrated under reduced pressure. The residue was dissolved in acetonitrile (20 mL) and treated with piperidine (2 mL); this reaction mixture was stirred at room temperature for 18 hours, and then concentrated in vacuo. Purification via silica gel chromatography (Gradient: 0% to 7% methanol in dichloromethane) provided the product as a white solid. Yield: 281 mg, 0.988 mmol, 37%. LCMS m/z 285.0 (M+1). $^1$H NMR (400 MHz, CD$_3$OD) δ 1.45-1.52 (m, 1H), 1.99-2.12 (m, 1H), 2.67-2.73 (m, 1H), 2.82-2.90 (m, 2H), 3.62-3.70 (m, 1H), 3.63 (br d, J=10.9 Hz, 1H), 3.99-4.05 (m, 2H), 6.92-7.00 (m, 2H), 7.35 (ddd, J=9.5, 8.7, 6.7 Hz, 1H).

Example 2

(4aR,6R,8aS)-8a-(2-Fluorophenyl)-6-[(propan-2-yloxy)methyl]-4,4-a,5,6,8,8a-hexahydropyrano[3,4-d][1,3]thiazin-2-amine, trifluoroacetate salt (2)

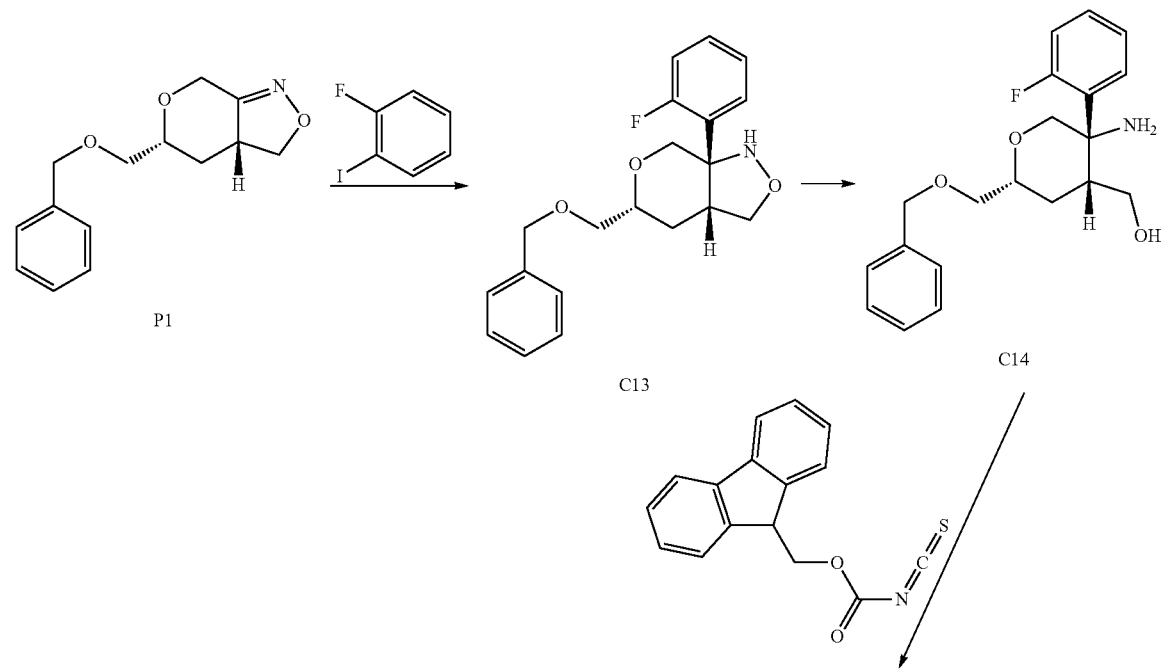

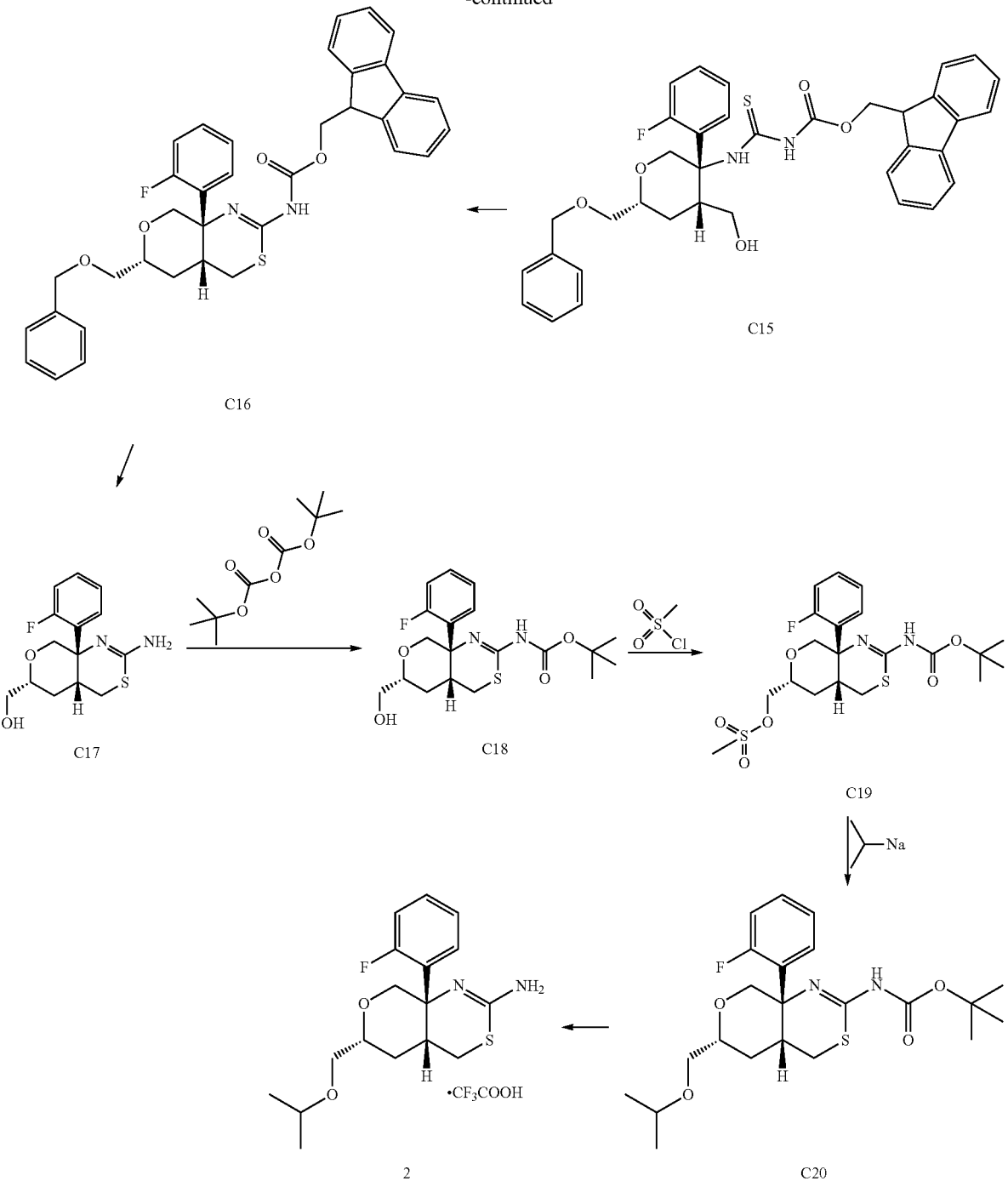

Step 1. Synthesis of (3aR,5R,7aS)-5-[(benzyloxy)methyl]-7a-(2-fluorophenyl)hexahydro-1H-pyrano[3,4-c][1,2]oxazole (C13)

n-Butyllithium (2.5 M solution in hexanes, 11.3 mL, 28.3 mmol) was added in a drop-wise manner to a solution of 1-fluoro-2-iodobenzene (3.30 mL, 28.3 mmol) in a mixture of tetrahydrofuran (26 mL) and toluene (116 mL) at −78° C., and the reaction mixture was stirred at this temperature for 30 minutes. In a separate flask, a solution of (3aR,5R)-5-[(benzyloxy)methyl]-3,3a,4,5-tetrahydro-7H-pyrano[3,4-c][1,2]oxazole (P1) (3.50 g, 14.2 mmol) in toluene (116 mL) was cooled to −78° C. and treated with boron trifluoride diethyl etherate (3.49 mL, 28.3 mmol); this mixture was also allowed to stir at −78° C. for 30 minutes, and then added via cannula over three to four minutes to the aryllithium solution. The reaction mixture was stirred at −78° C. for approximately 30 minutes and was then quenched with saturated aqueous ammonium chloride solution. The mixture was extracted three times with ethyl acetate, and the combined organic layers were washed with saturated aqueous sodium chloride solution, dried over sodium sulfate, filtered, and concentrated in vacuo. Chromatography on silica gel (Gradient: 0% to 20% ethyl acetate in heptane) provided the product as a yellow oil. Yield: 4.39 g, 12.8 mmol, 90%. The stereochemical outcome of this reaction (cis ring fusion) was established via single crystal X-ray analysis of intermediate C17 (see data below). LCMS m/z 344.5 (M+1). $^1$H NMR (400 MHz, CDCl$_3$) δ 1.50-1.61 (m, 1H), 1.82-1.90 (m, 1H), 3.10-3.18 (m, 1H), 3.50 (dd, half of ABX pattern, J=10.3, 4.1 Hz, 1H), 3.55-3.60 (m, 2H), 3.72 (br d, J=7.2 Hz, 1H), 3.85-3.93 (m, 2H), 4.20 (dd, J=12.7, 1.8 Hz, 1H), 4.61 (AB quartet, $J_{AB}$=12.1 Hz, $\Delta v_{AB}$=22.5 Hz, 2H), 7.04 (ddd, J=12.1, 8.2, 1.2 Hz, 1H), 7.17 (ddd, J=7.8, 7.4, 1.4 Hz, 1H), 7.26-7.40 (m, 6H), 7.95 (ddd, J=8.1, 8.0, 1.8 Hz, 1H).

Step 2. Synthesis of {(2R,4R,5S)-5-amino-2-[(benzyloxy)methyl]-5-(2-fluorophenyl)tetrahydro-2H-pyran-4-yl}methanol (C14)

Compound C14 was prepared from (3aR,5R,7aS)-5-[(benzyloxy)methyl]-7a-(2-fluorophenyl)hexahydro-1H-pyrano[3,4-c][1,2]oxazole (C13) according to the general procedure for the synthesis of [(3S,4R)-3-amino-3-(2,4-difluorophenyl)tetrahydro-2H-pyran-4-yl]methanol (C11) in Example 1. The product was used directly in the following step. LCMS m/z 346.2 (M+1). $^1$H NMR (400 MHz, CDCl$_3$) δ 1.65 (ddd, J=14.0, 4.3, 2.5 Hz, 1H), 2.01-2.14 (m, 1H), 2.32-2.41 (m, 1H), 3.35 (dd, J=11.5, 2.9 Hz, 1H), 3.47-3.61 (m, 3H), 3.66 (dd, J=10.2, 6.6 Hz, 1H), 3.84-3.92 (m, 1H), 4.27 (dd, J=11.5, 2.0 Hz, 1H), 4.61 (AB quartet, $J_{AB}$=12.1 Hz, $\Delta v_{AB}$=25.1 Hz, 2H), 7.06 (ddd, J=13.0, 8.1, 1.3 Hz, 1H), 7.20-7.26 (m, 1H), 7.28-7.41 (m, 6H), 7.64-7.72 (m, 1H).

Step 3. Synthesis of (9H-fluoren-9-yl)methyl {(3S,4R,6R)-6-[(benzyloxy)methyl]-3-(2-fluorophenyl)-4-(hydroxymethyl)tetrahydro-2H-pyran-3-yl}carbamothioyl carbamate (C15)

{(2R,4R,5S)-5-Amino-2-[(benzyloxy)methyl]-5-(2-fluorophenyl)tetrahydro-2H-pyran-4-yl}methanol (C14) was converted to the product according to the general method for synthesis of 9H-fluoren-9-ylmethyl {[(3S,4R)-3-(2,4-difluorophenyl)-4-(hydroxymethyl)tetrahydro-2H-pyran-3-yl]carbamothioyl}carbamate (C12) in Example 1. Yield: 1.65 g, 2.63 mmol, 89% over two steps. LCMS m/z 627.4 (M+1).

Step 4. Synthesis of 9H-fluoren-9-ylmethyl [(4aR,6R,8aS)-6-[(benzyloxy)methyl]-8a-(2-fluorophenyl)-4,4-a,5,6,8,8a-hexahydropyrano[3,4-d][1,3]thiazin-2-yl]carbamate (C16)

(9H-Fluoren-9-yl)methyl {(3S,4R,6R)-6-[(benzyloxy)methyl]-3-(2-fluorophenyl)-4-(hydroxymethyl)tetrahydro-2H-pyran-3-yl}carbamothioyl carbamate (C15) (1.6 g, 2.6 mmol) was divided into three portions and each portion was dissolved in methanol (8 mL). Concentrated hydrochloric acid (12 M, 212 µL, 2.54 mmol) was added to each portion, and the three reaction mixtures were heated at 70° C. for 2 hours. The reactions were combined and concentrated in vacuo to provide the product as an off-white solid, which was used without additional purification. Yield: 1.4 g, 2.3 mmol, 88%. LCMS m/z 609.4 (M+1).

Step 5. Synthesis of [(4aR,6R,8aS)-2-amino-8a-(2-fluorophenyl)-4,4-a,5,6,8,8a-hexahydropyrano[3,4-d][1,3]thiazin-6-yl]methanol (C17)

9H-Fluoren-9-ylmethyl [(4aR,6R,8aS)-6-[(benzyloxy)methyl]-8a-(2-fluorophenyl)-4,4-a,5,6,8,8a-hexahydropyrano[3,4-d][1,3]thiazin-2-yl]carbamate (C16) (1.4 g, 2.3 mmol) was divided into two portions; each was mixed with concentrated hydrochloric acid (12 M, 6 mL) and heated to 120° C. for 3 hours. The reaction mixtures were combined and concentrated in vacuo. The resulting white solid was dissolved in acetonitrile (20 mL) and treated with piperidine (5 mL). The reaction mixture was stirred at room temperature for 42 hours, concentrated under reduced pressure, and chromatographed on silica gel (Gradient: 0% to 4% methanol in dichloromethane) to afford the product as a solid. Yield: 601 mg, 2.03 mmol, 88%. LCMS m/z 297.1 (M+1). $^1$H NMR (400 MHz, CD$_3$OD), characteristic peaks: δ 2.86 (dd, half of ABX pattern, J=12.7, 2.7 Hz, 1H), 2.98 (dd, half of ABX pattern, J=12.9, 4.1 Hz, 1H), 3.17-3.24 (m, 1H), 3.59 (d, J=5.1 Hz, 2H), 3.72-3.79 (m, 1H), 3.84 (d, J=11.9 Hz, 1H), 4.14 (dd, J=11.9, 1.4 Hz, 1H), 7.19 (ddd, J=13.1, 8.2, 1.2 Hz, 1H), 7.23-7.28 (m, 1H), 7.33 (ddd, J=8.0, 7.9, 1.9 Hz, 1H), 7.39-7.45 (m, 1H). The absolute and relative configuration of the title compound was confirmed via X-ray crystallography:

Single Crystal X-Ray Analysis

Data collection was performed on a Bruker APEX diffractometer at room temperature. Data collection consisted of 3 omega scans at low angle and 3 at high angle, each with 0.5 step. In addition, 2 phi scans were collected to improve the quality of the absorption correction.

The structure was solved by direct methods using SHELX software suite in the space group P2(1). The structure was subsequently refined by the full-matrix least squares method. All non-hydrogen atoms were found and refined using anisotropic displacement parameters.

A molecule of dichloromethane was revealed from the difference map during initial refinement and modeled as such.

The hydrogen atoms located on nitrogen were found from the Fourier difference map and refined freely, while the hydrogen atom bonded to oxygen was refined with distance restrained. The remaining hydrogen atoms were placed in calculated positions and were allowed to ride on their carrier atoms. The final refinement included isotropic displacement parameters for all hydrogen atoms.

The absolute configuration was confirmed by examination of the Flack parameter. In this case, the parameter=0.01 with an ESD of 0.03, within range for a successful absolute configuration determination.

The final R-index was 4.8%. A final difference Fourier revealed no missing or misplaced electron density.

Pertinent crystal, data collection and refinement are summarized in Table 1. Atomic coordinates, bond lengths, bond angles, torsion angles and displacement parameters are listed in Tables 2-5.

SOFTWARE AND REFERENCES

SHELXTL, Version 5.1, Bruker AXS, 1997
PLATON, A. L. Spek, *J. Appl. Cryst.* 2003, 36, 7-13.
MERCURY, C. F. Macrae, P. R. Edington, P. McCabe, E. Pidcock, G. P. Shields, R. Taylor, M. Towler and J. van de Streek, *J. Appl. Cryst.* 2006, 39, 453-457.
R. W. W. Hooft et al., *J. Appl. Cryst.* 2008, 41, 96-103.
H. D. Flack, *Acta Cryst.* 1983, A39, 867-881.

TABLE 1

| Crystal data and structure refinement for C17 | |
|---|---|
| Crystallization | dichloromethane |
| Empirical formula | $C_{15}H_{19}Cl_2FN_2O_2S$ |

TABLE 1-continued

Crystal data and structure refinement for C17

| | |
|---|---|
| Formula weight | 381.28 |
| Temperature | 296(2) K |
| Wavelength | 1.54178 Å |
| Crystal system | Monoclinic |
| Space group | P2(1) |
| Unit cell dimensions | a = 7.1784(2) Å   α = 90°. |
| | b = 10.2742(3) Å   β = 97.580(2)°. |
| | c = 11.7778(3) Å   γ = 90°. |
| Volume | 861.05(4) Å$^3$ |
| Z | 2 |
| Density (calculated) | 1.471 Mg/m$^3$ |
| Absorption coefficient | 4.707 mm$^{-1}$ |
| F(000) | 396 |
| Crystal size | 0.75 × 0.19 × 0.12 mm$^3$ |
| Theta range for data collection | 3.79 to 69.15° |
| Index ranges | −7 ≤ h ≤ 8, −12 ≤ k ≤ 12, −13 ≤ l ≤ 10 |
| Reflections collected | 4268 |
| Independent reflections | 2641 [R$_{int}$ = 0.0171] |
| Completeness to theta = 69.15° | 93.4% |
| Absorption correction | Empirical |
| Refinement method | Full-matrix least-squares on F$^2$ |
| Data/restraints/parameters | 2641/2/220 |
| Goodness-of-fit on F$^2$ | 1.036 |
| Final R indices [I > 2sigma(I)] | R1 = 0.0477, wR2 = 0.1287 |
| R indices (all data) | R1 = 0.0512, wR2 = 0.1319 |
| Absolute structure parameter | 0.01(3) |
| Largest diff. peak and hole | 0.413 and −0.407 e.Å$^{-3}$ |

TABLE 2

Atomic coordinates (×10$^4$) and equivalent isotropic displacement parameters (Å$^2$ × 10$^3$) for C17. U(eq) is defined as one third of the trace of the orthogonalized U$_{ij}$ tensor.

| | x | y | z | U(eq) |
|---|---|---|---|---|
| C(1) | 3187(6) | 5872(4) | 507(4) | 55(1) |
| C(2) | 1988(7) | 5448(5) | −429(4) | 67(1) |
| C(3) | 1346(7) | 4182(5) | −455(4) | 68(1) |
| C(4) | 1920(7) | 3379(5) | 438(4) | 68(1) |
| C(5) | 3129(6) | 3820(4) | 1374(3) | 55(1) |
| C(6) | 3807(5) | 5098(4) | 1440(3) | 47(1) |
| C(7) | 5140(5) | 5566(3) | 2490(3) | 44(1) |
| C(8) | 4153(5) | 6700(4) | 3046(3) | 48(1) |
| C(9) | 7022(6) | 7799(4) | 3673(3) | 53(1) |
| C(10) | 8011(6) | 8486(5) | 4733(4) | 64(1) |
| C(11) | 8174(6) | 6740(4) | 3188(4) | 54(1) |
| C(12) | 7024(5) | 6084(4) | 2168(3) | 49(1) |
| C(13) | 8065(6) | 5038(4) | 1612(3) | 54(1) |
| C(14) | 6756(5) | 3705(4) | 3407(3) | 46(1) |
| C(15) | 3309(11) | 449(9) | 3247(6) | 113(2) |
| Cl(1) | 3960(4) | 316(2) | 1904(2) | 127(1) |
| Cl(2) | 956(3) | 416(3) | 3310(2) | 125(1) |
| F(1) | 3773(5) | 7128(3) | 482(2) | 81(1) |
| N(1) | 6937(7) | 2765(4) | 4204(4) | 61(1) |
| N(2) | 5416(4) | 4536(3) | 3364(2) | 44(1) |
| O(1) | 5313(4) | 7258(3) | 3987(2) | 52(1) |
| O(2) | 7116(5) | 9683(3) | 4950(3) | 69(1) |
| S(001) | 8574(2) | 3625(1) | 2529(1) | 61(1) |

TABLE 3

Bond lengths [Å] and angles [°] for C17.

| | |
|---|---|
| C(1)—F(1) | 1.358(5) |
| C(1)—C(2) | 1.377(6) |
| C(1)—C(6) | 1.382(5) |
| C(2)—C(3) | 1.378(8) |
| C(3)—C(4) | 1.357(7) |
| C(4)—C(5) | 1.386(6) |
| C(5)—C(6) | 1.400(6) |
| C(6)—C(7) | 1.537(5) |
| C(7)—N(2) | 1.472(5) |
| C(7)—C(12) | 1.547(5) |
| C(7)—C(8) | 1.552(5) |
| C(8)—O(1) | 1.417(5) |
| C(9)—O(1) | 1.438(5) |
| C(9)—C(11) | 1.523(6) |
| C(9)—C(10) | 1.525(6) |
| C(10)—O(2) | 1.426(6) |
| C(11)—C(12) | 1.522(6) |
| C(12)—C(13) | 1.506(5) |
| C(13)—S(001) | 1.817(4) |
| C(14)—N(2) | 1.282(5) |
| C(14)—N(1) | 1.342(6) |
| C(14)—S(001) | 1.770(4) |
| C(15)—Cl(2) | 1.701(8) |
| C(15)—Cl(1) | 1.713(8) |
| F(1)—C(1)—C(2) | 116.5(4) |
| F(1)—C(1)—C(6) | 119.7(4) |
| C(2)—C(1)—C(6) | 123.8(4) |
| C(1)—C(2)—C(3) | 119.2(4) |
| C(4)—C(3)—C(2) | 119.3(4) |
| C(3)—C(4)—C(5) | 120.8(5) |
| C(4)—C(5)—C(6) | 121.8(4) |
| C(1)—C(6)—C(5) | 115.0(4) |
| C(1)—C(6)—C(7) | 124.1(4) |
| C(5)—C(6)—C(7) | 120.9(3) |
| N(2)—C(7)—C(6) | 110.5(3) |
| N(2)—C(7)-(12) | 112.2(3) |
| C(6)—C(7)—C(12) | 112.5(3) |
| N(2)—C(7)—C(8) | 105.8(3) |
| C(6)—C(7)—C(8) | 107.7(3) |
| C(12)—C(7)—C(8) | 107.9(3) |
| O(1)—C(8)—C(7) | 112.3(3) |
| O(1)—C(9)—C(11) | 110.1(3) |
| O(1)—C(9)—C(10) | 106.8(3) |
| C(11)—C(9)—C(10) | 114.9(4) |
| O(2)—C(10)—C(9) | 112.0(4) |
| C(12)—C(11)—C(9) | 110.3(3) |
| C(13)—C(12)—C(11) | 114.2(3) |
| C(13)—C(12)—C(7) | 111.2(3) |
| C(11)—C(12)—C(7) | 111.1(3) |
| C(12)—C(13)—S(001) | 112.6(3) |
| N(2)—C(14)—N(1) | 120.6(4) |
| N(2)—C(14)—S(001) | 128.0(3) |
| N(1)—C(14)—S(001) | 111.4(3) |
| Cl(2)—C(15)—Cl(1) | 115.6(4) |
| C(14)—N(2)—C(7) | 122.5(3) |
| C(8)—O(1)—C(9) | 112.9(3) |
| C(14)—S(001)—C(13) | 101.75(18) |

Symmetry transformations used to generate equivalent atoms.

TABLE 4

Anisotropic displacement parameters (Å$^2$ × 10$^3$) for C17. The anisotropic displacement factor exponent takes the form: $-2\pi^2 [h^2 a^{*2} U^{11} + \ldots + 2 h k a^* b^* U^{12}]$

| | U$^{11}$ | U$^{22}$ | U$^{33}$ | U$^{23}$ | U$^{13}$ | U$^{12}$ |
|---|---|---|---|---|---|---|
| C(1) | 64(3) | 58(2) | 44(2) | 5(2) | 9(2) | 8(2) |
| C(2) | 75(3) | 85(3) | 40(2) | 6(2) | 4(2) | 19(3) |
| C(3) | 61(3) | 93(4) | 47(2) | −20(2) | −2(2) | 10(2) |
| C(4) | 69(3) | 67(3) | 67(3) | −11(2) | 0(2) | 6(2) |
| C(5) | 62(2) | 54(2) | 48(2) | −2(2) | 6(2) | 10(2) |
| C(6) | 48(2) | 55(2) | 38(2) | −1(2) | 9(1) | 6(2) |
| C(7) | 48(2) | 48(2) | 37(2) | 6(2) | 11(1) | 3(2) |
| C(8) | 45(2) | 55(2) | 43(2) | 4(2) | 6(2) | 6(2) |
| C(9) | 53(2) | 53(2) | 53(2) | 1(2) | 13(2) | 1(2) |
| C(10) | 61(3) | 68(3) | 63(3) | −5(2) | 5(2) | −5(2) |
| C(11) | 49(2) | 60(2) | 55(2) | 2(2) | 15(2) | 0(2) |
| C(12) | 49(2) | 57(2) | 42(2) | 7(2) | 12(2) | 5(2) |

TABLE 4-continued

Anisotropic displacement parameters (Å$^2$ × 10$^3$) for C17. The anisotropic displacement factor exponent takes the form: $-2\pi^2$ [h$^2$ a*$^2$U$^{11}$ + ... + 2 h k a* b* U$^{12}$]

|  | U$^{11}$ | U$^{22}$ | U$^{33}$ | U$^{23}$ | U$^{13}$ | U$^{12}$ |
|---|---|---|---|---|---|---|
| C(13) | 55(2) | 66(2) | 43(2) | 6(2) | 17(2) | 11(2) |
| C(14) | 51(2) | 51(2) | 35(2) | 1(2) | 7(1) | 1(2) |
| C(15) | 112(5) | 122(5) | 102(5) | −21(4) | 1(4) | 23(5) |
| Cl(1) | 166(2) | 99(1) | 125(2) | 27(1) | 60(1) | 34(1) |
| Cl(2) | 105(1) | 153(2) | 118(1) | −28(1) | 12(1) | −20(1) |
| F(1) | 105(2) | 68(2) | 64(2) | 24(1) | −6(1) | −9(1) |
| N(1) | 68(3) | 57(2) | 60(2) | 13(2) | 18(2) | 18(2) |
| N(2) | 49(2) | 51(2) | 35(2) | 3(1) | 11(1) | 2(1) |
| O(1) | 50(2) | 58(2) | 49(2) | −10(1) | 13(1) | 0(1) |
| O(2) | 86(2) | 59(2) | 64(2) | −8(2) | 24(2) | −4(2) |
| S(001) | 65(1) | 66(1) | 55(1) | 8(1) | 23(1) | 19(1) |

TABLE 5

Hydrogen coordinates (×10$^4$) and isotropic displacement parameters (Å$^2$ × 10$^3$) for C17.

|  | x | y | z | U(eq) |
|---|---|---|---|---|
| H(2A) | 1616 | 6008 | −1036 | 80 |
| H(3) | 529 | 3882 | −1078 | 81 |
| H(4) | 1496 | 2523 | 421 | 82 |
| H(5) | 3499 | 3250 | 1975 | 66 |
| H(8A) | 3805 | 7367 | 2474 | 57 |
| H(8B) | 3010 | 6378 | 3303 | 57 |
| H(9) | 6688 | 8453 | 3075 | 63 |
| H(10A) | 8017 | 7919 | 5392 | 77 |
| H(10B) | 9306 | 8656 | 4628 | 77 |
| H(11A) | 9298 | 7119 | 2950 | 65 |
| H(11B) | 8557 | 6097 | 3776 | 65 |
| H(12) | 6710 | 6762 | 1589 | 59 |
| H(13A) | 9236 | 5394 | 1420 | 65 |
| H(13B) | 7317 | 4769 | 905 | 65 |
| H(15A) | 3890 | −256 | 3714 | 136 |
| H(15B) | 3810 | 1258 | 3584 | 136 |
| H(99A) | 6130(70) | 2670(50) | 4680(40) | 57(13) |
| H(99B) | 7560(60) | 2240(40) | 4200(30) | 38(12) |
| H(98A) | 7420(160) | 9760(120) | 5790(20) | 220(50) |

Step 6. Synthesis of tert-butyl [(4aR,6R,8aS)-8a-(2-fluorophenyl)-6-(hydroxymethyl)-4,4-a,5,6,8,8a-hexahydropyrano[3,4-d][1,3]thiazin-2-yl]carbamate (C18)

Triethylamine (0.455 mL, 3.26 mmol) was added to a solution of [(4aR,6R,8aS)-2-amino-8a-(2-fluorophenyl)-4,4-a,5,6,8,8a-hexahydropyrano[3,4-d][1,3]thiazin-6-yl]methanol (C17) (601 mg, 2.03 mmol) in a mixture of tetrahydrofuran (10 mL) and methanol (5 mL). Di-tert-butyl dicarbonate (575 mg, 2.63 mmol) was then added, and the reaction mixture was allowed to stir at room temperature for 18 hours. At this point, starting material was observed by thin layer chromatography, so 4-(dimethylamino)pyridine (25 mg, 0.20 mmol) was added, and the reaction mixture was heated to 50° C. for 24 hours. Solvents were removed in vacuo, and the residue was purified via silica gel chromatography (Gradient: 0% to 4% methanol in dichloromethane) to provide the product as a white solid. Yield: 350 mg, 0.883 mmol, 43%. LCMS m/z 397.2 (M+1). $^1$H NMR (400 MHz, CD$_3$OD) δ 1.51 (s, 9H), 1.62-1.69 (m, 1H), 1.73-1.85 (m, 1H), 2.68-2.74 (m, 1H), 2.87-2.94 (m, 1H), 3.12-3.21 (m, 1H), 3.59 (d, J=5.1 Hz, 2H), 3.71-3.78 (m, 1H), 3.81 (d, J=11.9 Hz, 1H), 4.15 (dd, J=12.0, 1.3 Hz, 1H), 7.14-7.21 (m, 1H), 7.22-7.28 (m, 1H), 7.33 (ddd, J=8.1, 8.0, 1.9 Hz, 1H), 7.37-7.44 (m, 1H).

Step 7. Synthesis of [(4aR,6R,8aS)-2-[(tert-butoxycarbonyl)amino]-8a-(2-fluorophenyl)-4,4-a,5,6,8,8a-hexahydropyrano[3,4-d][1,3]thiazin-6-yl]methyl methanesulfonate (C19)

Methanesulfonyl chloride (36.2 µL, 0.474 mmol) was added drop-wise to a 0° C. solution of tert-butyl [(4aR,6R,8aS)-8a-(2-fluorophenyl)-6-(hydroxymethyl)-4,4-a,5,6,8,8a-hexahydropyrano[3,4-d][1,3]thiazin-2-yl]carbamate (C18) (94 mg, 0.24 mmol) and triethylamine (0.198 mL, 1.42 mmol) in dichloromethane (1 mL). The reaction was allowed to warm to room temperature and stir for 18 hours. Saturated aqueous sodium bicarbonate solution was added, and the mixture was extracted three times with dichloromethane. The combined organic layers were washed with water, washed with saturated aqueous sodium chloride solution, dried over sodium sulfate, filtered, and concentrated under reduced pressure. Silica gel chromatography (Gradient: 0% to 50% ethyl acetate in heptane) provided the product as a white solid. Yield: 86 mg, 0.18 mmol, 75%. LCMS m/z 475.4 (M+1). $^1$H NMR (400 MHz, CDCl$_3$) δ 1.53 (s, 9H), 1.60-1.68 (br m, 1H), 1.92-2.07 (br m, 1H), 2.56 (dd, J=12.9, 2.9 Hz, 1H), 2.93 (dd, J=12.7, 3.9 Hz, 1H), 3.07-3.19 (br m, 1H), 3.09 (s, 3H), 3.79 (d, J=12.1 Hz, 1H), 3.96-4.04 (m, 1H), 4.21 (dd, J=12.0, 1.5 Hz, 1H), 4.27 (dd, half of ABX pattern, J=11.3, 6.2 Hz, 1H), 4.32-4.38 (br m, 1H), 7.06-7.13 (m, 1H), 7.18-7.24 (m, 1H), 7.30-7.39 (br m, 2H).

Step 8. Synthesis of tert-butyl {(4aR,6R,8aS)-8a-(2-fluorophenyl)-6-[(propan-2-yloxy)methyl]-4,4-a,5,6,8,8a-hexahydropyrano[3,4-d][1,3]thiazin-2-yl}carbamate (C20)

The sodium salt of 2-propanol (34 mg, 0.41 mmol) was dissolved in 2-propanol (1.5 mL), and this was added to a solution of [(4aR,6R,8aS)-2-[(tert-butoxycarbonyl)amino]-8a-(2-fluorophenyl)-4,4-a,5,6,8,8a-hexahydropyrano[3,4-d][1,3]thiazin-6-yl]methyl methanesulfonate (C19) (40 mg, 0.084 mmol) in 2-propanol (0.5 mL). After 18 hours, additional sodium salt (34 mg, 0.41 mmol) was added, and stirring was continued for 66 hours. After addition of aqueous ammonium chloride solution, the mixture was extracted three times with ethyl acetate. The combined organic layers were washed with water, washed with saturated aqueous sodium chloride solution, dried over sodium sulfate, filtered, and concentrated in vacuo. Purification was carried out via preparative thin layer chromatography on silica gel (Eluent: 1:1 ethyl acetate/heptane) to provide the product as a white foam. Yield: 11.2 mg, 0.255 mmol, 30%. LCMS m/z 439.4 (M+1). $^1$H NMR (400 MHz, CDCl$_3$) δ 1.19 (br d, J=6.2 Hz, 6H), 1.54 (s, 9H), 1.63-1.71 (br m, 1H), 1.83-1.97 (br m, 1H), 2.50-2.59 (m, 1H), 2.93 (dd, J=13, 4 Hz, 1H), 3.07-3.18 (br m, 1H), 3.41 (dd, J=9.9, 4.8 Hz, 1H), 3.58-3.68 (m, 2H), 3.72-3.89 (m, 2H), 4.20 (br d, J=12 Hz, 1H), 7.05-7.12 (m, 1H), 7.17-7.23 (m, 1H), 7.30-7.40 (m, 2H).

Step 9. Synthesis of (4aR,6R,8aS)-8a-(2-fluorophenyl)-6-[(propan-2-yloxy)methyl]-4,4-a,5,6,8,8a-hexahydropyrano[3,4-d][1,3]thiazin-2-amine, trifluoroacetate salt (2)

Trifluoroacetic acid (0.5 mL) was added to a 0° C. solution of tert-butyl {(4aR,6R,8aS)-8a-(2-fluorophenyl)-6-[(propan-2-yloxy)methyl]-4,4-a,5,6,8,8a-hexahydropyrano[3,4-d][1,3]thiazin-2-yl}carbamate (C20) (11.2 mg, 0.0255 mmol) in dichloromethane (1.5 mL), and the reaction mixture was allowed to warm to room temperature and stir for 18 hours. After removal of solvents in vacuo, the residue was purified via reversed-phase HPLC (Column: Waters Sunfire C18, 5 μm; Mobile phase A: 0.05% trifluoroacetic acid in water (v/v); Mobile phase B: 0.05% trifluoroacetic acid in acetonitrile (v/v); Gradient: 20% to 100% B) to afford the product as an oil. Yield: 11.8 mg, 0.026 mmol, quantitative. LCMS m/z 339.3 (M+1). $^1$H NMR (600 MHz, DMSO-$d_6$) δ 1.09 (d, J=5.7 Hz, 3H), 1.09 (d, J=6.1 Hz, 3H), 1.52-1.60 (m, 1H), 1.70-1.75 (m, 1H), 2.84 (dd, J=12.7, 4.0 Hz, 1H), 3.04 (dd, J=13.2, 2.6 Hz, 1H), 3.17-3.23 (m, 1H), 3.42 (dd, half of ABX pattern, J=10.3, 4.2 Hz, 1H), 3.46 (dd, half of ABX pattern, J=10.5, 5.7 Hz, 1H), 3.58 (septet, J=6.1 Hz, 1H), 3.76-3.81 (m, 1H), 3.91 (AB quartet, $J_{AB}$=12 Hz, $\Delta v_{AB}$=32 Hz, 2H), 7.23-7.28 (m, 1H), 7.29-7.36 (m, 2H), 7.46-7.51 (m, 1H)

Example 3

[(4aR,6R,8aS)-2-Amino-8a-(2,4-difluorophenyl)-4,4-a,5,6,8,8a-hexahydropyrano[3,4-d][1,3]thiazin-6-yl]methanol (3)

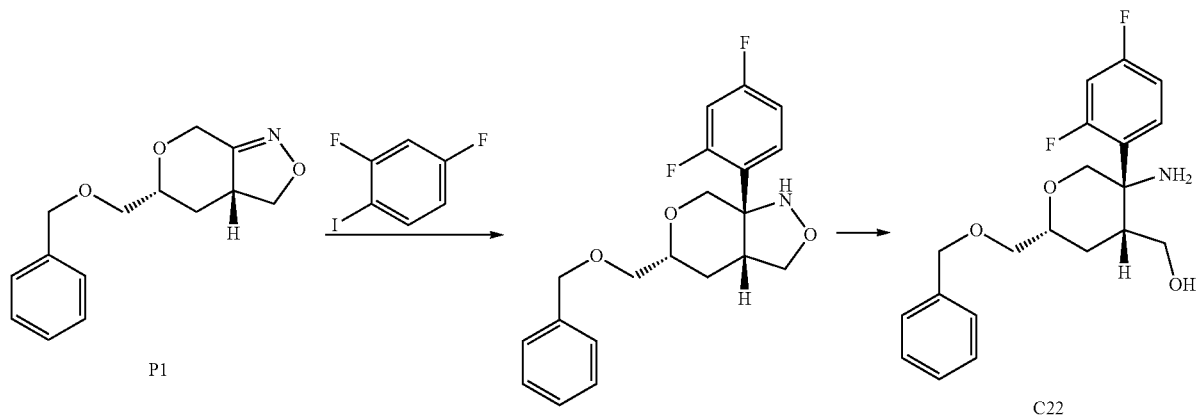

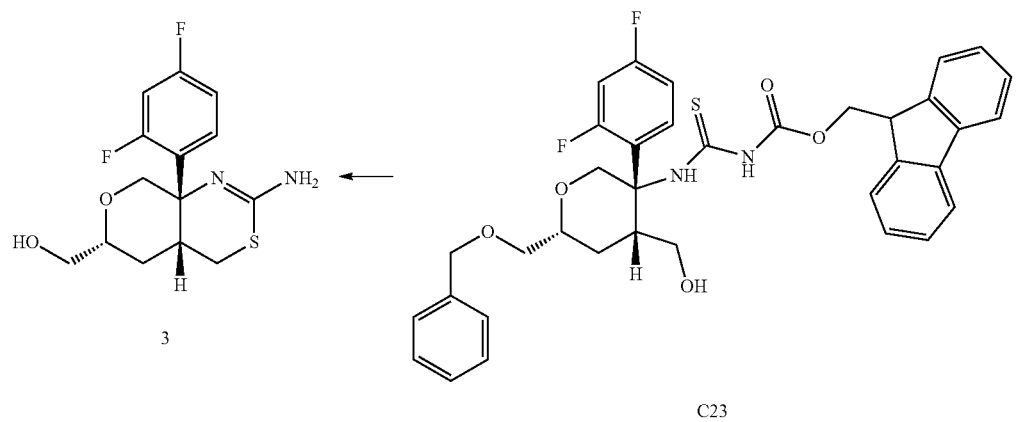

Step 1. Synthesis of (3aR,5R,7aS)-5-[(benzyloxy)methyl]-7a-(2,4-difluorophenyl)hexahydro-1H-pyrano[3,4-c][1,2]oxazole (C21)

Boron trifluoride diethyl etherate (0.603 mL, 4.88 mmol) was added to a solution of (3aR,5R)-5-[(benzyloxy)methyl]-3,3a,4,5-tetrahydro-7H-pyrano[3,4-c][1,2]oxazole (P1) (500 mg, 2.02 mmol) in a 3:1 mixture of toluene and dipropan-2-yl ether (20 mL) at −78° C. The reaction was stirred at this temperature for 30 minutes, then treated with 2,4-difluoro-1-iodobenzene (0.271 mL, 2.27 mmol). While maintaining the reaction temperature at −78 to −73° C., n-butyllithium (2.5 M in hexanes, 0.855 mL, 2.14 mmol) was slowly added. The reaction was stirred at −78° C. for 1 hour, then quenched with saturated aqueous ammonium chloride solution and water. After three extractions with ethyl acetate, the combined organic layers were dried over sodium sulfate, filtered and concentrated in vacuo. Chromatography on silica gel (Gradient: 0% to 20% ethyl acetate in heptane) afforded the product as a colorless oil. Increasing the gradient to 30% ethyl acetate in heptane provided recovered starting material (241 mg, 0.974 mmol). Yield: 399 mg, 1.10 mmol, 54% (quantitative yield based on recovered starting material). LCMS m/z 362.2 (M+1). $^1$H NMR (400 MHz, CDCl$_3$) δ 1.48-1.60 (m, 1H, assumed; partially obscured by water peak), 1.82-1.90 (m, 1H), 3.04-3.12 (m, 1H), 3.50 (dd, half of ABX pattern, J=10.2, 4.1 Hz, 1H), 3.53-3.59 (m, 2H), 3.72 (br d, J=7 Hz, 1H), 3.82-3.90 (m, 2H), 4.14 (dd, J=12.7, 1.8 Hz, 1H), 4.60 (AB quartet, J$_{AB}$=12.1 Hz, Δv$_{AB}$=21.4 Hz, 2H), 6.80 (ddd, J=11.9, 8.6, 2.5 Hz, 1H), 6.87-6.93 (m, 1H), 7.28-7.40 (m, 5H), 7.93 (ddd, J=9.1, 9.0, 6.8 Hz, 1H).

Step 2. Synthesis of [(2R,4R,5S)-5-amino-2-[(benzyloxy)methyl]-5-(2,4-difluorophenyl)tetrahydro-2H-pyran-4-yl]methanol (C22)

(3aR,5R,7aS)-5-[(Benzyloxy)methyl]-7a-(2,4-difluorophenyl)hexahydro-1H-pyrano[3,4-c][1,2]oxazole (C21) (742 mg, 2.05 mmol) was mixed with acetic acid (6.8 mL). After addition of zinc powder (1.75 g, 26.7 mmol), the reaction mixture was stirred for 18 hours. Insoluble material was removed via filtration, and the solids were washed with ethyl acetate. The combined filtrates were washed with saturated aqueous sodium bicarbonate solution, and the aqueous layer was extracted with ethyl acetate. The combined organic layers were washed with saturated aqueous sodium chloride solution, dried over sodium sulfate, filtered, and concentrated under reduced pressure to provide the product as an opaque oil, which was used in the following reaction without additional purification. Yield: 748 mg, quantitative. LCMS m/z 364.4 (M+1). $^1$H NMR (400 MHz, CDCl$_3$) δ 1.65 (ddd, J=14.0, 4.3, 2.6 Hz, 1H), 1.98-2.16 (br m, 1H), 2.24-2.41 (br m, 1H), 3.32-3.41 (m, 1H), 3.42-3.60 (m, 3H), 3.60-3.73 (br m, 1H), 3.82-3.92 (br m, 1H), 4.22 (dd, J=11.5, 2.3 Hz, 1H), 4.61 (AB quartet, upfield signals are broadened, J$_{AB}$=12.1 Hz, Δv$_{AB}$=29 Hz, 2H), 6.83 (ddd, J=12.6, 8.6, 2.6 Hz, 1H), 6.92-7.05 (br m, 1H), 7.27-7.40 (m, 5H), 7.62-7.79 (br m, 1H).

Step 3. Synthesis of 9H-fluoren-9-ylmethyl {[(3S,4R,6R)-6-[(benzyloxy)methyl]-3-(2,4-difluorophenyl)-4-(hydroxymethyl)tetrahydro-2H-pyran-3-yl]carbamothioyl}carbamate (C23)

Conversion of [(2R,4R,5S)-5-amino-2-[(benzyloxy)methyl]-5-(2,4-difluorophenyl)tetrahydro-2H-pyran-4-yl]methanol (C22) to the product was carried out according to the general procedure for the synthesis of 9H-fluoren-9-ylmethyl {[(3S,4R)-3-(2,4-difluorophenyl)-4-(hydroxymethyl)tetrahydro-2H-pyran-3-yl]carbamothioyl}carbamate (C12) in Example 1. The product was obtained as a white solid. Yield: 995 mg, 1.54 mmol, 75%. LCMS m/z 645.6 (M+1). $^1$H NMR (400 MHz, CDCl$_3$), characteristic peaks: δ 3.52 (dd, J=10.3, 4.1 Hz, 1H), 3.64 (dd, J=10.2, 6.0 Hz, 1H), 4.46 (dd, half of ABX pattern, J=10.6, 6.9 Hz, 1H), 4.60 (AB quartet, J$_{AB}$=12.0 Hz, Δv$_{AB}$=11.1 Hz, 2H), 6.73-6.81 (m, 1H), 6.86-6.92 (m, 1H), 7.20-7.25 (m, 1H), 7.42-7.48 (m, 2H), 7.54-7.59 (m, 2H).

Step 4. Synthesis of [(4aR,6R,8aS)-2-amino-8a-(2,4-difluorophenyl)-4,4-a,5,6,8,8a-hexahydropyrano[3,4-d][1,3]thiazin-6-yl]methanol (3)

Concentrated hydrochloric acid (12 M, 17.6 mL) was added to a methanol solution of 9H-fluoren-9-ylmethyl {[(3S,4R,6R)-6-[(benzyloxy)methyl]-3-(2,4-difluorophenyl)-4-(hydroxymethyl)tetrahydro-2H-pyran-3-yl]carbamothioyl}carbamate (C23) (995 mg, 1.54 mmol), and the reaction mixture was heated to 70° C. for 2 hours. At this point, LCMS analysis indicated that the starting material had been consumed. The methanol was allowed to distill off, and the aqueous residue was heated to 120° C. for 3 hours. The reaction mixture was partitioned between water and ethyl acetate, and the aqueous layer was extracted with ethyl acetate. These organic layers were shown by chromatographic separation, followed by $^1$H NMR and LCMS analysis, to contain cyclized material still retaining the fluorenylmethoxycarbonyl protecting group. The aqueous layer was basified with saturated aqueous sodium bicarbonate solution and extracted three times with ethyl acetate. These extracts were combined, washed with saturated aqueous sodium chloride solution, dried over sodium sulfate, filtered, and concentrated under reduced pressure. The residue was triturated with dichloromethane to afford the product as a white solid. The filtrate from the trituration was concentrated in vacuo and triturated with dichloromethane to afford additional product, also as a white solid. Yield: 235 mg, 0.748 mmol, 49%. LCMS m/z 315.3 (M+1). $^1$H NMR (400 MHz, CDCl$_3$) δ 1.41-1.47 (m, 1H), 1.84-1.96 (m, 1H), 2.61-2.68 (m, 1H), 2.92-3.01 (m, 2H), 3.65 (dd, half of ABX pattern, J=11.7, 6.7 Hz, 1H), 3.70 (dd, half of ABX pattern, J=11.7, 3.2 Hz, 1H), 3.73-3.81 (m, 1H), 3.85 (d, J=11.3 Hz, 1H), 4.11 (dd, J=11.2, 2.2 Hz, 1H), 6.82 (ddd, J=12.4, 8.5, 2.6 Hz, 1H), 6.86-6.92 (m, 1H), 7.34 (ddd, J=9.1, 9.0, 6.7 Hz, 1H).

Single Crystal X-Ray Analysis

Data collection was performed on a Bruker APEX diffractometer at room temperature. Data collection consisted of 3 omega scans at low angle and three at high angle, each with 0.5 step. In addition, 2 phi scans were collected to improve the quality of the absorption correction.

The structure was solved by direct methods using SHELX software suite in the space group P2(1). The structure was subsequently refined by the full-matrix least squares method. All non-hydrogen atoms were found and refined using anisotropic displacement parameters.

The hydrogen atoms located on nitrogen and oxygen were found from the Fourier difference map and refined freely in the case of H99a and H99b; restrained in the case of H98a. The remaining hydrogen atoms were placed in calculated positions and were allowed to ride on their carrier atoms. The final refinement included isotropic displacement parameters for all hydrogen atoms.

The absolute configuration was established by examination of the Flack parameter. In this case, the parameter=0.0867 with an ESD of 0.0507, within range for absolute configuration determination with the assumption of an enantiopure sample.

The final R-index was 7.2%. A final difference Fourier revealed no missing or misplaced electron density. This is a higher than expected R value for a compound with this formula, possible because of solvate.

Pertinent crystal, data collection and refinement are summarized in Table 6. Atomic coordinates, bond lengths, bond angles, torsion angles and displacement parameters are listed in tables 7-10.

TABLE 6

Crystal data and structure refinement for Example 3.

| | |
|---|---|
| Crystallization | methanol |
| Empirical formula | $C_{15}H_{18}Cl_2F_2N_2O_2S$ |
| Formula weight | 399.27 |
| Temperature | 273(2) K |
| Wavelength | 1.54178 Å |
| Crystal system | Monoclinic |
| Space group | P2(1) |
| Unit cell dimensions | a = 7.2335(9) Å    α = 90°. |
| | b = 10.3268(13) Å  β = 97.267(6)°. |
| | c = 11.7941(13) Å  γ = 90°. |
| Volume | 873.93(18) Å³ |
| Z | 2 |
| Density (calculated) | 1.517 Mg/m³ |
| Absorption coefficient | 4.751 mm⁻¹ |
| F(000) | 412 |
| Theta range for data collection | 3.78 to 54.23°. |
| Index ranges | $-7 <= h <= 5, -10 <= k <= 9, -12 <= l <= 12$ |
| Reflections collected | 2206 |
| Independent reflections | 1552 [R(int) = 0.0512] |
| Completeness to theta = 54.23° | 86.0% |
| Absorption correction | Empirical |
| Refinement method | Full-matrix least-squares on $F^2$ |
| Data/restraints/parameters | 1552/2/229 |
| Goodness-of-fit on $F^2$ | 1.160 |
| Final R indices [I > 2sigma(I)] | R1 = 0.0720, wR2 = 0.2020 |
| R indices (all data) | R1 = 0.0789, wR2 = 0.2247 |
| Absolute structure parameter | 0.09(5) |
| Largest diff. peak and hole | 0.429 and −0.316 e.Å⁻³ |

TABLE 7

Atomic coordinates (×10⁴) and equivalent isotropic displacement parameters (Å² × 10³) for Example 3. U(eq) is defined as one third of the trace of the orthogonalized $U^{ij}$ tensor.

| | x | y | z | U(eq) |
|---|---|---|---|---|
| C(1) | 1730(12) | 1090(10) | 3436(6) | 52(2) |
| C(2) | 150(12) | 2884(10) | 2535(6) | 51(2) |
| C(3) | 2050(13) | 3407(10) | 2182(6) | 58(2) |
| C(4) | 3044(15) | 2308(12) | 1636(7) | 65(3) |
| C(5) | −1172(12) | 2367(11) | 1487(6) | 56(2) |
| C(6) | −1770(15) | 3111(14) | 539(7) | 71(3) |
| C(7) | −2955(14) | 2636(13) | −399(7) | 69(3) |
| C(8) | −3568(17) | 1391(13) | −337(7) | 74(3) |
| C(9) | −3063(14) | 613(12) | 584(8) | 70(3) |
| C(10) | −1870(13) | 1111(11) | 1492(6) | 60(2) |
| C(11) | −814(12) | 4021(11) | 3035(6) | 55(2) |
| C(12) | 2056(12) | 5157(11) | 3633(7) | 55(2) |
| C(13) | 3187(14) | 4078(11) | 3209(7) | 63(2) |
| C(14) | 3004(15) | 5856(13) | 4652(8) | 69(3) |
| C(99) | 1810(20) | 2630(20) | 6736(11) | 115(5) |
| Cl(1) | 3982(6) | 3080(6) | 6724(3) | 128(2) |
| Cl(3) | 984(7) | 2637(5) | 8073(4) | 129(2) |
| F(1) | −1135(10) | 4338(8) | 446(4) | 89(2) |

TABLE 7-continued

Atomic coordinates (×10⁴) and equivalent isotropic displacement parameters (Å² × 10³) for Example 3. U(eq) is defined as one third of the trace of the orthogonalized $U^{ij}$ tensor.

| | x | y | z | U(eq) |
|---|---|---|---|---|
| F(2) | −4728(10) | 929(10) | −1219(5) | 100(2) |
| N(1) | 1914(16) | 92(11) | 4253(6) | 71(3) |
| N(2) | 448(10) | 1871(8) | 3431(5) | 51(2) |
| O(1) | 338(8) | 4637(6) | 3959(4) | 54(2) |
| O(2) | 2107(10) | 7044(9) | 4869(5) | 75(2) |
| S(001) | 3498(4) | 922(3) | 2547(2) | 71(1) |

TABLE 8

Bond lengths [Å] and angles [°] for Example 3.

| | |
|---|---|
| C(1)—N(2) | 1.228(12) |
| C(1)—N(1) | 1.406(13) |
| C(1)—S(001) | 1.763(7) |
| C(2)—N(2) | 1.482(12) |
| C(2)—C(11) | 1.522(14) |
| C(2)—C(5) | 1.558(12) |
| C(2)—C(3) | 1.581(12) |
| C(3)—C(4) | 1.529(14) |
| C(3)—C(13) | 1.541(13) |
| C(4)—S(001) | 1.795(10) |
| C(5)—C(6) | 1.380(14) |
| C(5)—C(10) | 1.392(16) |
| C(6)—F(1) | 1.357(16) |
| C(6)—C(7) | 1.400(15) |
| C(7)—C(8) | 1.365(18) |
| C(8)—F(2) | 1.339(13) |
| C(8)—C(9) | 1.363(16) |
| C(9)—C(10) | 1.387(14) |
| C(11)—O(1) | 1.434(11) |
| C(12)—O(1) | 1.450(11) |
| C(12)—C(14) | 1.493(15) |
| C(12)—C(13) | 1.504(15) |
| C(14)—O(2) | 1.427(15) |
| C(99)—Cl(1) | 1.643(16) |
| C(99)—Cl(3) | 1.753(14) |
| N(2)—C(1)—N(1) | 119.4(8) |
| N(2)—C(1)—S(001) | 131.7(7) |
| N(1)—C(1)—S(001) | 108.8(7) |
| N(2)—C(2)—C(11) | 107.5(6) |
| N(2)—C(2)—C(5) | 110.1(8) |
| C(11)—C(2)—C(5) | 107.8(7) |
| N(2)—C(2)—C(3) | 112.1(7) |
| C(11)—C(2)—C(3) | 107.1(8) |
| C(5)—C(2)—C(3) | 112.0(6) |
| C(4)—C(3)—C(13) | 115.7(8) |
| C(4)—C(3)—C(2) | 109.1(9) |
| C(13)—C(3)—C(2) | 110.0(6) |
| C(3)—C(4)—S(001) | 113.6(6) |
| C(6)—C(5)—C(10) | 116.5(9) |
| C(6)—C(5)—C(2) | 123.4(10) |
| C(10)—C(5)—C(2) | 120.1(7) |
| F(1)—C(6)—C(5) | 120.7(9) |
| F(1)—C(6)—C(7) | 116.3(9) |
| C(5)—C(6)—C(7) | 122.9(12) |
| C(8)—C(7)—C(6) | 117.3(10) |
| F(2)—C(8)—C(9) | 119.2(13) |
| F(2)—C(8)—C(7) | 118.0(10) |
| C(9)—C(8)—C(7) | 122.8(10) |
| C(8)—C(9)—C(10) | 118.3(11) |
| C(9)—C(10)—C(5) | 122.2(9) |
| O(1)—C(11)—C(2) | 112.7(7) |
| O(1)—C(12)—C(14) | 106.7(7) |
| O(1)—C(12)—C(13) | 109.5(9) |
| C(14)—C(12)—C(13) | 114.3(8) |
| C(12)—C(13)—C(3) | 109.6(8) |
| O(2)—C(14)—C(12) | 112.8(8) |
| Cl(1)—C(99)—Cl(3) | 116.1(8) |
| C(1)—N(2)—C(2) | 120.5(7) |

TABLE 8-continued

Bond lengths [Å] and angles [°] for Example 3.

| | |
|---|---|
| C(11)—O(1)—C(12) | 113.4(6) |
| C(1)—S(001)—C(4) | 100.7(4) |

Symmetry transformations used to generate equivalent atoms:

TABLE 9

Anisotropic displacement parameters (Å$^2$ × 10$^3$) for Example 3. The anisotropic displacement factor exponent takes the form: $-2\pi^2$ [h$^2$ a*$^2$U$^{11}$ + ... + 2 h k a* b* U$^{12}$]

| | U$^{11}$ | U$^{22}$ | U$^{33}$ | U$^{23}$ | U$^{13}$ | U$^{12}$ |
|---|---|---|---|---|---|---|
| C(1) | 53(5) | 65(7) | 40(4) | −1(4) | 16(3) | 12(4) |
| C(2) | 48(5) | 66(6) | 42(3) | 12(4) | 10(3) | −1(4) |
| C(3) | 59(6) | 70(7) | 46(4) | 4(4) | 14(3) | 11(4) |
| C(4) | 71(6) | 79(8) | 47(4) | 11(4) | 16(4) | 14(5) |
| C(5) | 54(5) | 76(7) | 39(4) | 13(4) | 11(3) | 11(4) |
| C(6) | 75(7) | 96(10) | 44(4) | 6(5) | 10(4) | −3(5) |
| C(7) | 69(7) | 92(10) | 47(4) | −5(5) | 13(4) | 8(6) |
| C(8) | 80(8) | 99(10) | 41(5) | −17(5) | 2(4) | 14(6) |
| C(9) | 66(7) | 74(9) | 69(6) | −11(5) | 5(4) | 6(5) |
| C(10) | 62(6) | 71(7) | 49(4) | 5(4) | 11(4) | 2(5) |
| C(11) | 37(5) | 70(6) | 57(4) | 4(4) | 6(3) | 5(3) |
| C(12) | 42(5) | 70(7) | 53(4) | 8(4) | 5(3) | −3(4) |
| C(13) | 56(6) | 73(7) | 60(4) | 14(4) | 12(4) | 1(4) |
| C(14) | 64(7) | 76(7) | 67(5) | 13(6) | 13(4) | 23(5) |
| C(99) | 123(13) | 127(15) | 94(8) | −23(9) | 3(8) | −27(10) |
| Cl(1) | 105(3) | 162(5) | 112(2) | 46(3) | −3(2) | −36(3) |
| Cl(3) | 147(4) | 115(3) | 134(3) | −42(3) | 52(2) | −39(3) |
| F(1) | 101(5) | 98(6) | 64(3) | 28(3) | −4(3) | −15(4) |
| F(2) | 102(5) | 123(6) | 70(3) | −34(4) | −14(3) | 22(5) |
| N(1) | 64(6) | 92(8) | 59(5) | 17(4) | 19(4) | 27(6) |
| N(2) | 48(4) | 63(5) | 44(3) | 2(3) | 17(3) | 3(4) |
| O(1) | 56(4) | 58(4) | 49(3) | −8(2) | 11(2) | 3(2) |
| O(2) | 74(5) | 90(6) | 62(3) | −5(3) | 19(3) | −9(4) |
| S(001) | 79(2) | 78(2) | 63(1) | 13(1) | 30(1) | 34(1) |

TABLE 10

Hydrogen coordinates (×10$^4$) and isotropic displacement parameters (Å$^2$ × 10$^3$) for Example 3.

| | x | y | z | U(eq) |
|---|---|---|---|---|
| H(021) | 1739 | 4068 | 1592 | 69 |
| H(02A) | 4217 | 2630 | 1431 | 78 |
| H(02B) | 2286 | 2041 | 937 | 78 |
| H(011) | −3310 | 3147 | −1038 | 83 |
| H(017) | −3508 | −231 | 603 | 84 |
| H(019) | −1524 | 589 | 2126 | 72 |
| H(01C) | −1161 | 4653 | 2437 | 66 |
| H(01D) | −1948 | 3717 | 3307 | 66 |
| H(023) | 1749 | 5782 | 3012 | 66 |
| H(01A) | 3512 | 3455 | 3817 | 75 |
| H(01B) | 4331 | 4424 | 2982 | 75 |
| H(01E) | 3030 | 5301 | 5318 | 82 |
| H(01F) | 4283 | 6033 | 4535 | 82 |
| H(99A) | 1668 | 1759 | 6426 | 138 |
| H(99B) | 1017 | 3194 | 6227 | 138 |
| H(98A) | 920(90) | 7340(120) | 5120(90) | 80(30) |
| H(99A) | 800(180) | −230(130) | 4410(80) | 70(30) |
| H(99B) | 2740(100) | −420(70) | 4230(40) | 5(14) |

Example 4

(4aR,6R,8aS)-8a-(2,4-Difluorophenyl)-6-(fluoromethyl)-4,4-a,5,6,8,8a-hexahydropyrano[3,4-d][1,3]thiazin-2-amine (4)

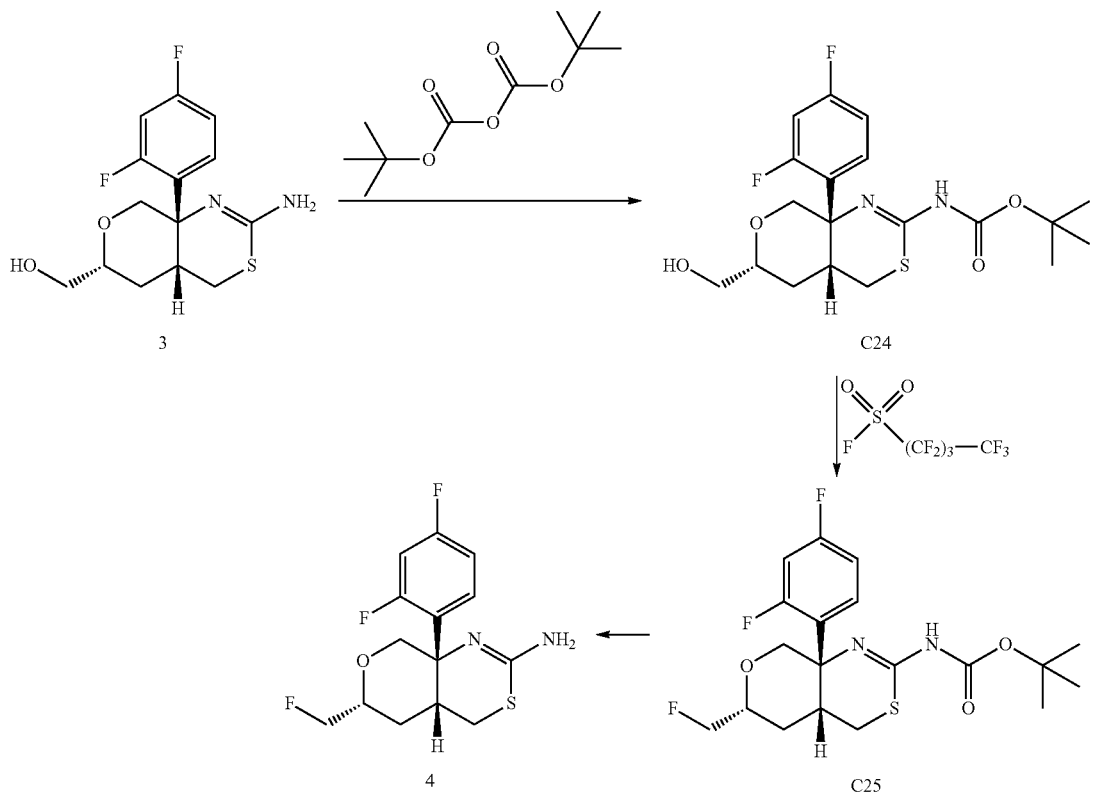

Step 1. Synthesis of tert-butyl [(4aR,6R,8aS)-8a-(2,4-difluorophenyl)-6-(hydroxymethyl)-4,4-a,5,6,8,8a-hexahydropyrano[3,4-d][1,3]thiazin-2-yl]carbamate (C24)

Triethylamine (0.168 mL, 1.20 mmol) was added to a solution of [(4aR,6R,8aS)-2-amino-8a-(2,4-difluorophenyl)-4,4-a,5,6,8,8a-hexahydropyrano[3,4-d][1,3]thiazin-6-yl]methanol (3) (235 mg, 0.748 mmol) in a mixture of tetrahydrofuran (2 mL) and methanol (1 mL). Di-tert-butyl dicarbonate (212 mg, 0.971 mmol) was then added, and the reaction mixture was allowed to stir at room temperature for 18 hours. Solvents were removed in vacuo, and the residue was taken up in ethyl acetate and washed with water, washed with saturated aqueous sodium chloride solution, dried over sodium sulfate, filtered, and concentrated under reduced pressure. Purification via silica gel chromatography (Gradient: 0% to 10% methanol in dichloromethane) provided the product as a white foam. Yield: 257 mg, 0.620 mmol, 83%. LCMS m/z 415.3 (M+1). $^1$H NMR (400 MHz, CD$_3$OD) δ 1.50 (s, 9H), 1.60-1.68 (m, 1H), 1.71-1.83 (m, 1H), 2.71 (dd, J=12.8, 2.6 Hz, 1H), 2.91 (dd, J=13.2, 4.0 Hz, 1H), 3.05-3.15 (br m, 1H), 3.58 (d, J=5.1 Hz, 2H), 3.69-3.76 (m, 1H), 3.80 (d, J=11.7 Hz, 1H), 4.07-4.12 (m, 1H), 7.00-7.09 (m, 2H), 7.32-7.40 (m, 1H).

Step 2. Synthesis of tert-butyl [(4aR,6R,8aS)-8a-(2,4-difluorophenyl)-6-(fluoromethyl)-4,4-a,5,6,8,8a-hexahydropyrano[3,4-d][1,3]thiazin-2-yl]carbamate (C25)

tert-Butyl [(4aR,6R,8aS)-8a-(2,4-difluorophenyl)-6-(hydroxymethyl)-4,4-a,5,6,8,8a-hexahydropyrano[3,4-d][1,3]thiazin-2-yl]carbamate (C24) (82 mg, 0.20 mmol) was dissolved in a mixture of acetonitrile (0.8 mL) and tetrahydrofuran (0.2 mL). 1,1,2,2,3,3,4,4,4-Nonafluorobutane-1-sulfonyl fluoride (71.1 μL, 0.396 mmol) was added, followed by triethylamine trihydrofluoride (64.4 μL, 0.395 mmol), and then triethylamine (0.166 mL, 1.19 mmol), and the reaction mixture was allowed to stir at room temperature for 18 hours. Saturated aqueous sodium bicarbonate solution was added, and the mixture was extracted three times with dichloromethane. The combined organic extracts were washed with water, washed with saturated aqueous sodium chloride solution, dried over sodium sulfate, filtered, and concentrated in vacuo. Purification via preparative thin layer chromatography on silica gel (Eluent: 5% methanol in dichloromethane) afforded the product as a pale yellow foam. Yield: 22 mg, 0.053 mmol, 27%. LCMS m/z 415.4 (M−1). $^1$H NMR (400 MHz, CDCl$_3$), characteristic peaks: δ 1.53 (s, 9H), 1.87-1.99 (m, 1H), 2.57 (dd, J=12.9, 2.8 Hz, 1H), 2.93 (dd, J=12.9, 3.8 Hz, 1H), 3.01-3.10 (br m, 1H), 3.79 (br d, J=12 Hz, 1H), 3.91-4.03 (m, 1H), 4.15 (dd, J=11.9, 1.9 Hz, 1H), 4.42 (ddd, half of ABXY pattern, J=46.7, 9.9, 3.6 Hz, 1H), 4.50 (ddd, half of ABXY pattern, J=47.7, 9.9, 6.4 Hz, 1H), 6.85 (ddd, J=12.4, 8.4, 2.4 Hz, 1H), 6.89-6.96 (m, 1H), 7.28-7.36 (m, 1H).

Step 3. Synthesis of (4aR,6R,8aS)-8a-(2,4-difluorophenyl)-6-(fluoromethyl)-4,4-a,5,6,8,8a-hexahydropyrano[3,4-d][1,3]thiazin-2-amine (4)

tert-Butyl [(4aR,6R,8aS)-8a-(2,4-difluorophenyl)-6-(fluoromethyl)-4,4-a,5,6,8,8a-hexahydropyrano[3,4-d][1,3]thiazin-2-yl]carbamate (C25) was converted to the product according to the general procedure for the synthesis of (4aR,6R,8aS)-8a-(2-fluorophenyl)-6-[(propan-2-yloxy)methyl]-4,4-a,5,6,8,8a-hexahydropyrano[3,4-d][1,3]thiazin-2-amine, trifluoroacetate salt (2) in Example 2. In this case, the reversed-phase HPLC purification was carried out using a different system (Column: Waters XBridge C18, 5 μm; Mobile phase A: 0.03% ammonium hydroxide in water (v/v); Mobile phase B: 0.03% ammonium hydroxide in acetonitrile (v/v); Gradient: 5% to 100% B), affording the product as an oil. Yield: 17 mg, 0.054 mmol, quantitative. LCMS m/z 317.2 (M+1). $^1$H NMR (600 MHz, DMSO-d$_6$) δ 1.56-1.64 (m, 1H), 1.66-1.72 (m, 1H), 2.88 (dd, J=13.2, 3.5 Hz, 1H), 3.02 (br d, J=13 Hz, 1H), 3.14-3.21 (m, 1H), 3.88 (d, half of AB quartet, J=12.3 Hz, 1H), 3.92-4.01 (m, 2H), 4.38-4.57 (m, 2H), 7.21-7.26 (m, 1H), 7.28-7.34 (m, 1H), 7.36-7.41 (m, 1H).

Example 5

(4aR,6R,8aS)-6-(Fluoromethyl)-8a-(2-fluorophenyl)-4,4-a,5,6,8,8a-hexahydropyrano[3,4-d][1,3]thiazin-2-amine (5)

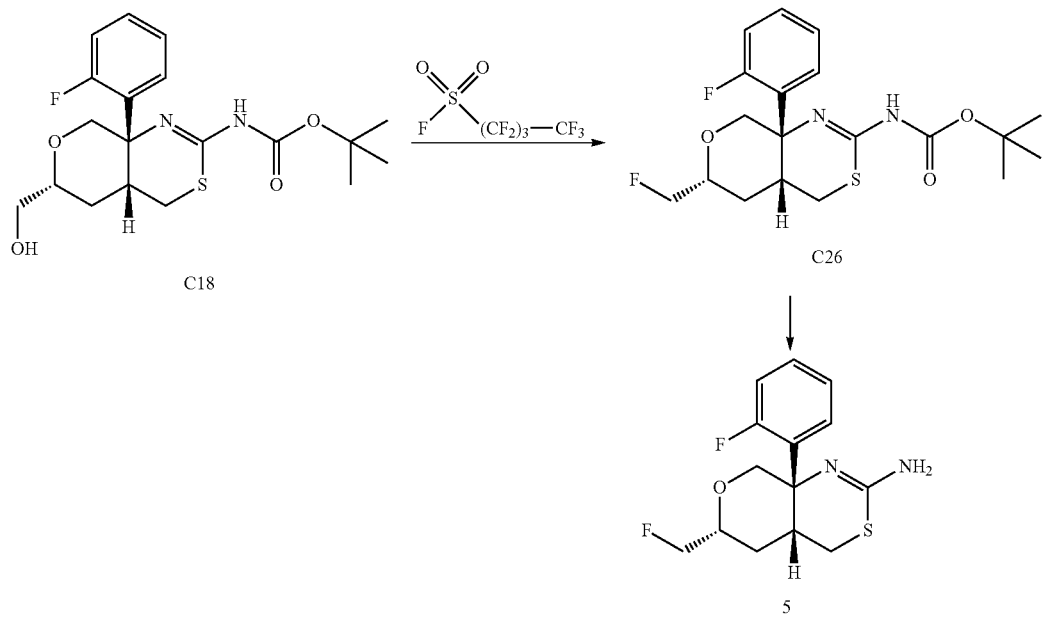

Step 1. Synthesis of tert-butyl [(4aR,6R,8aS)-6-(fluoromethyl)-8a-(2-fluorophenyl)-4,4-a,5,6,8,8a-hexahydropyrano[3,4-d][1,3]thiazin-2-yl]carbamate (C26)

Compound C26 was prepared from tert-butyl [(4aR,6R,8aS)-8a-(2-fluorophenyl)-6-(hydroxymethyl)-4,4-a,5,6,8,8a-hexahydropyrano[3,4-d][1,3]thiazin-2-yl]carbamate (C18) according to the general procedure for the synthesis of tert-butyl [(4aR,6R,8aS)-8a-(2,4-difluorophenyl)-6-(fluoromethyl)-4,4-a,5,6,8,8a-hexahydropyrano[3,4-d][1,3]thiazin-2-yl]carbamate (C25) in Example 4, except that no chromatography was carried out on the crude product. Yield: 40 mg, 0.10 mmol, 100%. LCMS m/z 397.4 (M−1).

Step 2. Synthesis of (4aR,6R,8aS)-6-(fluoromethyl)-8a-(2-fluorophenyl)-4,4-a,5,6,8,8a-hexahydropyrano[3,4-d][1,3]thiazin-2-amine (5)

tert-Butyl [(4aR,6R,8aS)-6-(fluoromethyl)-8a-(2-fluorophenyl)-4,4-a,5,6,8,8a-hexahydropyrano[3,4-d][1,3]thiazin-2-yl]carbamate (C26) was converted to the product according to the general procedure for the synthesis of (4aR,6R,8aS)-8a-(2-fluorophenyl)-6-[(propan-2-yloxy)methyl]-4,4-a,5,6,8,8a-hexahydropyrano[3,4-d][1,3]thiazin-2-amine, trifluoroacetate salt (2) in Example 2. In this case, the reversed-phase HPLC purification was carried out using a different system (Column: Waters XBridge C18, 5 μm; Mobile phase A: 0.03% ammonium hydroxide in water (v/v); Mobile phase B: 0.03% ammonium hydroxide in acetonitrile (v/v); Gradient: 25% to 100% B). Yield: 3 mg, 0.01 mmol, 10%. LCMS m/z 299.1 (M+1). $^1$H NMR (600 MHz, DMSO-$d_6$) δ 1.43-1.48 (m, 1H), 1.63-1.72 (m, 1H), 2.64-2.72 (m, 2H), 2.75-2.80 (m, 1H), 3.60 (d, J=11.0 Hz, 1H), 3.76-3.85 (m, 1H), 3.96 (dd, J=10.8, 1.5 Hz, 1H), 4.30-4.48 (m, 2H), 6.13 (br s, 2H), 7.14-7.22 (m, 2H), 7.30-7.36 (m, 2H).

TABLE 11

| Example Number | Method of preparation; starting material(s) | Structure | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated)$^h$ |
|---|---|---|---|
| 6 | Ex 1; C23 | 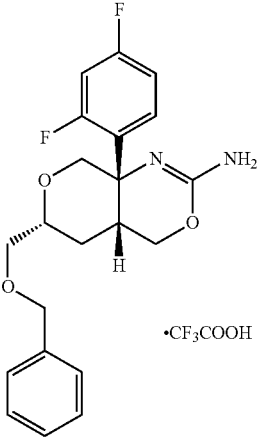 [SMILES: NC1=N[C@@]2(c3ccc(F)cc3F)CO[C@@H](COCc3ccccc3)C[C@H]2CO1 ; "·CF3COOH"] | $^1$H NMR (600 MHz, DMSO-$d_6$) δ 1.53-1.59 (m, 1H), 1.61-1.69 (m, 1H), 2.74 (br s, 2H), 2.77-2.83 (m, 1H), 3.43 (dd, half of ABX pattern, J = 10.3, 4.2 Hz, 1H), 3.50 (dd, half of ABX pattern, J = 10.3, 5.9 Hz, 1H), 3.63 (br d, J = 11 Hz, 1H), 3.73-3.78 (m, 1H), 3.88 (dd, J = 11.2, 1.5 Hz, 1H), 4.51 (AB quartet, $J_{AB}$ = 11.9 Hz, $\Delta v_{AB}$ = 18.0 Hz, 2H), 7.10-7.15 (m, 1H), 7.21-7.27 (m, 1H), 7.27-7.38 (m, 6H); 405.1 |
| 7 | Ex. 4$^a$; C18 | 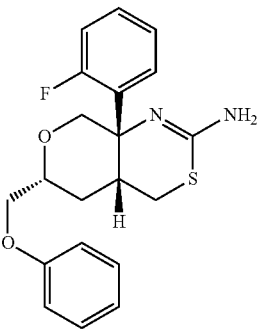 [SMILES: NC1=N[C@@]2(c3ccccc3F)CO[C@@H](COc3ccccc3)C[C@H]2CS1] | $^1$H NMR (600 MHz, DMSO-$d_6$) δ 1.59-1.64 (m, 1H), 1.71-1.78 (m, 1H), 2.67-2.73 (m, 2H), 2.77-2.83 (m, 1H), 3.61 (d, J = 11.0 Hz, 1H), 3.88-4.01 (m, 4H), 6.13 (br s, 2H), 6.91-6.97 (m, 3H), 7.15-7.22 (m, 2H), 7.26-7.30 (m, 2H), 7.31-7.36 (m, 2H); 373.1 |

TABLE 11-continued

| Example Number | Method of preparation; starting material(s) | Structure | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated)$^h$ |
|---|---|---|---|
| 8 | Ex. 4$^b$; C18 | (structure: fluorophenyl-fused pyranothiazine with CH$_2$O-pyridinyl substituent, NH$_2$) | $^1$H NMR (600 MHz, DMSO-d$_6$), characteristics peaks: δ 1.60-1.66 (m, 1H), 1.67-1.76 (m, 1H), 3.65 (br d, J = 10.5 Hz, 1H), 3.91-3.98 (m, 2H), 4.25 (dd, half of ABX pattern, J = 11.4, 6.6 Hz, 1H), 4.28 (dd, half of ABX pattern, J = 11.4, 4.0 Hz, 1H), 6.83 (d, J = 8.4 Hz, 1H), 6.96-7.00 (m, 1H), 7.16-7.24 (m, 2H), 7.31-7.38 (m, 2H), 7.71 (ddd, J = 8.4, 7.0, 1.8 Hz, 1H), 8.16 (dd, J = 4.8, 1.8 Hz, 1H); 374.1 |
| 9 | Ex 2; C19 | (structure: fluorophenyl-fused pyranothiazine with CH$_2$OCH$_2$CH$_3$ substituent, NH$_2$) ·CF$_3$COOH | $^1$H NMR (600 MHz, DMSO-d$_6$) δ 1.11 (t, J = 7.0 Hz, 1H), 1.51-1.60 (m, 1H), 1.69-1.75 (m, 1H), 2.84 (dd, J = 13.0, 3.7 Hz, 1H), 3.04 (dd, J = 13.2, 2.6 Hz, 1H), 3.17-3.23 (m, 1H), 3.40-3.51 (m, 4H), 3.80-3.86 (m, 1H), 3.91 (AB quartet, J$_{AB}$ = 12.3 Hz, Δν$_{AB}$ = 34.3 Hz, 2H), 7.23-7.28 (m, 1H), 7.29-7.36 (m, 2H), 7.46-7.51 (m, 1H), 10.86 (br s, 1H); 325.1 |
| 10 | Ex. 1$^c$; C8 | (structure: 2,4-difluorophenyl-fused pyranothiazine, NH$_2$, (+/-)) | $^1$H NMR (600 MHz, DMSO-d$_6$) δ 1.42-1.49 (m, 1H), 1.80-1.89 (m, 1H), 2.68-2.79 (m, 3H), 3.49-3.58 (m, 2H), 3.81 (dd, J = 11.0, 2.2 Hz, 1H), 3.90-3.95 (m, 1H), 7.11 (ddd, J = 8.4, 8.4, 2.4 Hz, 1H), 7.22 (ddd, J = 12.7, 9.0, 2.4 Hz, 1H), 7.34 (ddd, J = 9.2, 8.8, 7.0 Hz, 1H); 285.2 |
| 11 | Ex. 1$^c$; C8 | (structure: 4-fluorophenyl-fused pyranothiazine, NH$_2$, (+/-)) | $^1$H NMR (600 MHz, DMSO-d$_6$) δ 1.37-1.42 (m, 1H), 1.83-1.92 (m, 1H), 2.41-2.47 (m, 1H), 2.59 (dd, half of ABX pattern, J = 12.3, 2.6 Hz, 1H), 2.68 (dd, half of ABX pattern, J = 12.3, 4.0 Hz, 1H), 3.51 (AB quartet, J$_{AB}$ = 10.8 Hz, Δν$_{AB}$ = 43.3 Hz, 2H), 3.56-3.61 (m, 1H), 3.90 (br dd, J = 11.0, 4.0 Hz, 1H), 6.10 (br s, 2H), 7.15 (br dd, J = 8.8, 8.8 Hz, 2H), 7.37-7.42 (m, 2H); 267.2 |
| 12 | Ex. 1$^c$; C8 | (structure: 2-fluorophenyl-fused pyranothiazine, NH$_2$, (+/-)) | 1.39-1.42 (m, 1H), 2.07-2.20 (m, 1H), 2.61 (dd, J = 11.9, 2.6 Hz, 1H), 2.88-2.99 (m, 2H), 3.65-3.73 (m, 1H), 3.77 (d, J = 11.0 Hz, 1H), 4.05-4.13 (m, 2H), 7.03 (ddd, J = 12.8, 8.2, 1.1 Hz, 1H), 7.13 (ddd, J = 7.8, 7.5, 1.2 Hz, 1H), 7.23-7.29 (m, 1H), 7.36 (ddd, J = 8.0, 8.0, 1.8 Hz, 1H); 266.9 |

TABLE 11-continued

| Example Number | Method of preparation; starting material(s) | Structure | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated)[h] |
|---|---|---|---|
| 13 | Ex. 1[c]; C8 | 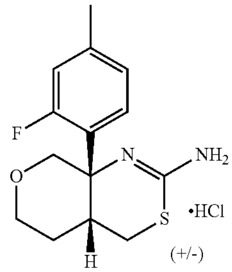 [SMILES: Cc1ccc([C@]23COCC[C@H]2CSC(N)=N3)c(F)c1 ; Cl] | 1.38-1.46 (m, 1H), 2.06-2.18 (m, 1H), 2.32 (s, 3H), 2.59 (dd, J = 12.2, 2.8 Hz, 1H), 2.84-2.92 (m, 1H), 2.98 (dd, J = 12.2, 4.2 Hz, 1H), 3.62-3.71 (m, 1H), 3.75 (d, J = 10.9 Hz, 1H), 4.03 (dd, J = 11.0, 2.2 Hz, 1H), 4.08 (br dd, J = 11.2, 4.8 Hz, 1H), 4.67 (br s, 2H), 6.82-6.87 (m, 1H), 6.91-6.94 (m, 1H), 7.22 (dd, J = 8.4, 8.2 Hz, 1H); 281.1 |
| 14 | Ex. 1[c]; C8 | 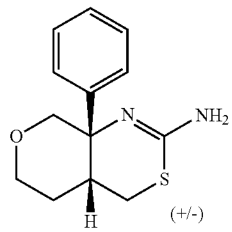 [SMILES: NC1=N[C@@]2(c3ccccc3)COCC[C@H]2CS1] | $^1$H NMR (600 MHz, DMSO-d$_6$) δ 1.38-1.44 (m, 1H), 1.84-1.93 (m, 1H), 2.45-2.50 (m, 1H, assumed; partially obscured by solvent peak), 2.60 (br dd, half of ABX pattern, J = 12, 3 Hz, 1H), 2.68 (dd, half of ABX pattern, J = 12.3, 4.0 Hz, 1H), 3.54 (AB quartet, J$_{AB}$ = 11.0 Hz, Δν$_{AB}$ = 31.1 Hz, 2H), 3.57-3.62 (m, 1H), 3.91 (br dd, J = 11, 4 Hz, 1H), 7.22-7.26 (m, 1H), 7.32-7.39 (m, 4H); 249.2 |
| 15 | Ex. 5[d]; C18 | 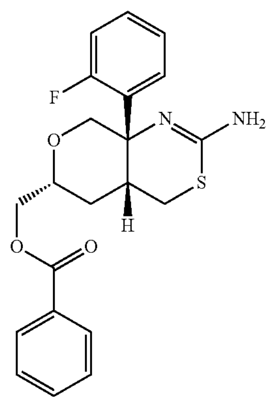 [SMILES: NC1=N[C@@]2(c3ccccc3F)CO[C@@H](COC(=O)c3ccccc3)C[C@H]2CS1] | $^1$H NMR (600 MHz, DMSO-d$_6$) δ 1.56-1.62 (m, 1H), 1.79-1.87 (m, 1H), 2.68-2.72 (m, 2H), 2.77-2.84 (m, 1H), 3.61 (d, J = 10.5 Hz, 1H), 3.91-3.96 (m, 1H), 3.99 (dd, J = 10.5, 1.5 Hz, 1H), 4.30 (d, J = 4.8 Hz, 2H), 6.19 (br s, 2H), 7.15-7.22 (m, 2H), 7.31-7.37 (m, 2H), 7.55 (br dd, J = 7.9, 7.9 Hz, 2H), 7.65-7.69 (m, 1H), 7.98-8.01 (m, 2H); 401.1 |
| 16 | Ex. 1[c, e]; C8 | 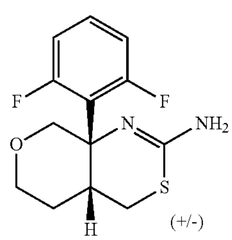 [SMILES: NC1=N[C@@]2(c3c(F)cccc3F)COCC[C@H]2CS1] | $^1$H NMR (400 MHz, CD$_3$OD) δ 1.52-1.61 (m, 1H), 1.96-2.09 (m, 1H), 2.90-2.96 (m, 1H), 3.13-3.25 (m, 2H), 3.67 (ddd, J = 12.0, 11.7, 2.4 Hz, 1H), 3.97 (AB quartet, J$_{AB}$ = 11.5 Hz, Δν$_{AB}$ = 30.3 Hz, 2H), 4.02-4.08 (m, 1H), 6.99-7.06 (m, 2H), 7.41 (tt, J = 8.4, 6.0 Hz, 1H); 285.1 |
| 17 | Ex. 1[c]; C8 | 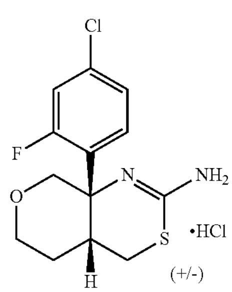 [SMILES: NC1=N[C@@]2(c3ccc(Cl)cc3F)COCC[C@H]2CS1 ; Cl] | 1.38-1.45 (m, 1H), 2.05-2.17 (m, 1H), 2.61 (dd, J = 12.3, 2.8 Hz, 1H), 2.80-2.87 (m, 1H), 2.93 (dd, J = 12.3, 4.2 Hz, 1H), 3.65 (ddd, J = 11.9, 11.9, 2.4 Hz, 1H), 3.71 (d, J = 11.0 Hz, 1H), 3.99 (dd, J = 11.0, 2.4 Hz, 1H), 4.07 (br dd, J = 11.3, 4.7 Hz, 1H), 4.63 (br s, 2H), 7.06 (dd, J = 12.1, 2.1 Hz, 1H), 7.09-7.12 (m, 1H), 7.32 (dd, J = 8.7, 8.5 Hz, 1H); 301.0 |

TABLE 11-continued

| Example Number | Method of preparation; starting material(s) | Structure | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated)$^h$ |
|---|---|---|---|
| 18 | Ex. 1$^{c, f}$; C8 | (structure with OH, F, pyran-thiazine, •NH$_3$, (+/−)) | 1.51 minutes$^h$; 283.0 |
| 19 | Ex. 1$^c$; C8 | (structure with OMe-phenyl, pyran-thiazine, (+/−)) | $^1$H NMR (600 MHz, DMSO-d$_6$) δ 1.32-1.37 (m, 1H), 1.82-1.91 (m, 1H), 2.57 (dd, half of ABX pattern, J = 12.3, 2.9 Hz, 1H), 2.63 (dd, half of ABX pattern, J = 12.3, 4.0 Hz, 1H), 3.11-3.16 (m, 1H), 3.38 (d, J = 10.1 Hz, 1H), 3.47-3.53 (m, 1H), 3.81 (s, 3H), 3.88 (br dd, J = 11, 4 Hz, 1H), 4.16 (d, J = 10.3 Hz, 1H), 5.97 (br s, 2H), 6.90 (br dd, J = 7.5, 7.5 Hz, 1H), 7.01 (br d, J = 8.6 Hz, 1H), 7.21-7.25 (m, 2H); 279.1 |
| 20 | Ex. 1$^c$; enantiomer of C9$^g$ | (structure with 2,4-difluorophenyl, pyran-thiazine) | $^1$H NMR (400 MHz, CD$_3$OD) δ 1.44-1.52 (m, 1H), 1.99-2.12 (m, 1H), 2.65-2.73 (m, 1H), 2.81-2.89 (m, 2H), 3.62-3.69 (m, 1H), 3.63 (d, J = 11.0 Hz, 1H), 3.99-4.05 (m, 1H), 4.01 (dd, J = 11.1, 2.2 Hz, 1H), 6.92-7.00 (m, 2H), 7.35 (ddd, J = 9.4, 8.9, 6.7 Hz, 1H); 285.0 |
| 21 | Ex. 2$^i$; C18 | (structure with 2-fluorophenyl, pyran-thiazine, pyrazinyloxymethyl, •CF$_3$COOH) | 1.92 minutes$^h$; 375.2 |

TABLE 11-continued

| Example Number | Method of preparation; starting material(s) | Structure | $^1$H NMR (400 MHz, CDCl$_3$), δ (ppm); Mass spectrum, observed ion m/z (M + 1) or HPLC retention time (minutes); Mass spectrum m/z (M + 1) (unless otherwise indicated)[h] |
|---|---|---|---|
| 22 | Ex. 2[i]; C18 | [structure with ·CF$_3$COOH] | 1.84 minutes[h]; 375.2 |

[a]Compound C18 was subjected to a Mitsunobu reaction with phenol. The resulting phenyl ether was deprotected as in Example 4 to provide the product.
[b]Compound C18 was subject to a Mitsunobu reaction with pyridin-2-ol. The resulting pyridyl ether was deprotected as in Example 4 to provide the product.
[c]This Example was prepared in the same manner as Example 1, except that racemic compound C8 was used instead of enantiomer C9.
[d]Instead of the fluorination described in Example 5, primary alcohol C18 was reacted with benzoyl chloride to provide the corresponding ester. The resulting ester was deprotected as described in Example 5 to provide the product.
[e]In the case, the reductive N—O cleavage was carried out with lithium aluminum hydride rather than zinc. Removal of the fluorenylmethoxycarbonyl protecting group was effected with 1,8-diazabicyclo[5.4.0]undec-7-ene and octane-1-thiol, according to the method of J. E. Sheppeck II et al., Tetrahedron Lett. 2000, 41, 5329-5333.
[f]Compound C8 was reacted with benzyl 4-bromo-3-fluorophenyl ether in this case. The benzyl protecting group was removed after cyclization: treatment of 9H-fluoren-9-ylmethyl {cis-8a-[4-(benzyloxy)-2-fluorophenyl]-4,4a,5,6,8,8a-hexahydropyrano[3,4-d][1,3]thiazin-2-yl}carbamate with concentrated hydrochloric acid for 3 hours at 120° C. provided the fluorenylmethoxycarbonyl-protected final compound.
[g]The enantiomer of C9 {(3aS)-3,3a,4,5-tetrahydro-7H-pyrano[3,4-c][1,2]oxazole} was used as starting material; this was obtained as the first-eluting enantiomer from the separation described for isolation of C9 in Step 5 of Example 1.
[h]HPLC conditions. Column: Waters Atlantis dC18, 4.6 × 50 mm, 5 µm; Mobile phase A: 0.05% trifluoroacetic acid in water (v/v); Mobile phase B: 0.05% trifluoroacetic acid in acetonitrile (v/v); Gradient: 5% to 95% B over 4.0 minutes, linear; Flow rate: 2 mL/minute.
[i]Compound C18 was deprotonated with sodium hydride and then reacted with the appropriate chloro-substituted heterocyclic reagent. The resulting heteroaryl ether was deprotected as in Example 2 to provide the product.

Biological Assays

Cell-Free Assay:

Beta-secretase (BACE) is one of the enzymes involved in the generation of the amyloid beta peptide found in the amyloid plaques of Alzheimer's Disease patients. This assay measures the inhibition of the beta-secretase enzyme as it cleaves a non-native peptide.

A synthetic APP substrate that can be cleaved by beta-secretase having N-terminal biotin and made fluorescent by the covalent attachment of Oregon Green at the Cys residue is used to assay beta-secretase activity in the presence or absence of the inhibitory compounds. The substrate is Biotin-GLTNIKTEEISEISY^EVEFR-C[Oregon Green]KK-OH. The BACE1 enzyme is affinity purified material from conditioned media of CHO-K1 cells that have been transfected with a soluble BACE construct (BACE1deltaTM96His). Compounds are incubated in a ½ log dose response curve from a top concentration of 100 µM with BACE1 enzyme and the biotinylated fluorescent peptide in 384-well black plates (Thermo Scientific #4318). BACE1 is at a final concentration of 0.1 nM with a final concentration of peptide substrate of 150 nM in a reaction volume of 30 µL assay buffer (100 mM Sodium Acetate, pH 4.5 (brought to pH with acetic acid), and 0.001% Tween-20). Plates are covered and incubated for 3 hours at 37° C. The reaction is stopped with the addition of 30 µL of 1.5 µM Streptavidin (Pierce, #21125). After a 10 minute incubation at room temperature, plates are read on a PerkinElmer Envision for fluorescent polarization (Ex485 nm/Em530 nm). The activity of the beta-secretase enzyme is detected by changes in the fluorescence polarization that occur when the substrate is cleaved by the enzyme. Incubation in the presence of compound inhibitor demonstrates specific inhibition of beta-secretase enzymatic cleavage of the synthetic APP substrate.

Whole Cell-Free Assay (In Vitro sAPPb Assay):

H4 human neuroglioma cells over-expressing the wild-type human APP$_{695}$ are treated for 18 hours with compound in a final concentration 1% DMSO. sAPPβ levels are measured using TMB-ELISA with capture APP N-terminal antibody (Affinity BioReagents, OMA1-03132), wild-type sAPPβ specific reporter p192 (Elan), and tertiary anti rabbit-HRP (GE Healthcare).

TABLE 12

| | Biological Activity of Examples 1-22 | | |
|---|---|---|---|
| Example Number | IUPAC NAME | BACE1 Cell-Free Assay IC$_{50}$ (μM)[a] | sAPPβ Whole Cell-Free Assay IC$_{50}$ (nM)[3] |
| 1 | (4aR,8aS)-8a-(2,4-Difluorophenyl)-4,4a,5,6,8,8a-hexahydropyrano[3,4-d][1,3]thiazin-2-amine | 6.70[b] | 211 |
| 2 | (4aR,6R,8aS)-8a-(2-Fluorophenyl)-6-[(propan-2-yloxy)methyl]-4,4a,5,6,8,8a-hexahydropyrano[3,4-d][1,3]thiazin-2-amine, trifluoroacetate salt | 0.396 | 72.9 |
| 3 | [(4aR,6R,8aS)-2-Amino-8a-(2,4-difluorophenyl)-4,4a,5,6,8,8a-hexahydropyrano[3,4-d][1,3]thiazin-6-yl]methanol | 2.27 | 436 |
| 4 | (4aR,6R,8aS)-8a-(2,4-Difluorophenyl)-6-(fluoromethyl)-4,4a,5,6,8,8a-hexahydropyrano[3,4-d][1,3]thiazin-2-amine | 1.39 | 72.5 |
| 5 | (4aR,6R,8aS)-6-(Fluoromethyl)-8a-(2-fluorophenyl)-4,4a,5,6,8,8a-hexahydropyrano[3,4-d][1,3]thiazin-2-amine | 0.838[b] | 83.4 |
| 6 | (4aR,6R,8aS)-6-[(Benzyloxy)methyl]-8a-(2,4-difluorophenyl)-4,4a,5,6,8,8a-hexahydropyrano[3,4-d][1,3]thiazin-2-amine, trifluoroacetic acid salt | 0.0323 | 64.6 |
| 7 | (4aR,6R,8aS)-8a-(2-Fluorophenyl)-6-(phenoxymethyl)-4,4a,5,6,8,8a-hexahydropyrano[3,4-d][1,3]thiazin-2-amine | 0.826 | 108 |
| 8 | (4aR,6R,8aS)-8a-(2-Fluorophenyl)-6-[(pyridin-2-yloxy)methyl]-4,4a,5,6,8,8a-hexahydropyrano[3,4-d][1,3]thiazin-2-amine | 2.38 | 239 |
| 9 | (4aR,6R,8aS)-6-(Ethoxymethyl)-8a-(2-fluorophenyl)-4,4a,5,6,8,8a-hexahydropyrano[3,4-d][1,3]thiazin-2-amine, trifluoroacetic acid salt | 0.914 | 80.0 |
| 10 | rel-(4aR,8aS)-8a-(2,4-Difluorophenyl)-4,4a,5,6,8,8a-hexahydropyrano[3,4-d][1,3]thiazin-2-amine | 5.10 | 265 |
| 11 | rel-(4aR,8aS)-8a-(4-Fluorophenyl)-4,4a,5,6,8,8a-hexahydropyrano[3,4-d][1,3]thiazin-2-amine | 7.52 | 380 |
| 12 | rel-(4aR,8aS)-8a-(2-Fluorophenyl)-4,4a,5,6,8,8a-hexahydropyrano[3,4-d][1,3]thiazin-2-amine | 7.95 | 436 |
| 13 | rel-(4aR,8aS)-8a-(2-Fluoro-4-methylphenyl)-4,4a,5,6,8,8a-hexahydropyrano[3,4-d][1,3]thiazin-2-amine, hydrochloride salt | 3.73 | 438 |
| 14 | rel-(4aR,8aS)-8a-Phenyl-4,4a,5,6,8,8a-hexahydropyrano[3,4-d][1,3]thiazin-2-amine | 10.4 | 477 |
| 15 | [(4aR,6R,8aS)-2-Amino-8a-(2-fluorophenyl)-4,4a,5,6,8,8a-hexahydropyrano[3,4-d][1,3]thiazin-6-yl]methyl benzoate | 13.0 | 492 |
| 16 | rel-(4aR,8aS)-8a-(2,6-Difluorophenyl)-4,4a,5,6,8,8a- | 13.8[b] | 506 |

TABLE 12-continued

Biological Activity of Examples 1-22

| Example Number | IUPAC NAME | BACE1 Cell-Free Assay IC$_{50}$ (μM)$^a$ | sAPPβ Whole Cell-Free Assay IC$_{50}$ (nM)$^3$ |
|---|---|---|---|
| | hexahydropyrano[3,4-d][1,3]thiazin-2-amine | | |
| 17 | rel-(4aR,8aS)-8a-(4-chloro-2-Fluorophenyl)-4,4a,5,6,8,8a-hexahydropyrano[3,4-d][1,3]thiazin-2-amine, hydrochloride salt | 10.2 | 775 |
| 18 | rel-4-[(4aR,8aS)-2-Amino-4,4a,5,6-tetrahydropyrano[3,4-d][1,3]thiazin-8a(8H)-yl]-3-fluorophenol, ammonium salt | 5.35 | 1000 |
| 19 | rel-(4aR,8aS)-8a-(2-Methoxyphenyl)-4,4a,5,6,8,8a-hexahydropyrano[3,4-d][1,3]thiazin-2-amine | >100 | 4030$^b$ |
| 20 | (4aS,8aR)-8a-(2,4-Difluorophenyl)-4,4a,5,6,8,8a-hexahydropyrano[3,4-d][1,3]thiazin-2-amine | >100 | >27100 |
| 21 | (4aR,6R,8aS)-8a-(2-Fluorophenyl)-6-[(pyrazin-2-yloxy)methyl]-4,4a,5,6,8,8a-hexahydropyrano[3,4-d][1,3]thiazin-2-amine, trifluoroacetic acid salt | 2.03$^b$ | 23.1$^b$ |
| 22 | (4aR,6R,8aS)-8a-(2-Fluorophenyl)-6-[(pyrimidin-2-yloxy)methyl]-4,4a,5,6,8,8a-hexahydropyrano[3,4-d][1,3]thiazin-2-amine, trifluoroacetic acid salt | 8.03$^b$ | 71.1$^b$ |

$^a$Reported IC$_{50}$ values are the geometric mean of 2-4 determinations.
$^b$IC$_{50}$ value is from a single determination.

The compounds depicted in Table 13 may be prepared as described in the General Schemes above or as described in WO 2010/038686. This reference is incorporated herein in its entirety and for all purposes. These compounds are useful in the treatment of neurodegenerative diseases, including Alzheimer's Disease.

TABLE 13

Biological Activity of Examples 23-31

| Example No. | Structure | BACE1 Cell-free Assay IC$_{50}$ (nM)$^a$ | sAPPβ Whole-Cell Assay IC$_{50}$ (nM)$^a$ |
|---|---|---|---|
| 23 | [structure: 2-fluorophenyl hexahydropyrano-thiazin-2-amine (+/−)] | 7950 | 436 |
| 24 | [structure: 2-fluorophenyl hexahydropyrano-thiazin-2-amine] | 4540 | 452 |
| 25 | [structure: 2-(trifluoromethoxy)phenyl hexahydropyrano-thiazin-2-amine (+/−)] | 87900$^b$ | N.D.$^c$ |

TABLE 13-continued

Biological Activity of Examples 23-31

| Example No. | Structure | BACE1 Cell-free Assay IC$_{50}$ (nM)$^a$ | sAPPβ Whole-Cell Assay IC$_{50}$ (nM)$^a$ |
|---|---|---|---|
| 26 | 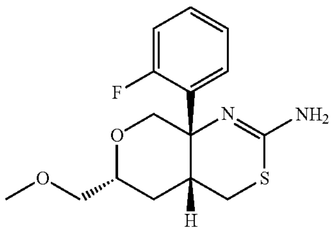 [SMILES: COC[C@H]1C[C@H]2CSC(N)=N[C@@]2(c2ccccc2F)CO1] | 1240 | 148 |
| 27 | 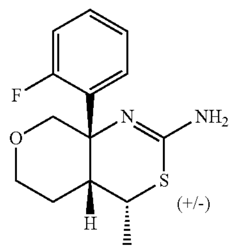 | 6720 | 434 |
| 28 | 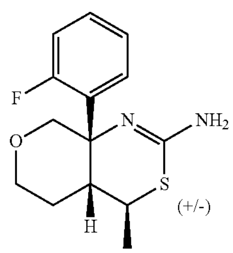 | 11200 | 445 |
| 29 | 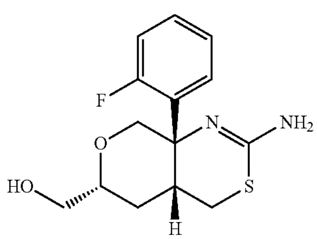 [SMILES: NC1=N[C@@]2(c3ccccc3F)CO[C@@H](CO)C[C@H]2CS1] | 8410 | 493 |
| 30 | 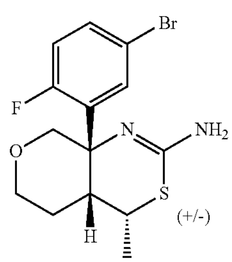 | 27800 | 1650 |
| 31 | 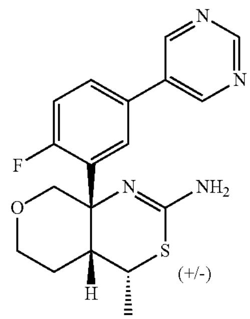 | 3000 | 112 |

$^a$Reported IC$_{50}$ values are the geometric mean of 2-6 determinations.
$^b$IC$_{50}$ value is from a single determination.
$^c$Not determined.

We claim:

1. A compound selected from the group consisting of
   (4aR,6R,8aS)-8a-(2-Fluorophenyl)-6-[(pyridin-2-yloxy)methyl]-4,4a,5,6,8,8a-hexahydropyrano[3,4-d][1,3]thiazin-2-amine;
   (4aR,6R,8aS)-8a-(2-Fluorophenyl)-6-[(pyrazin-2-yloxy)methyl]-4,4a,5,6,8,8a-hexahydropyrano[3,4-d][1,3]thiazin-2-amine; and
   (4aR,6R,8aS)-8a-(2-Fluorophenyl)-6-[(pyrimidin-2-yloxy)methyl]-4,4a,5,6,8,8a-hexahydropyrano[3,4-d][1,3]thiazin-2-amine;
   or a pharmaceutically acceptable salt thereof.

2. A pharmaceutical composition comprising a compound of claim 1, or a pharmaceutically acceptable salt thereof, and a pharmaceutically acceptable vehicle, diluent or carrier.

3. (4aR,6R,8aS)-8a-(2-Fluorophenyl)-6-[(pyridin-2-yloxy)methyl]-4,4a,5,6,8,8a-hexahydropyrano[3,4-d][1,3]thiazin-2-amine; or a pharmaceutically acceptable salt thereof.

4. (4aR,6R,8aS)-8a-(2-Fluorophenyl)-6-[(pyrazin-2-yloxy)methyl]-4,4a,5,6,8,8a-hexahydropyrano[3,4-d][1,3]thiazin-2-amine; or a pharmaceutically acceptable salt thereof.

5. (4aR,6R,8aS)-8a-(2-Fluorophenyl)-6-[(pyrimidin-2-yloxy)methyl]-4,4a,5,6,8,8a-hexahydropyrano[3,4-d][1,3]thiazin-2-amine; or a pharmaceutically acceptable salt thereof.

* * * * *